(12) United States Patent
Mehta et al.

(10) Patent No.: US 9,090,910 B2
(45) Date of Patent: Jul. 28, 2015

(54) METHODS AND SYSTEMS FOR MANIPULATING PARTICLES USING A FLUIDIZED BED

(75) Inventors: Sunil Mehta, Morrisville, NC (US); Tod Herman, Hillsborough, NC (US); Harold Ross, Wake Forest, NC (US); Khurshid Iqbal, Berwyn, PA (US); Joe McMahon, Chapel Hill, NC (US)

(73) Assignee: KBI Biopharma, Inc., Durham, NC (US)

( * ) Notice: Subject to any disclaimer, the term of this patent is extended or adjusted under 35 U.S.C. 154(b) by 420 days.

(21) Appl. No.: 13/054,276

(22) PCT Filed: Jul. 16, 2009

(86) PCT No.: PCT/US2009/004113
§ 371 (c)(1),
(2), (4) Date: May 12, 2011

(87) PCT Pub. No.: WO2010/008563
PCT Pub. Date: Jan. 21, 2010

(65) Prior Publication Data
US 2011/0207225 A1    Aug. 25, 2011

Related U.S. Application Data

(60) Provisional application No. 61/081,171, filed on Jul. 16, 2008, provisional application No. 61/170,584, filed on Apr. 17, 2009.

(51) Int. Cl.
| | |
|---|---|
| *C12N 5/00* | (2006.01) |
| *C12N 5/02* | (2006.01) |
| *C12N 1/00* | (2006.01) |
| *C12M 1/00* | (2006.01) |
| *C12N 15/87* | (2006.01) |
| *C12M 1/12* | (2006.01) |
| *C12M 3/04* | (2006.01) |

(52) U.S. Cl.
CPC ............... *C12N 15/87* (2013.01); *C12M 25/20* (2013.01); *C12M 27/10* (2013.01)
USPC ........... 435/325; 435/374; 435/382; 435/383; 435/243; 435/289.1

(58) Field of Classification Search
None
See application file for complete search history.

(56) References Cited

U.S. PATENT DOCUMENTS

| | | | |
|---|---|---|---|
| 5,510,247 A | 4/1996 | Komives et al. | |
| 5,622,819 A | 4/1997 | Herman | |
| 6,214,617 B1 | 4/2001 | Herman | |
| 6,354,986 B1 * | 3/2002 | Hlavinka et al. | 494/37 |
| 6,617,154 B1 * | 9/2003 | Meserol | 435/285.2 |
| 6,942,804 B2 | 9/2005 | Herman | |
| 2001/0044143 A1 | 11/2001 | Herman | |
| 2002/0031830 A1 * | 3/2002 | Smith et al. | 435/456 |
| 2004/0017018 A1 * | 1/2004 | Pommersheim | 264/4.3 |
| 2004/0048358 A1 * | 3/2004 | Walsh et al. | 435/283.1 |
| 2005/0266548 A1 * | 12/2005 | Herman et al. | 435/289.1 |
| 2005/0287670 A1 * | 12/2005 | Gulliver et al. | 435/455 |
| 2006/0188490 A1 * | 8/2006 | Hoerr et al. | 424/93.21 |
| 2007/0095393 A1 | 5/2007 | Zucchelli et al. | |
| 2009/0075801 A1 | 3/2009 | Hodko et al. | |
| 2011/0207222 A1 | 8/2011 | Mehta et al. | |

FOREIGN PATENT DOCUMENTS

| | | |
|---|---|---|
| JP | 61-005390 A | 1/1986 |
| JP | 62-116736 A | 5/1987 |
| JP | 11-143058 A | 5/1999 |
| JP | 2000-093844 A | 4/2000 |
| JP | 2000-210539 A | 8/2000 |
| JP | 2002-515239 A | 5/2002 |
| JP | 2005-534318 A | 11/2005 |
| WO | WO 99/60093 A2 | 11/1999 |
| WO | WO 2004/013204 A2 | 2/2004 |

OTHER PUBLICATIONS

International Preliminary Report on Patentability corresponding to International Application No. PCT/US2009/004113; Date of Mailing: Jan. 27, 2011; 11 pages.
International Search Report for International Application No. PCT/US2009/004113, dated Jul. 9, 2010 (6 pages).
Written Opinion of the International Searching Application No. PCT/US2009/004113, dated Jul. 9, 2010 (10 pages).
Japanese Office Action Corresponding to Japanese Patent Application No. 2011-518729; Dispatch Date: May 31, 2013; English Translation, 4 Pages.
International Search Report for International Application No. PCT/US2009/004137, dated Jul. 2, 2010 (6 pages).
Written Opinion of the International Searching Application No. PCT/US2009/004137, dated Jul. 2, 2010 (9 pages).
International Preliminary Report on Patentability corresponding to International Application No. PCT/US2009/004137; Date of Mailing: Jan. 27, 2011; 10 pages.
Office Action dated Oct. 31, 2014 regarding U.S. Appl. No. 13/054,292.
Japanese Office Action Corresponding to Japanese Patent Application No. 2011-518729; Dispatch Date: Jul. 4, 2014.

* cited by examiner

*Primary Examiner* — Christopher M Babic
*Assistant Examiner* — Kimberly A Aron
(74) *Attorney, Agent, or Firm* — Myers Bigel Sibley & Sajovec, P.A.

(57) ABSTRACT

The present invention comprises methods and systems for manipulation of media and particles, whether inert materials or biomaterials, such as cells in suspension cell culture. The methods and systems comprise use of an apparatus comprising a rotating chamber wherein the actions of the combined forces fluid flow force and centrifugal force form a fluidized bed within the rotating chamber.

12 Claims, 36 Drawing Sheets

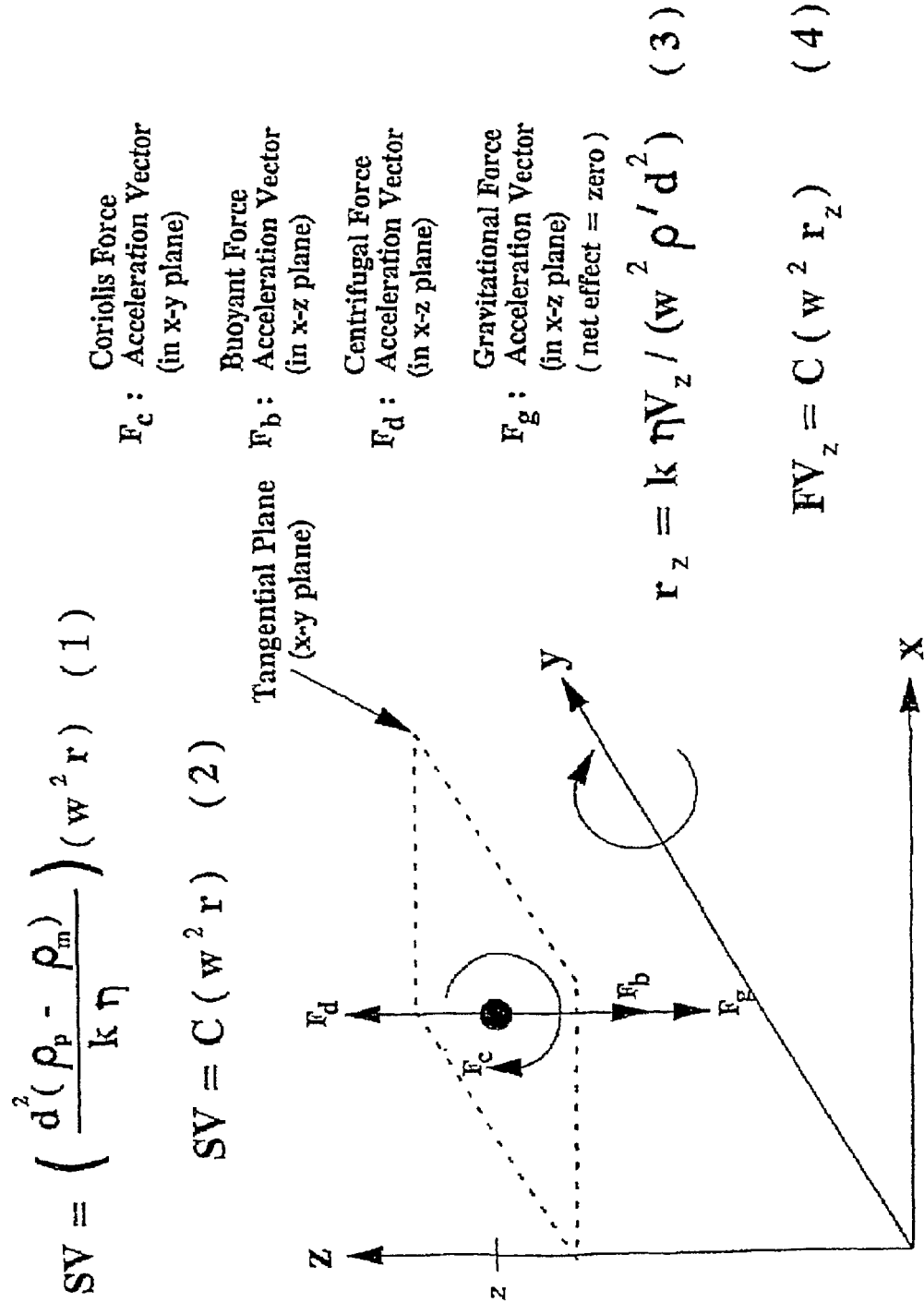

Figure 4

$$SV = \left(\frac{d^2(\rho_p - \rho_m)}{k\eta}\right)(w^2 r) \quad (1)$$

$$SV = C(w^2 r) \quad (2)$$

$F_c$: Coriolis Force Acceleration Vector (in x-y plane)

$F_b$: Buoyant Force Acceleration Vector (in x-z plane)

$F_d$: Centrifugal Force Acceleration Vector (in x-z plane)

$F_g$: Gravitational Force Acceleration Vector (in x-z plane) (net effect = zero)

$$r_z = k\eta V_z / (w^2 \rho' d^2) \quad (3)$$

$$FV_z = C(w^2 r_z) \quad (4)$$

Figure 7
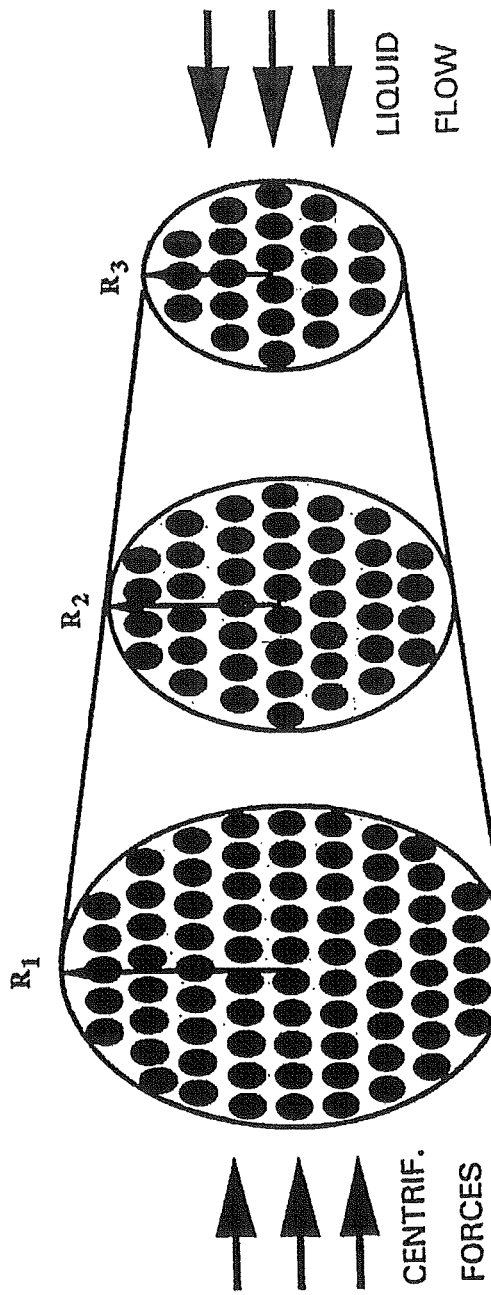
$$\text{Flow Velocity} = \frac{\text{Flow Rate}}{\Upsilon \times R_x^2} \quad (1)$$
$$\text{Relative Centrifugal Force} = w^2 R_{C_x} \quad (2)$$
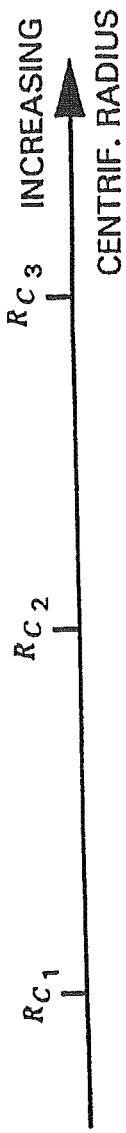

Continuous Flow Centrifuge Flow Diagram
Cell Capture Mode

Continuous Flow Centrifuge Flow Diagram

Cell Harvest Mode

Media / Buffer Exchange Flow Diagram
Cell Separation Mode

Media / Buffer Exchange Flow Diagram
Media / Buffer Exchange Mode

Cell Dispenser Flow Diagram
Cell Capture Mode

Cell Dispenser Flow Diagram
Dispense Mode

Transfection Flow Diagram
Cell Capture Mode

Transfection Flow Diagram
Transfection Mode

Transfection Flow Diagram
Cell Return Mode

Cell Separator Flow Diagram
Large Cell Capture Mode

Cell Separator Flow Diagram
Large Cell Harvest Mode

METHODS AND SYSTEMS FOR MANIPULATING PARTICLES USING A FLUIDIZED BED

RELATED APPLICATIONS

The present application is a 35 U.S.C. §371 national phase application of PCT International Application No. PCT/US2009/004113, filed Jul. 16, 2009, which claims priority from U.S. Provisional Patent Application No. 61/081,171, filed Jul. 16, 2008, and from U.S. Provisional Patent Application No. 61/170,584, filed Apr. 17, 2009, the disclosures of which are hereby incorporated herein by reference in their entireties. The above PCT International Application was published in the English language and has International Publication No. WO 2010/008563.

FIELD OF THE INVENTION

The present invention is related to methods, and systems that are used for transferring and manipulating particles, including biomaterials, such as cells, cellular components, proteins, lipids, carbohydrates and tissues, and formulations including particles using a fluidized bed.

BACKGROUND

Currently, there are hundreds of biotechnology medicines in the development pipelines of pharmaceutical and biotechnology companies, and the numbers are predicted to increase in time. To produce such biotechnological products, large numbers of prokaryotic and eukaryotic cells are grown in fermentation systems. Prokaryotic cells, for example, bacterial cells, are physically more resilient than eukaryotic cells. Eukaryotic cells, such as mammalian cells, are more fragile and are more affected by steps in the culturing process such as centrifugation, pelleting or re-suspension which are necessary manipulations of the cells for biomanufacturing purposes.

Generally, cells are grown in large stainless-steel fermentation vats under strictly maintained and regulated conditions. The cells may be the product itself, or the cells may produce a product of interest. With either goal, the production of cellular based products is a complicated process. The cells are grown in carefully controlled culture conditions which include a balance of temperature, oxygen, acidity, and removal of waste products or an excreted product of interest. The growth and activity of the cells can be interfered with by even slightly altering the culture conditions, and can be highly inhibited by actions such as removal of media, isolation of the cells by spinning out the cells and packing them in a pellet formed by centrifugation, and resuspension of a packed pellet to reintroduce the cells into the culture conditions.

Many known cell culture methods require significant investment in capital and labor. Cell culture facilities cost millions of dollars to build and take several years. There are a limited number of existing facilities that can be used to produce the products that are currently proposed. Cell culture is currently used for production of proteins such as human insulin, vaccine proteins, enzymes for food processing, biodegradable plastics, and laundry detergent enzymes. Such products include, but are not limited to, therapeutic molecules, vaccines, and antibodies that function as diagnostic tools, therapeutic compounds, in protein-chips or biosensors.

A growing concern in biomanufacturing is recognition of the extent of materials used for production of cellular products, or how green is the technology. This concern looks at the type and amount of resources required to make therapeutic proteins and other cell culture products, and the wastes generated by mammalian cell culture and microbial fermentation processes. Manufacturing such products is relatively environmentally friendly compared with the production of small-molecule drugs and commodity petroleum-derived chemicals. However, the processes of cell culture use a lot of water, for example, in batch reactors that hold thousands of liters of culture or fermentation broth. Additionally, even more water, along with consumable processing aids, such as tubing, filters and chromatography processes, are used for downstream purification. Calculations have shown that for biologics, a current large-scale cell culture process to make a kilogram of monoclonal antibody requires more than 7,600 kg of material, divided as 7,000 kg of water, 600 kg of inorganic salts and buffers, which end up in the aqueous waste at the end of the process, 8 kg of organic solvents and 4 kg of consumables. For microbial fermentation, 15,500 kg of material is needed for 1 kg of product, with 15,000 kg being water. Using disposable equipment may add to the waste stream, whereas using reusable materials adds to the water usage.

What is needed are methods and systems that can be used in biomanufacturing systems and other types of processes that can be used with particles. The particles can be living or inert, including biomaterials and all types of cells, hardy cells and cells that require gentle treatment. What is also needed are methods and systems that do not disrupt cellular growth and activity processes during the biomanufacturing processes, and may aid in the growth and production of cells. Additionally, it would be beneficial for methods and systems to provide green technology advances to the biomanufacturing process. Methods and systems for the transfer and manipulation of particles in efficient methods are also needed.

SUMMARY

The methods and systems disclosed herein comprise methods and systems for manipulating particles including inert particles and cells or biomaterials such as cellular components, proteins, carbohydrates, lipids, and tissues. In one embodiment, the methods and systems of the present invention may be used in processes where particles are involved, such as biomanufacturing applications, or for use with suspension cell cultures, such as in transfecting cells using transfection methods. For example, the methods and systems disclosed herein can be used for perfusion bioreactor processes and for cell concentration in suspension cell culture methods. The methods and systems disclosed herein may be used in coating applications, cell or biomaterial selection, or isolation and/or purification of selected biomaterials, such as cells. An apparatus of the methods and systems disclosed herein can function as a continuous flow centrifuge to concentrate cells without the need to remove the cells from the current media, does not subject the cells to the shear forces found in traditional centrifugation, does not pack or pellet the cells, and avoids the trauma of those actions on living cells. The methods and systems disclosed herein may be used for inert or nonliving particles and biological particles such as cells.

In another embodiment, the methods and system of the present invention can be used to transfer cells from one location, such as a bioreactor, to another location, such as a chamber of a disclosed apparatus, with minimal disturbance to the cells. This capability of moving the cells allows for a change of media or alteration of the environment of the cells without disturbing the cells, so that the growth and activity of the cells is unimpeded. If the aim of the method is to quickly change the environment of the cells or to affect the growth or activity of the cells, the methods and systems disclosed herein provide for a rapid change to the cells, without having to centrifuge and pellet the cells to remove the first environment and resuspend the cells in the new environment.

In another embodiment, the methods and systems of the present invention can be useful in transfection processes, or other processes that are designed to affect the cells individually, such as viral infection. For example, the efficiency of transfection of cells in suspension can be aided by the methods and systems disclosed herein. In another example, cells may undergo electroporation techniques. The cells, or a particular subset of the cells, can be removed from the bioreactor container to a chamber of an apparatus and there be affected, such as by transfection or infection techniques. The cells may be affected by particular chemicals, stimulants, inhibitors, or other factors that alter the cells' activities or growth.

In another embodiment, the methods and systems of the present invention can be used to separate cellular subpopulations from a mixed cellular population. For example, cells can be separated based on affinity, density or size. The methods and systems disclosed herein may be used to separate cellular components or biomaterials including, but not limited to, proteins, carbohydrates or lipids. For example, a mixture of proteins can enter a rotating chamber of an apparatus and media conditions can be such that a selected population of proteins precipitates. Such precipitates form a fluidized bed in the rotating chamber and are contained within the chamber, and may be removed by changing the rotation conditions and/or the media flow force. Nonprecipitated proteins are not contained in the fluidized bed and flow through the rotating chamber. In one aspect, the methods and systems disclosed herein may be used to provide scaffolding materials to cells or to remove cells from scaffolds, such as cells associated with tissue. In another aspect, the methods and systems disclosed herein can be used to selectively remove subpopulations of cells from a stationary or growing population of cells. In still another aspect, the methods and systems disclosed herein can conserve media resources.

The methods and systems of the present invention comprise an apparatus comprising a rotor that rotates about an axis. In some embodiments, the rotor can rotate about a horizontal axis. In some other embodiments, the rotor can rotate about a vertical axis. In still other embodiments, the rotor can rotate about any axis between a horizontal axis and a vertical axis.

According to some embodiments of the present invention, a method for manipulating cells using a fluidized bed includes: rotating a chamber including an inlet and an outlet about an axis to create a centrifugal force field; flowing a first stream containing a first media and cells into the chamber through the inlet, wherein flowing the first stream acts to create a force which opposes the centrifugal force; forming a fluidized bed of cells in the chamber, wherein the forces substantially immobilize the cells in the fluidized bed by the summation of vector forces acting on the cells; collecting the first media substantially without cells passing through the outlet of the chamber; then manipulating the cells in the fluidized bed, wherein said manipulating is selected from the group consisting of removing, concentrating, diluting, exchanging media, harvesting, transferring, dispensing, transfecting, electroporating, separating, isolating, extracting, selecting, purifying, coating, binding, physically modifying, and altering the environment; and thereafter removing the cells from the fluidized bed. Removing the cells from the fluidized bed includes: flowing a second stream into the chamber through the outlet, wherein flowing the second stream acts to create a force at least partially in the same direction as the centrifugal force field; and collecting the cells passing through the inlet of the chamber.

In some further embodiments, the method includes: providing the first stream from a cell culture system prior to flowing the first stream into the chamber, providing perfusion cell culture conditions to the fluidized bed of cells; exchanging the media; and delivering the cells and exchanged media to the cell culture system after removing the cells from the fluidized bed.

In some embodiments, manipulating the cells includes transfecting, wherein transfecting includes circulating a transfection stream containing a transfection reagent complex through the fluidized bed of cells one or more times.

In some embodiments, manipulating the cells includes electroporating, wherein electroporating includes: applying an electric current to the fluidized bed of cells; and altering the permeability of the cells. In some other embodiments, electroporating further includes: flowing a charged molecule stream containing charged molecules into the chamber through the inlet before, concurrently with, and/or after applying the electric current; and incorporating the charged molecules into the cells.

According to some embodiments of the present invention, a method for manipulating particles using a fluidized bed includes: rotating a chamber including an inlet and an outlet about an axis to create a centrifugal force field; flowing a first stream containing a first media and particles into the chamber through the inlet, wherein flowing the first stream acts to create a force which opposes the centrifugal force; forming a fluidized bed of particles in the chamber, wherein the forces substantially immobilize the particles in the fluidized bed by the summation of vector forces acting on the particles; collecting the first media substantially without particles passing through the outlet of the chamber; then manipulating the particles in the fluidized bed, wherein said manipulating is selected from the group consisting of removing, concentrating, diluting, exchanging media, harvesting, transferring, dispensing, separating, isolating, extracting, selecting, purifying, coating, binding, physically modifying, and altering the environment; and thereafter removing the particles from the fluidized bed. Removing the particles comprises from the fluidized bed includes: flowing a second stream into the chamber through the outlet, wherein flowing the second stream acts to create a force at least partially in the same direction as the centrifugal force field; and collecting the particles passing through the inlet of the chamber.

In some embodiments, manipulating the particles includes concentrating the particles, wherein concentrating the particles comprises receiving the particles in a concentrated particles harvest container after removing the particles.

In some embodiments, manipulating the particles includes exchanging the media, wherein exchanging the media includes: flowing a new media stream comprising a second media into the chamber through the inlet; and replacing at least some of the first media in the fluidized bed with the second media.

In some embodiments, manipulating the particles includes harvesting, wherein harvesting includes receiving the particles in a particle harvest container after removing the particles.

In some embodiments, manipulating the particles includes dispensing, wherein dispensing includes receiving a measured amount of particles in one or more dispensed cell containers after removing the particles.

In some other embodiments, the particles include a mixed population of particles, wherein manipulating the particles includes separating, wherein separating comprises: removing at least some of the particles from the fluidized bed; and collecting the at least some of the particles passing through the outlet of the chamber. In some further embodiments, removing at least some of the particles includes altering the centrifugal force field and/or the force of the first stream. In still further embodiments, the particles are separated by size, density, and/or shape.

In some embodiments, manipulating the particles includes coating the particles, wherein coating the particles includes: flowing a coating stream containing a coating material into the chamber through the inlet; and coating the particles retained in the fluidized bed with the coating material.

According to some embodiments of the present invention, a method for separating a mixed population of particles includes: rotating a chamber including an inlet and an outlet about an axis; substantially immobilizing an affinity matrix in the chamber; flowing a first stream containing a first media and a mixed population of particles comprising target particles and non-target particles into the chamber through the inlet; retaining target particles in the affinity matrix in the chamber; and collecting the first media and non-target particles passing through the outlet of the chamber. In some further embodiments, the method includes: flowing a second stream containing an elution media into the chamber through the inlet; releasing the target particles from the affinity matrix; and collecting the target particles passing through the outlet of the chamber.

According to some embodiments of the present invention, a method for fractionating biomaterials includes: rotating a chamber including an inlet and an outlet about an axis to create a centrifugal force field; flowing a first stream containing a first media and a mixture of biomaterials into the chamber through the inlet, wherein flowing the first stream acts to create a force which opposes the centrifugal force; selectively precipitating biomaterials from the first stream; forming a fluidized bed of the precipitated biomaterials in the chamber, wherein the forces substantially immobilize the precipitated biomaterials in the fluidized bed by the summation of vector forces acting on the precipitated biomaterials; then collecting the first media and the non-precipitated biomaterials passing through the outlet of the chamber; and thereafter removing the precipitated biomaterials from the fluidized bed. Removing the precipitated biomaterials from the fluidized bed includes: flowing a second stream into the chamber through the outlet, wherein flowing the second stream acts to create a force at least partially in the same direction as the centrifugal force field; and collecting the precipitated biomaterials passing through the inlet of the chamber. In some further embodiments, the biomaterial is protein.

According to some embodiments of the present invention, a method for associating particles with scaffolding material includes: rotating a chamber including an inlet and an outlet about an axis to create a centrifugal force field; flowing a first stream containing a first media and scaffolding material into the chamber through the inlet, wherein flowing the first stream acts to create a force which opposes the centrifugal force; forming a fluidized bed of the scaffolding material in the chamber, wherein the forces substantially immobilize the scaffolding material in the fluidized bed by the summation of vector forces acting on the scaffolding material; flowing a second stream containing a second media and particles into the chamber through the inlet, and retaining at least some of the particles with the scaffolding material.

According to some embodiments of the present invention, a method for removing particles from scaffolding material includes: rotating a chamber including an inlet and an outlet about an axis to create a centrifugal force field; flowing a first stream containing a first media and scaffolding material comprising particles into the chamber through the inlet, wherein flowing the first stream acts to create a force which opposes the centrifugal force; forming a fluidized bed of the scaffolding material in the chamber, wherein the forces substantially immobilize the scaffolding material in the fluidized bed by the summation of vector forces acting on the scaffolding material; flowing a second stream containing a dissociation reagent into the chamber through the inlet; removing particles from the scaffolding material; and collecting the removed particles passing through the outlet of the chamber.

According to some embodiments of the present invention, a system for manipulating particles, includes: a chamber rotatable about an axis to create a centrifugal force field, the chamber having an inlet and an outlet; a bioreactor containing a first fluid and particles; at least one pump in fluid communication with the rotating chamber and the bioreactor; a fluid manifold in fluid communication with the rotating chamber, wherein the manifold includes a plurality of spaced apart valves that are automatically selectively closed and opened during use; a controller in communication with the at least one pump and the valves, wherein the controller directs: (i) the valves to open and close, (ii) the flow rates of the at least one pump, (iii) the rotational speed of the rotating chamber, and (iv) a flow velocity of a first stream containing the first fluid and particles from the bioreactor into the chamber through the inlet, wherein in operation, the flow velocity of the first stream from the bioreactor into the chamber through the inlet acts to create a force which opposes the centrifugal force, thereby forming a fluidized bed of particles in the chamber, wherein the forces substantially immobilize the particles in the fluidized bed by the summation of vector forces acting on the particles. In some further embodiments, the controller further directs a flow velocity of a second stream containing a second fluid from a fluid source into the chamber through the outlet, wherein in operation, the flow velocity of the second stream from the second fluid source into the chamber through the outlet acts to create a force at least partially in the same direction as the centrifugal force field, thereby removing the particles from the fluidized bed. In some further embodiments, in operation, the particles are collected through the inlet of the chamber and returned to the bioreactor after being removed from the fluidized bed. In still further embodiments, the at least one pump includes a bi-directional pump.

According to some embodiments of the present invention, a system for manipulating particles, includes: a chamber comprising spaced apart inlet and outlet ports sized and configured to apply a centrifugal force and an opposing fluid flow force to particles therein; a primary pump in fluid communication with the chamber and a fluid source; a fluid manifold in fluid communication with the chamber, wherein the manifold includes a plurality of spaced apart valves that are automatically selectively closed and opened during use; a fluid buffer wash source in communication with the manifold; a secondary pump in fluid communication with the fluid buffer wash source and the manifold, wherein the secondary pump has active on and off periods, and wherein in an active on period, the secondary pump has a higher flow rate than the primary pump, wherein the secondary pump resides proximate the fluid buffer wash source attached to a first arm of the manifold, and wherein a second arm of the manifold has opposing first and second end portions arranged so that the second arm extends around the secondary pump with the first end portion attached above the secondary pump and the second end portion attached to the first arm below the secondary pump, and wherein the second arm includes a first one of the valves; and a controller in communication with the primary pump, the secondary pump and the valves, wherein the controller directs: (i) the opening and closing of the valves, (ii) the flow rates of the primary and secondary pumps, (iii) the rotational speed of the chamber to create a centrifugal force of between about 25-15,000×g, (iv) an average flow velocity of the fluid from the fluid source through the chamber at between about 20-300 mm/min, wherein in operation, the system has a wash cycle that flushes defined segments of the manifold with buffer from the buffer wash source after initial loading of the rotating chamber with target media to thereby cleanse dead legs in the manifold.

In some further embodiments, the manifold includes an input flow path that extends between the chamber and a bioreactor, the input flow path having a bioreactor valve positioned proximate the bioreactor, and the first arm of the manifold merges into the input flow path upstream of the bioreactor valve and includes two serially spaced apart valves therebetween, such that, in the buffer wash cycle, the two serially spaced apart valves and the bioreactor valve are open when the secondary pump is on and the first valve in the second arm is closed, so that a dead leg at the bioreactor valve is flushed. In some further embodiments, the manifold includes a second flow path that extends between the chamber and the first arm of the manifold with a waste line extending to a waste container upstream of the second arm of the manifold with a waste valve in the waste line, the second flow path including a second flow path valve that resides upstream of the second arm of the manifold, wherein, in the buffer wash cycle, after the dead leg at the bioreactor is flushed, the bioreactor valve is closed, and the second flow path valve is open to flush a dead leg associated with the secondary flow path valve. In still further embodiments, the system includes a third arm of the manifold in communication with the bioreactor, the third arm of the manifold including a valve. In some embodiments of the foregoing systems, the particles are cells.

In some embodiments of the foregoing methods and systems, the axis is a substantially horizontal axis. In some other embodiments of the foregoing methods and systems, the axis is a substantially vertical axis.

DESCRIPTION OF FIGURES

FIG. 4 is a mathematical evaluation of the immobilization of conditions at a given radius.

FIG. 7 is an illustration of a three-dimensional array of particles in a rotating conical chamber.

DETAILED DESCRIPTION

Figure 1:
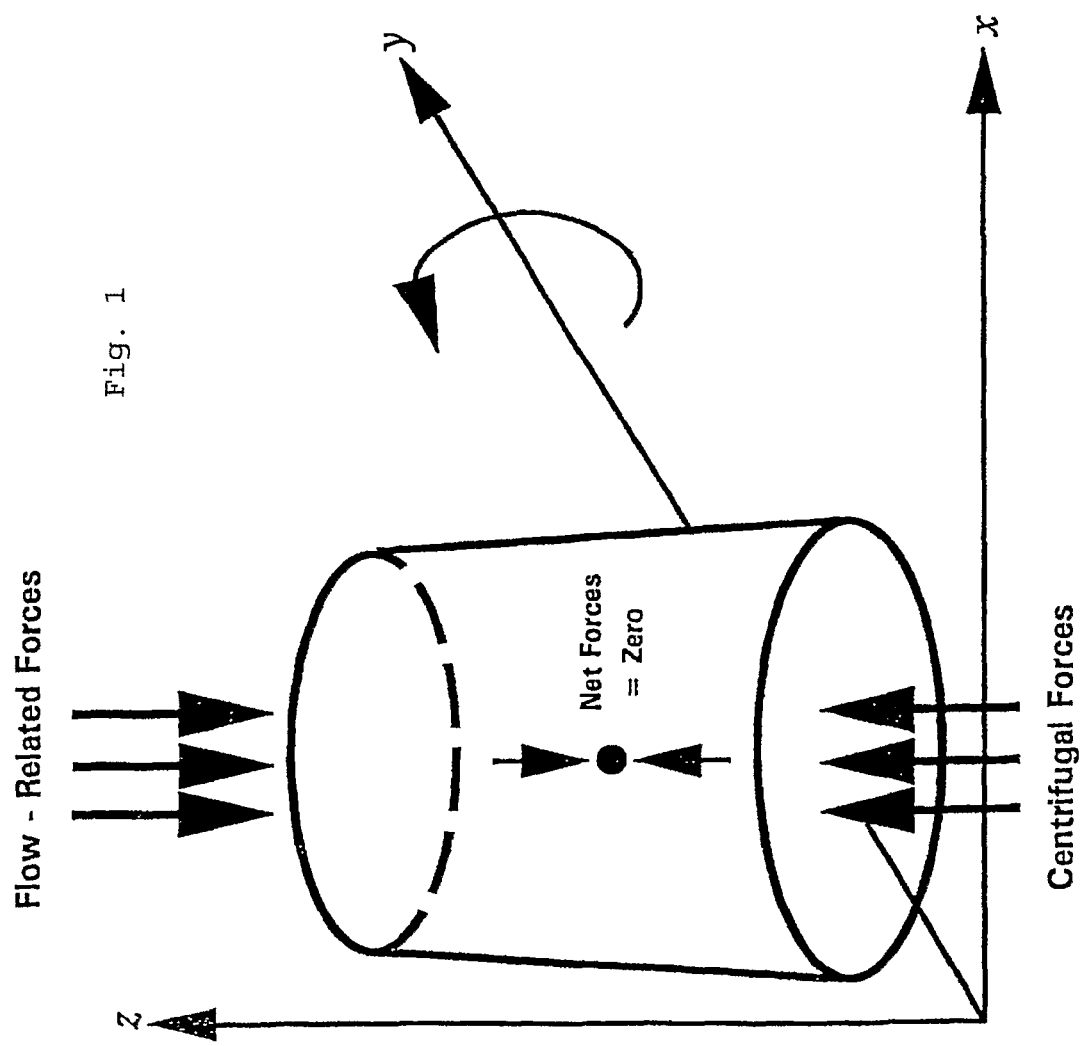
FIG. 1 illustrates forces involved in the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

As used herein, the term "particles" includes inert and living materials, and includes, but is not limited to, cells, cellular organelles, enzymes, biomolecules such as proteins, lipids, carbohydrates, inert materials such as polymeric or copolymeric materials that are nano or microparticles and other types of nano or microparticles.

As used herein, the term "cell culture system" refers to any system or apparatus in which cells are grown, including, without limitation, mammalian, avian, insect, fungal, and bacterial cells. In one embodiment, a cell culture system refers to a system in which cells are grown in suspension.

As used herein, the term "substantially without particles" refers to an amount of particles that is less than 20% of the total amount of particles in the chamber, e.g., less than 15, 10, 5, or 1%.

As used herein, the term "substantially horizontal" refers to an axis that is within about 20 degrees of horizontal, e.g., within about 15, 10, 5, or 1 degree of horizontal.

As used herein, the term "substantially immobilized" means that the particles may move to a small extent within the chamber but do not exit the chamber.

As used herein, the term "fluid" includes liquids and gases.

As used herein, the term "biomaterials" refers to materials that are part of a cell or other living structure, e.g., proteins, peptides, nucleic acids, lipids, carbohydrates, membranes, organelles, etc.

As used herein, the term "physically modifying" refers to the physical alteration of a particle (e.g., cell), e.g., a change in physical and/or chemical structure, covalent binding to another molecule, incorporation of a molecule within the particle, etc.

As used herein, the term "altering the environment" refers to a change in the milieu surrounding the particle, e.g., a change in media, addition of one or more compounds to the media, a change in the concentration of a compound within the media, etc.

The methods and systems disclosed herein comprise methods and systems for the manipulation of particles, such as inert particles or living particles, such as cells in cell culture, using a fluidized bed. Useful applications of the methods and systems include, but are not limited to, movement of particles (e.g., cells, either prokaryotic or eukaryotic) from one location to another, concentrating or diluting of particles (e.g., cells), such as increasing or decreasing the number of cells/mL, changing of media conditions, performing actions on the particles (e.g., cells) or changing the environment of the particles (e.g., cells), such as transfecting the cells or providing specific chemical activators or inhibitors to the cells, and providing a controlled measured dispensing of particles or cells into other vessels, such as into vials or other containers.

In some embodiments of the present invention, the methods and systems disclosed herein may comprise an apparatus comprising a rotor that rotates in a plane substantially coaxial with the gravitational axis. The apparatus may be outfitted with components to allow for the flow of liquid media. The apparatus substantially immobilizes the particles that form a fluidized bed by use of the summation of the vector forces acting on each particle. Embodiments of such apparatus have been disclosed in U.S. Pat. Nos. 5,622,819; 5,821,116; 6,133,019; 6,214,617; 6,660,509; 6,703,217; 6,916,652; 6,942,804; 7,347,943; and U.S. patent application Ser. Nos. 12/055,159 and 11/178,556, each of which is incorporated by reference in its entirety. Though cells and particles are light in weight, their mass is non-zero. Consequently, gravity has a significant effect on the suspended particle or cell, and this effect will increase with time. The weight of the suspended particles or cells causes these particles to settle to the lowest regions of the container, disrupting the balance of forces which initially suspended them in the chamber. As is seen in prior art devices, particles tend to aggregate and the aggregation of these particles into a larger particle results in an increased centrifugal effect which causes the aggregates to migrate to longer radii, eventually causing destabilization of the fluidized bed.

According to these embodiments, an apparatus used in the methods and systems of the present invention take advantage of the relationships inherent in (1) Stoke's Law and the theory of counterflow centrifugation; (2) the geometrical relationships of flow velocity and centrifugal field strength; and, (3) the effect of hydraulic pressure on media and particles. The methods and systems comprise apparatus that are capable of forming a fluidized bed of particles by the immobilization of three-dimensional arrays of particles such as cells, by employing rotation around a horizontal axis and balancing forces including gravity, centrifugal force from the rotation and a liquid flow force provided by the media stream entering the chamber or container holding the particles.

The theoretical basis of the apparatus of the present invention utilizes a novel method to immobilize suspended particles. A proper application of Stoke's Law, in combination with provision for the effect of gravity, which acts on the immobilized suspended particles, results in a mathematical relationship which allows for the relative immobilization of such particles. The effect of gravity can be compensated for by the choice of rotational axis as is shown in FIG. 1. If rotation about the horizontal axis (y) is chosen instead of rotation about the vertical axis (z), as is most common in biological centrifugation apparatus and methods, then the effect of gravity on immobilized particles will be limited to action solely in the x-z plane. Since this is the same plane in which both the centrifugal as well as the liquid flow related forces are constrained to act, the motion of a suspended particle at any point in a rotational cycle is the resultant of the sum of the three types of forces acting upon it. Rotation about the horizontal axis means that the suspended particle is rotating substantially coaxial with the gravitational force axis.

Figure 2:
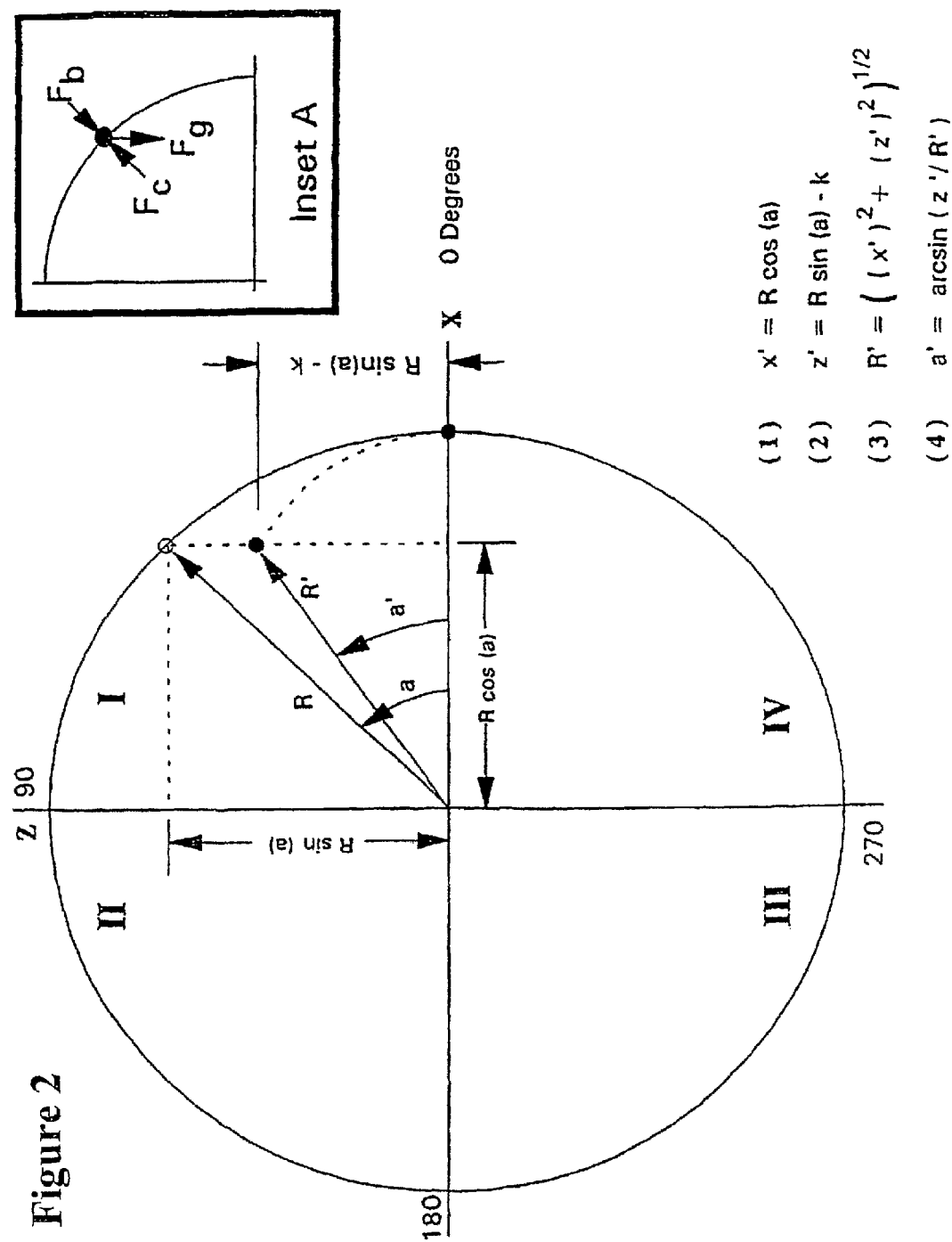
FIG. 2 is an illustration of the mathematics governing the motion of a particle due to the effect of gravity on that particle when it is restrained in a centrifugal field that is opposed by liquid flow.

As is shown in Inset A of FIG. 2, where the plane of the Figure is the x-z plane, the effect of gravity (Fg) on the position of a particle suspended in a radially-directed centrifugal field (Fc) while an exactly equal and opposing force supplied by an inwardly-directed flowing liquid (Fb) is directed toward the particle, can be calculated by the evaluation of equations 1-4 where (k) represents the downward displacement in the x-z plane imparted by gravitational forces during an angular rotation of the rotor position equal to (a). Analysis of the motion of a particle under these constraints and for $[2\pi x(k/a)] < R$ (a low mass particle) results in the determination that the motion is periodic; that is, the particle motion results in a return to its starting place after a complete rotation of 360 degrees (after equilibrium is reached). As is shown in FIG. 2, the effect of gravity on the motion of a particle which is otherwise immobile as a result of the opposing equality of the centrifugal and flow-related forces results in a decrease in radial position in quadrants I and II, and an exactly equal radial lengthening in quadrants III and IV. Thus, the radial distance of the particle from the axis of rotation also exhibits a periodic motion over the course of a full rotation of 360 degrees. It should be noted that, mathematically, measurement of the periodicity of motion requires only one rotation if measurement begins at either 90 or 180 degrees whereas two full rotations are required if measurement begins at either zero or 180 degrees, since a new equilibrium radial distance different from the original results in the latter case.

Figure 3:
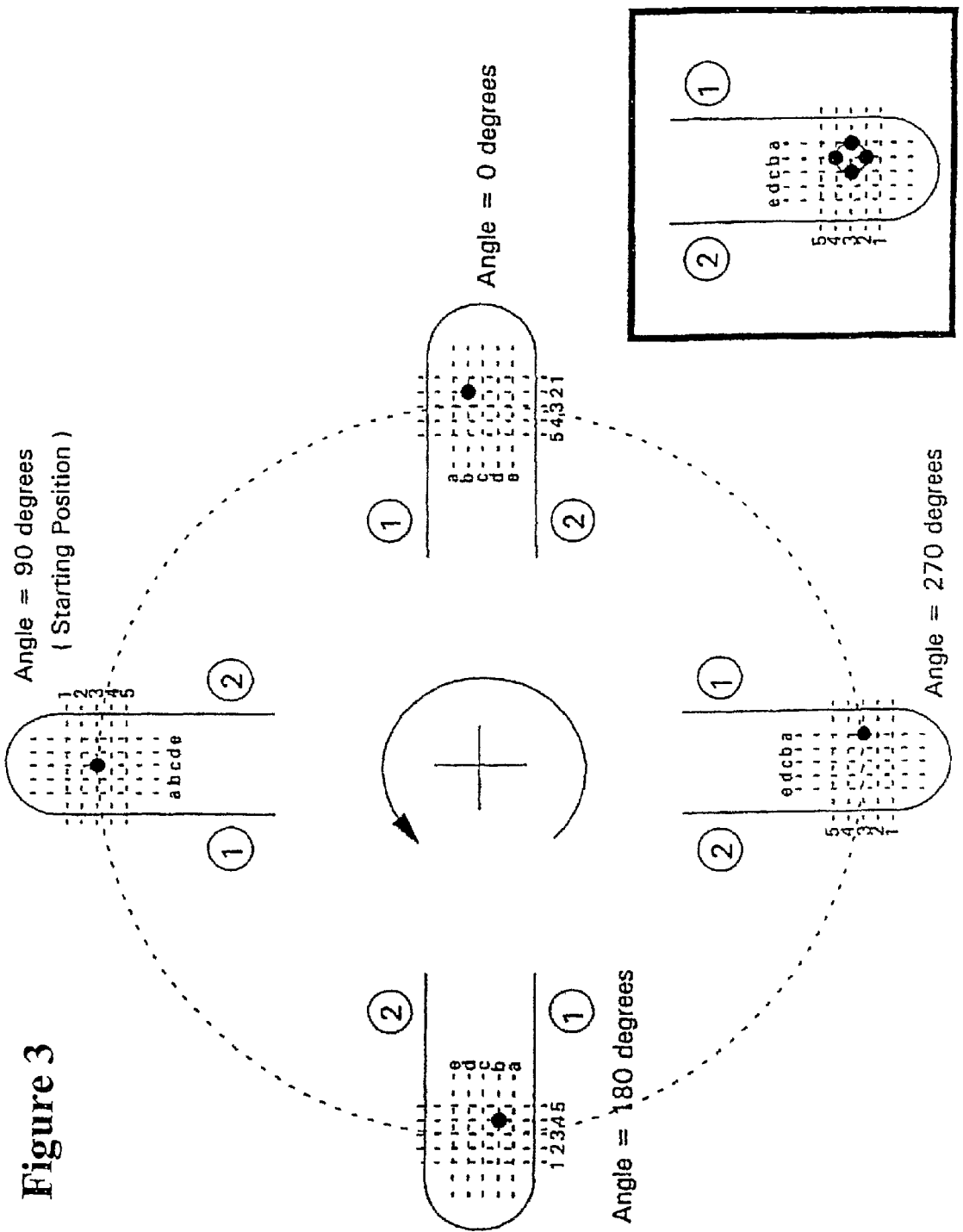
FIG. 3 is an illustration of the resultant motion of a particle under the constraints of FIG. 2.

The effective motion of a particle through a complete rotational cycle is shown in the inset of FIG. 3. If the sides of a container in which the particle is suspended are labeled 1 and 2, then the motion of the particle over the course of one rotational cycle would describe a circle with its center displaced toward the "leading edge" side of the particle's container. Thus, a particle suspended in a centrifugal field which is opposed by an equal liquid flow field will be constrained to periodic motion (and thus is effectively immobilized) if the balance of the radially-directed forces can be maintained over the course of its movement.

A graphical representation is shown in FIG. 4, in which the axis of rotation is now the (y) axis. Under these conditions the hypothesis of Sanderson and Bird can now be restated and applied to immobilization of particles. There is a radial distance along the z axis (rz) which, when evaluated by Eqn. 3, represents a position in which the particle is relatively immobilized in a centrifugal field which is exactly opposed by an inwardly-directed liquid flow, even in the presence of a gravitational field. Furthermore, a simplification of Stoke's Law (Eqn. 1) under the conditions of uniform particle size, shape, and density and a homogeneous liquid flow results in Eqn. 2, where it is obvious that the Sedimentation Velocity of a particle (SV) is a simple linear function of the applied centrifugal field. Similarly, Eqn. 3 can then be rewritten under the same conditions to yield Eqn. 4, where liquid Velocity (V in Eqn. 3) has been replaced by liquid Flow Velocity (FV). Equation 4 suggests that there is a continuum of liquid flow velocities and applied centrifugal fields which could be matched by the evaluation of constant (C), all of which would satisfy the requirement of relative particle immobilization. Further, if the liquid flow velocity could be varied as a function of (z), there could be a separate application of this equation at each radial distance. Consideration of the implications of Eqn. 4 is important for the relative immobilization of three-dimensional arrays of particles as opposed to the immobilization of two-dimensional arrays of particles at a single radial distance from the rotational axis.

Figure 5:
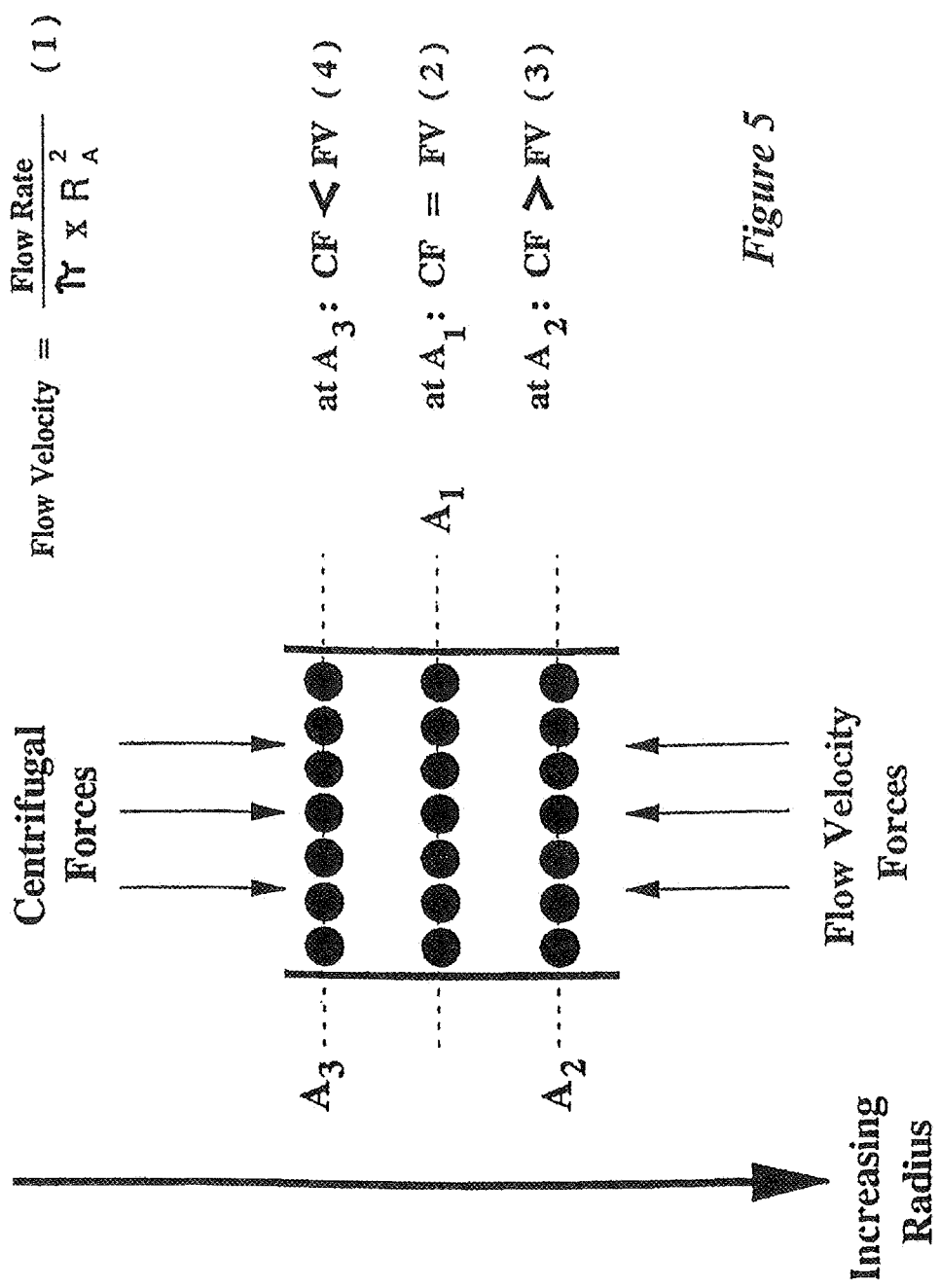
FIG. 5 is an analysis of the balance of centrifugal forces and flow velocity forces in a rotating cylindrical chamber.

If the chamber in which a particle is located is cylindrical (as is graphically depicted in FIG. 5) and if a liquid is flowed into this chamber from the end of the chamber most distal to the axis of rotation, then it is obvious that the flow velocity of this liquid flow (as defined in Eqn. 1, FIG. 5) will have a single value at all points not occupied by layers of particles. As a consequence, if a two-dimensional array of particles is in positional equilibrium at a particular radial distance (A1), as is indicated in Eqn. 2, (where CF is the centrifugal field strength and FV is the liquid flow velocity) then particles forced to occupy positions at radial distances either greater than or smaller than A1, such as those located in FIG. 5 at A2 or A3, will necessarily be presented with an inequality of restraining forces which will result in net translation of the particles. Thus, those particles located at A2, a longer radial distance than A1, will experience a greater centrifugal force than those at A1 and will necessarily migrate to longer radial distances (Eqn. 3). Conversely, particles initially located at A3 would experience a reduced centrifugal field and would migrate to shorter radial distances (Eqn. 4). Thus, it is believed that it is not possible to form a three-dimensional array of particles in a parallel-walled chamber such as that of FIG. 5.

Figure 6:
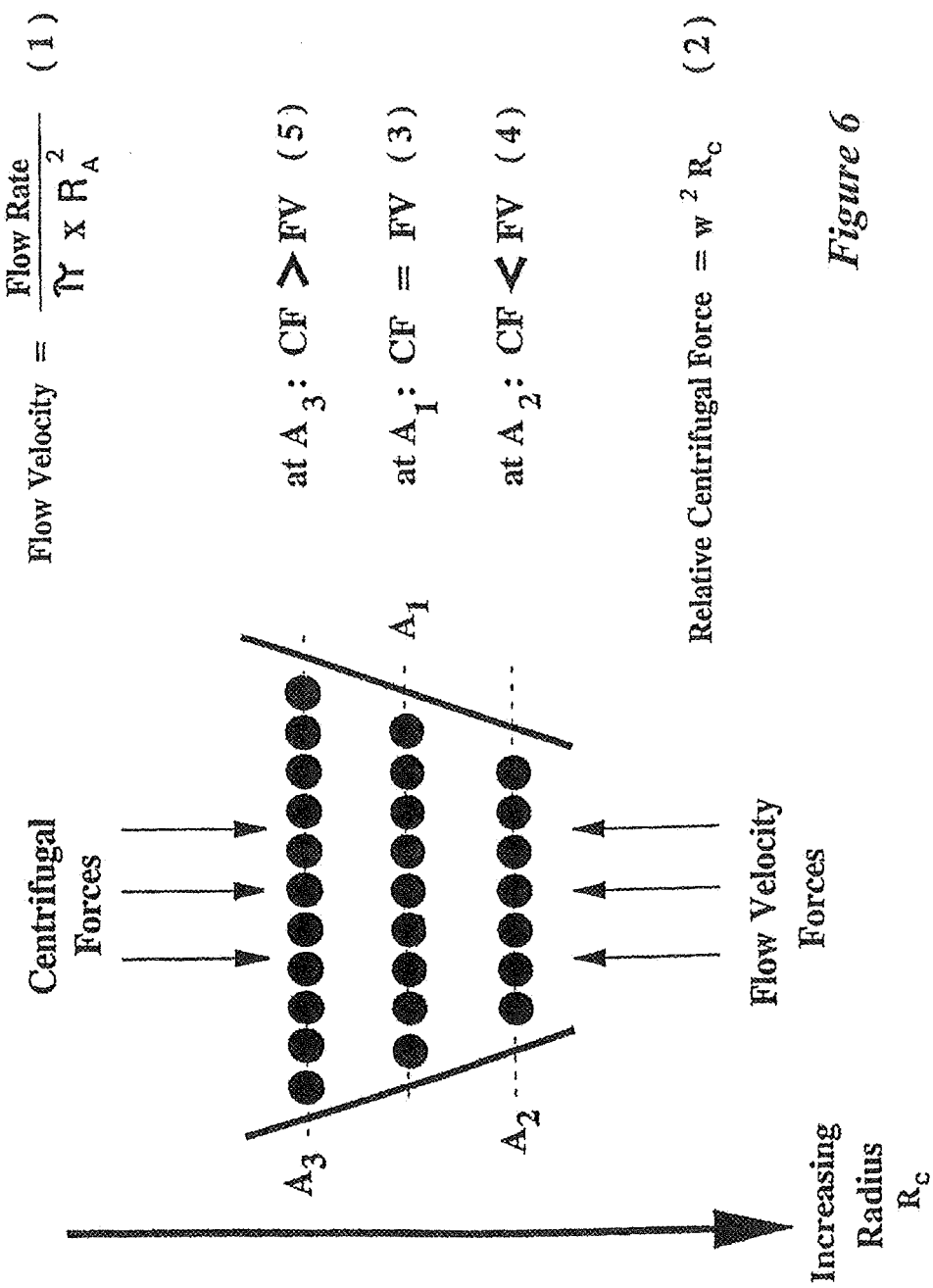
FIG. 6 is an analysis of the balance of centrifugal forces and flow velocity forces in a rotating conical chamber.

If, however, the chamber has a geometry such that its cross-sectional area increases as the rotational radius decreases, as is graphically displayed in FIG. 6, then it is possible to form three-dimensional arrays of immobilized particles, for example, cells. This is a consequence of the fact that the microscopic flow velocity of the liquid flow varies inversely as the cross-sectional area (Eqn. 1) while the relative centrifugal field varies directly as the rotational radius (Eqn. 2). Thus, if values of flow velocity and rotation velocity are chosen such that a two-dimensional array of particles is immobilized at rotational radius A1 (Eqn. 3), then it is possible to adjust the "aspect ratio" of the side walls of the chamber such that those particles initially located at radial distance A2 could also experience either an similar equality of forces or, as is shown in Eqn. 4, an inequality of forces which results in net motion back toward the center of the chamber. A similar argument may be applied to particles located at A3 (see Eqn. 5). Although the geometry of the chamber as depicted in FIG. 6 is that of a truncated cone, note that other geometries could be alternatively used—subject to the constraint that the cross-sectional area of the chamber increases as the rotational radius decreases. Thus, as is depicted in FIG. 7, it is possible to construct a three-dimensional array of particles in a varying centrifugal field opposed by a liquid flow field if the chamber geometry chosen allows for a flow velocity decrease greater than or equal to the centrifugal field strength decrease as the rotational radius decreases. In the geometry chosen in FIG. 7, that of a truncated cone, the two-dimensional arrays of particles at each rotational radius (Rc) will each be constrained to motion toward that radius where the opposing forces are exactly equal.

Figure 8:
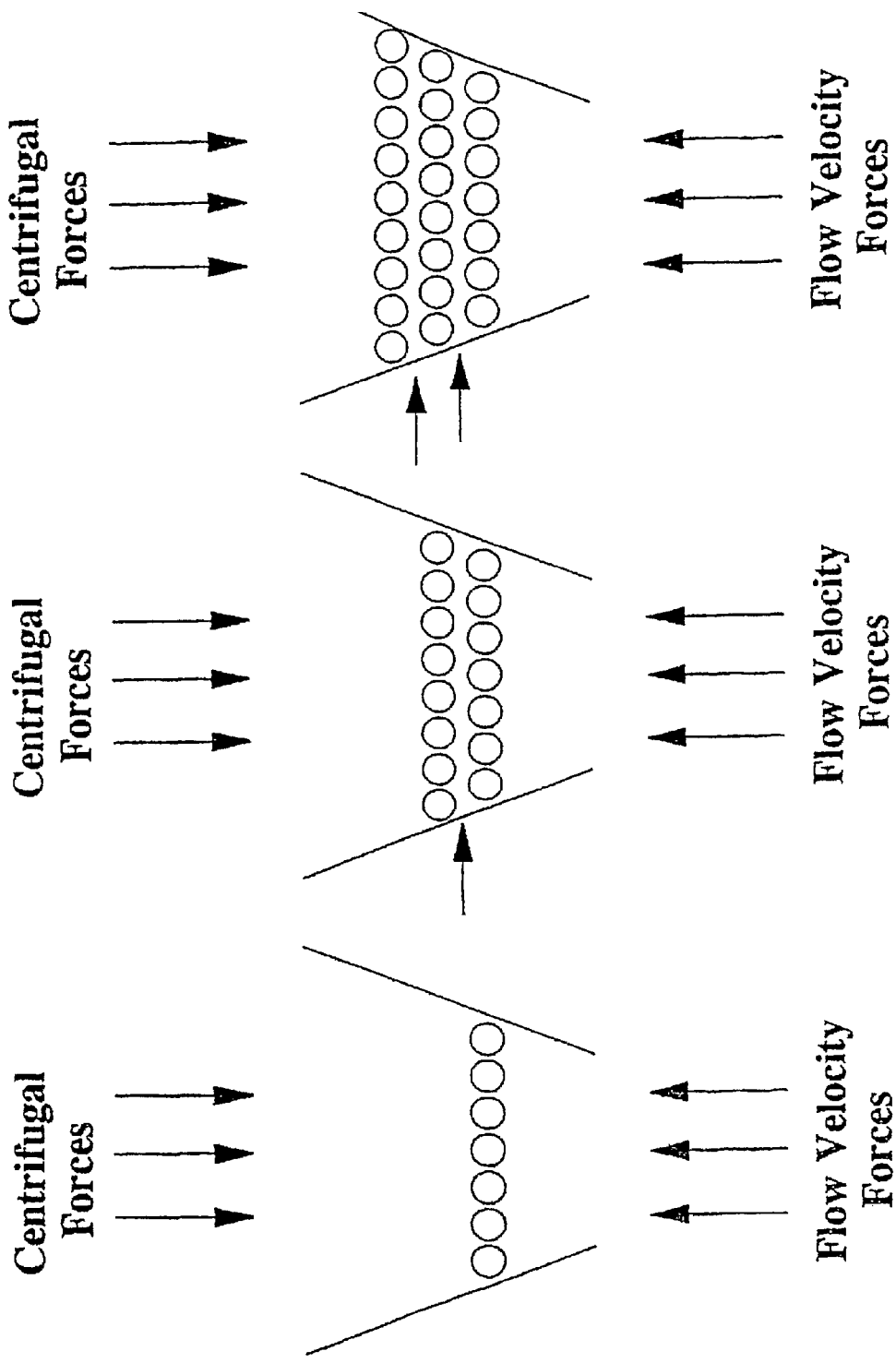
FIG. 8 is an illustration of the inter-stratum buffer regions in a three-dimensional array of particles in a rotating conical chamber.
Figure 9:
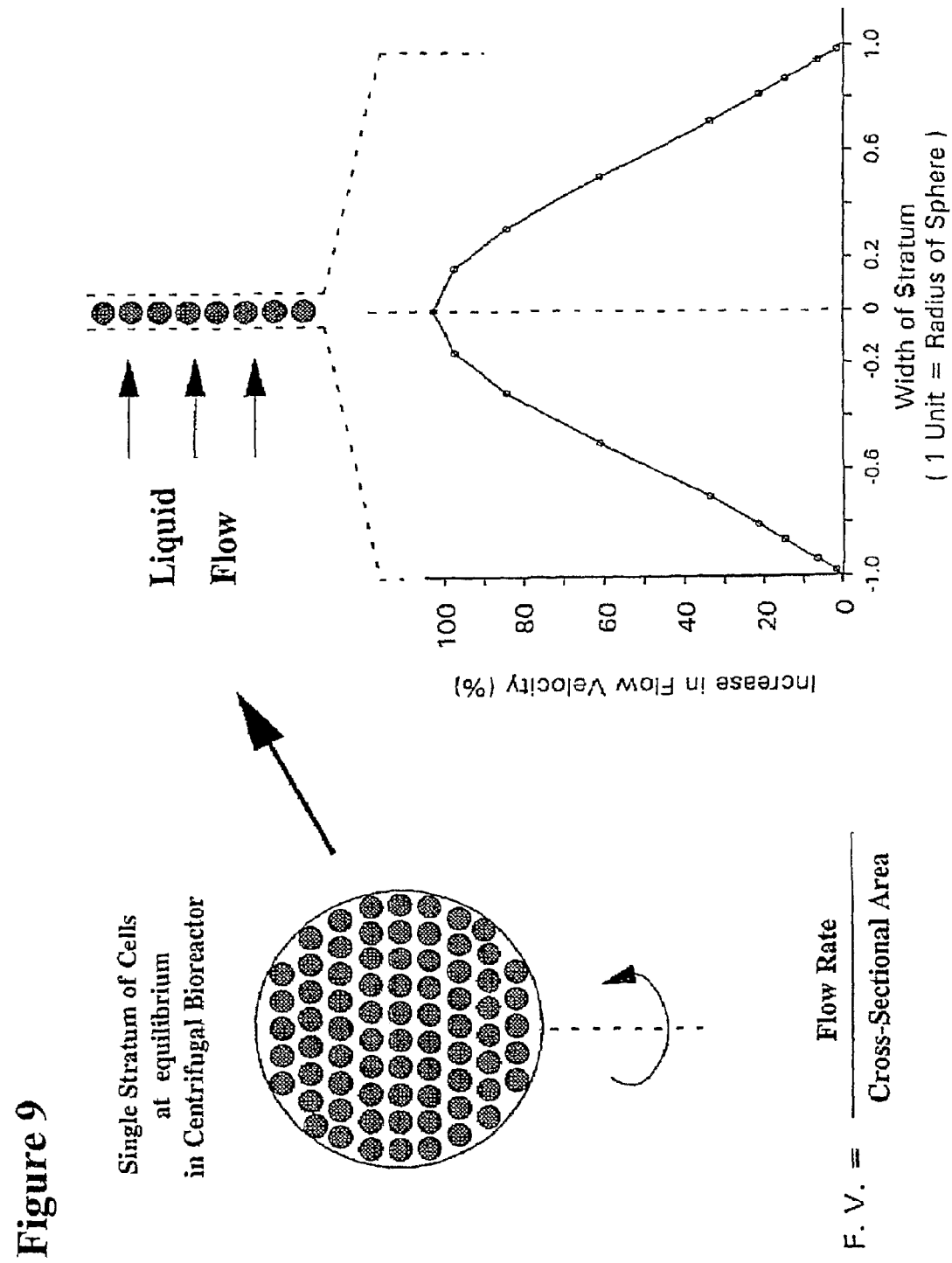
FIG. 9 is a mathematical analysis of the intra-stratum flow velocity variation in a two-dimensional array of particles in a rotating conical chamber.

While, at first glance, the description presented above would suggest that the net effect of the mismatch of forces at all radii other than that which provides immobilization would result in a "cramming" of all particles into a narrow zone centered on the appropriate radius, such is not the case. As is shown graphically in FIG. 8, as each layer of particles approaches an adjacent layer, it will move into a region where a "cushioning effect" will keep each layer apart (the horizontal arrows in FIG. 8). The explanation for the inability of adjacent layers of particles to interdigitate is a consequence of an analysis of the microscopic flow velocity profile through each layer. In FIG. 9, a single representative stratum of spherical particles confined to a particular radial distance in a chamber layer of circular cross-section is presented. The ratio of the diameters of the particles to the diameter of the cross-section of FIG. 9 is 12:1. While the magnitude of the flow velocity of the liquid through unoccupied portions of the chamber cross-section can be quantified simply from the chamber dimensions at that point, the flow velocity through a region occupied by a stratum of particles will necessarily be much greater than that in the absence of a stratum of particles because of the greatly reduced cross-sectional area through which the liquid must travel. As is shown in the graph in FIG. 9, the increase in flow velocity through a stratum of the above dimensions is more than double that determined in the free space just adjacent to the stratum on each side. This microscopic increase in local flow velocity in the region of each stratum effectively provides a "cushion" which keeps each adjacent stratum separate, and when cells are the particles, a fluidized bed of cells results.

Figure 10:
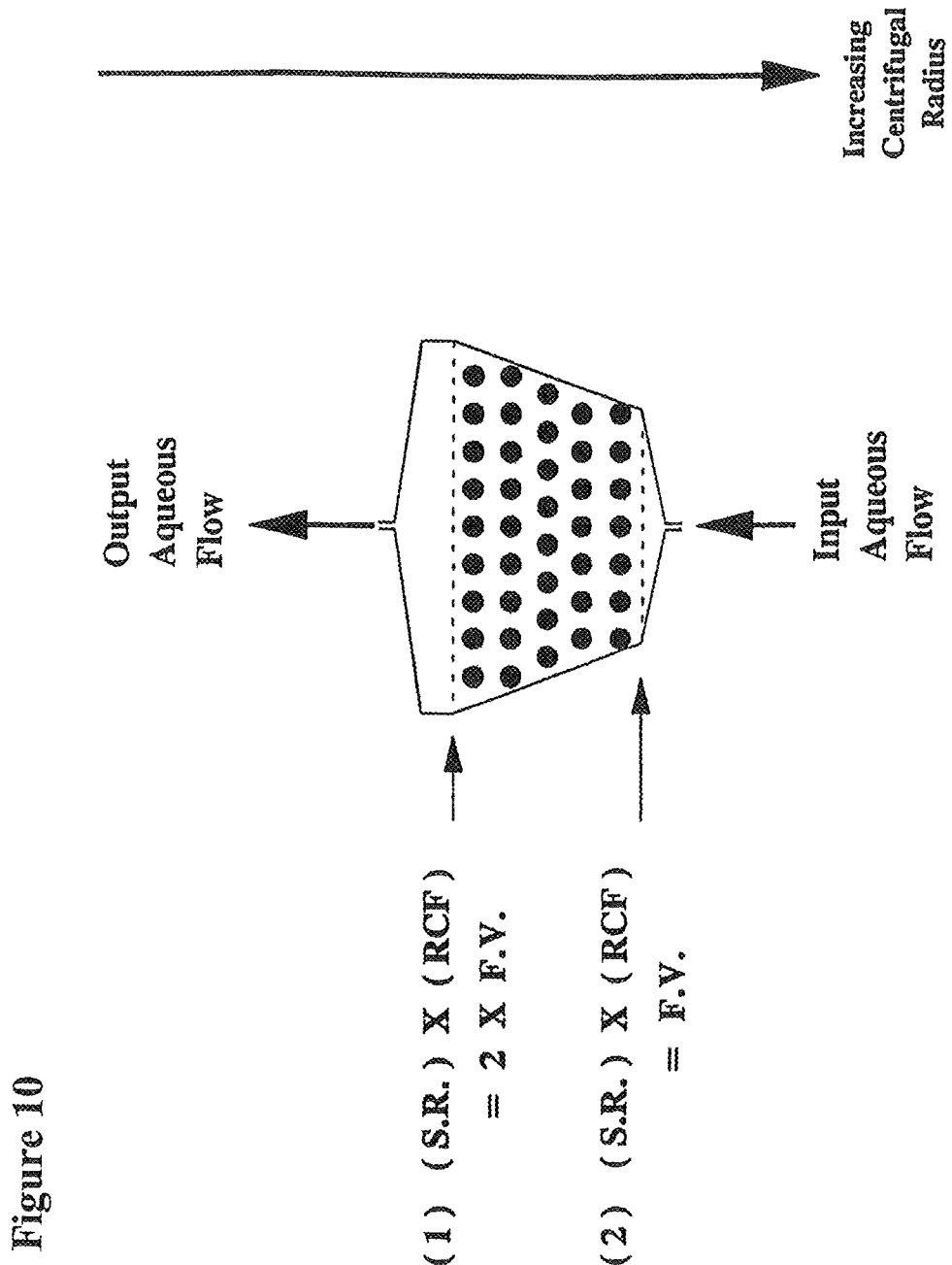
FIG. 10 is an illustration of an example of a conical-shaped chamber and the boundary conditions which determine those dimensions.

For example, in the case of a chamber geometry of a truncated cone, it is preferable that the most distal region of the truncated cone be the region where an exact equality of centrifugal forces and liquid flow velocity is achieved. The "aspect ratio" (the ratio of the small radius of the truncated cone to the large radius of the truncated cone) of the truncated cone is determined by the simultaneous solution of the two equations presented in FIG. 10. In Eqn. 2, the desired boundary condition of immobility for that "lowest" stratum of particles is presented. It states that the intrinsic sedimentation rate of the particle due to gravity (SR) times the relative centrifugal field applied at that radial distance (RCF) be exactly equal to the magnitude of the liquid flow velocity (FV) at that point. In Eqn. 1, a desired boundary condition at the opposite surface of the array of particles is presented. When the methods require the retention of particles within the container or chamber, a boundary condition wherein the product of SR and RCF is twice the magnitude of the flow velocity at that radial distance is chosen. Simultaneous solution of the desired boundary condition equations is used to solve for the ratio of the conic section diameters when the upper diameter and conic length is known. Where the methods require the expulsion or removal of particles from the container, the forces are altered and not balanced, while rotation continues. For example, the liquid force may not balanced by the centrifugal force, or the liquid force and the centrifugal force may act together in the same direction, and the particles exit the chamber.

Figure 11:
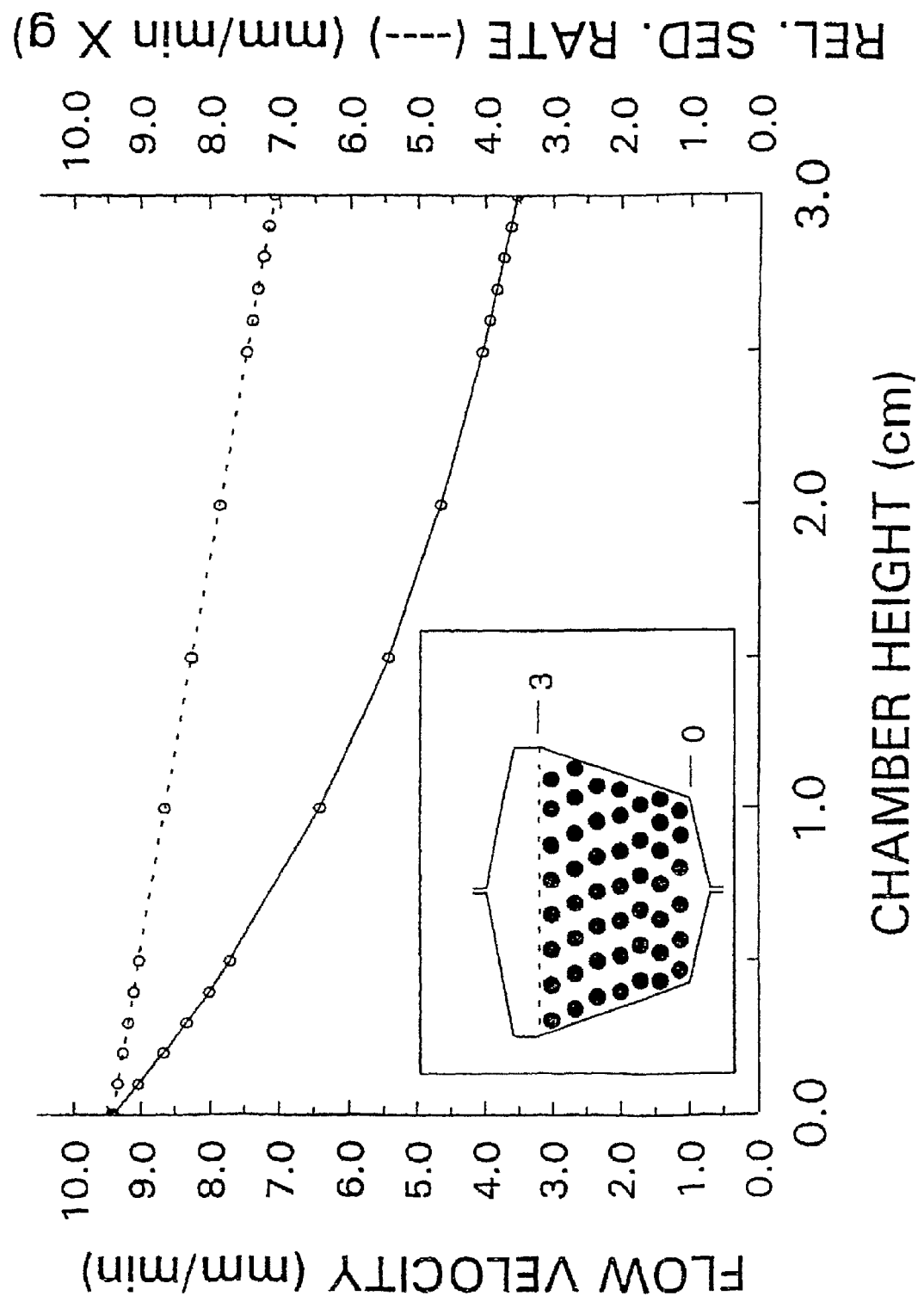
FIG. 11 is an analysis of the positional variation of the centrifugal and flow velocity forces in the chamber of FIG. 10 at a flow rate of 10 mL/min.

FIG. 11 is a profile of the relative magnitudes of the flow-related forces and the centrifugal forces across a chamber of conical cross-section which has dimensions in this example of: large diameter=6.0 cm, small diameter=3.67 cm and depth=3.0 cm. The Relative Sedimentation Rate is defined as the product of the intrinsic sedimentation rate of a particle due to gravity in a media at its optimal temperature and the applied centrifugal field. For a given flow rate (in this example 10 mL/min) into a chamber of the indicated dimensions, where the proximal end of the biocatalyst immobilization chamber is 9.0 cm from the rotational axis, the product of the intrinsic particle sedimentation rate due to gravity and the angular velocity is a constant at the given flow rate in order to satisfy the desired boundary conditions (see FIG. 10). In other words, the angular velocity need not be specified here since its value depends only on the particular particle type to be immobilized. The dotted line in FIG. 11 displays the linear variation in the centrifugal field strength from the bottom to the top of the biocatalyst immobilization chamber, while the solid line displays the corresponding value of the flow velocity. At the bottom of the chamber (the most distal portion of the chamber), the forces are equal and a particle at this position would experience no net force. At the top of the chamber, a particle would experience a flow-related force which is only one-half of the magnitude of the centrifugal field and would thus be unlikely to exit the chamber, even in the presence of a nearby region of decreasing cross-sectional area (the chamber liquid exit port), where flow velocities will increase markedly.

It should be clear from the foregoing that, subject to the necessary condition that the cross-sectional area increases as rotational radius decreases, there are other geometrical chamber configurations whose shape could be manipulated in order to establish boundary and intermediate relationships between the applied centrifugal field and the liquid flow velocity forces at any radial distance in order to establish desired resultant force relationships in the three-dimensional particle arrays. In practice, however, it is undesirable to utilize geometries with rectangular cross-sections as a result of the anomalous effects of coriolis forces which act in a plane transverse to the rotational plane. In the case of rectangular cross-sections, these otherwise unimportant forces can contribute to interlayer particle motion.

The effect of gravitational forces acting on the individual particle masses which acts independently of the applied centrifugal forces are even less important than was indicated earlier. In particular, since the basic effect of gravity on an otherwise immobilized particle is to either cause radial lengthening or radial shortening, such a motion of a particle will necessarily bring it either into a region of increased flow velocity magnitude (longer radii) or decreased flow velocity magnitude (shorter radii) with only a much smaller change in centrifugal field strength. As a consequence, the periodic motion of a particle due to gravitational effects on its intrinsic mass will be severely dampened in the presence of such unbalanced opposing force fields and will amount to, in the case of low mass particles, a vibration in place.

In some other embodiments of the present invention, the methods and systems disclosed herein may comprise an apparatus comprising a rotor that rotates in a plane substantially transverse to the gravitational axis. In this regard, the rotor may rotate about a substantially vertical axis. Embodiments of such apparatus have been disclosed in U.S. Pat. Nos. 4,939,087; 5,674,173; 5,722,926; 6,051,146; 6,071,422; 6,334,842; 6,354,986; 6,514,189; 7,029,430; 7,201,848; and 7,422,693, each of which is incorporated by reference in its entirety. The apparatus may be outfitted with at least one chamber and components to allow for the flow of liquid media through the chamber(s). The apparatus substantially immobilizes the particles that form a fluidized bed by use of the summation of the vector forces acting on each particle. More particularly, the flow of liquid media acts to create a force which opposes the centrifugal force field created by the rotating chamber(s).

In still other embodiments, the rotor may rotate about any axis between a horizontal axis and a vertical axis.

In some embodiments of the invention, the rotor is rotated at a speed sufficient to create a centrifugal force of about 25 to about 15,000×g, e.g., about 50 to about 5000×g, e.g., about 75 to about 500×g, e.g., about 25, 50, 75, 100, 200, 300, 400, 500, 600, 700, 800, 900, 1000, 2000, 3000, 4000, 5000, 6000, 7000, 8000, 9000, 10,000, 11,000, 12,000, 13,000, 14,000, or 15,000×g or more or any subrange therein, depending on the type of particle in the chamber. For example, a suitable centrifugal force for mammalian cells can be in the range of about 25 to about 1000×g, whereas a suitable centrifugal for lighter particles (e.g., bacteria or biomaterials (protein, DNA)) can be in the range of about 5000 to about 15,000×g. In certain embodiments, the average fluid flow velocity through the chamber (measured at ⅓ chamber height from the tip of the chamber) is in the range of about 5 to about 800 mm/min, e.g., about 20 to about 300 mm/min, e.g., about 5, 10, 20, 30, 40, 50, 60, 70, 80, 90, 100, 150, 200, 250, 300, 350, 400, 450, 500, 550, 600, 650, 700, 750, or 800 or more or any subrange therein, depending on the type of particle in the chamber. In other embodiments, the density of the fluidized bed can be in the range of about $0.1 \times 10^8$ to about $5.0 \times 10^8$, e.g., about $0.5 \times 10^8$ to about $2.0 \times 10^8$, e.g., about 0.1, 0.2, 0.3, 0.4, 0.5, 0.6, 0.7, 0.8, 0.9, 1.0 1.5, 2.0, 2.5, 3.0, 3.5, 4.0, 4.5, or $5.0 \times 10^8$ or more or any subrange therein, depending on the type of particle in the chamber.

The methods disclosed herein comprise use of an apparatus that substantially immobilizes the particles to form a fluidized bed of particles by use of the summation of the vector forces acting on each particle. Embodiments of such an apparatus have been disclosed in U.S. Pat. Nos. 5,622,819; 5,821,116; 6,133,019; 6,214,617; 6,334,842; 6,514,189; 6,660,509; 6,703,217; 6,916,652; 6,942,804; 7,029,430; 7,347,943; and U.S. patent application Ser. Nos. 11/384,524; 12/055,159 and 11/178,556, each of which is incorporated by reference in its entirety.

In one aspect, this apparatus can comprise a cylindrical rotor body mounted on a motor-driven rotating shaft. The rotor body can be fixed in position on the rotating shaft by means of locking collars, and is supported on either side of the rotor by bearings. In another aspect, bioreactor chambers can be mounted on the rotor, and liquid flows can be introduced into and removed from the bioreactor chambers by means of liquid channels within the rotating shaft.

In some embodiments of the invention, part are all of the fluid path within the apparatus and/or into and out of the apparatus is composed of disposable materials. The use of a completely disposable fluid path, as well as a closed system operational design, permits compliance with current good manufacturing practice (cGMP).

The apparatus and the chambers therein can be any size suitable for the methods of the invention. Depending on the size of the apparatus, the rotor body can contain one or more chambers, e.g., 1, 2, 3, 4, 5, 6, 7, 8, or more chambers. The total volume of all of the chambers in the rotor body can range from about 0.5 mL or less to about 5 L or more, e.g., 10, 15, or 20 L or more. In some embodiments, the total chamber volume is about 0.5, 1, 5, 10, 20, 30, 40, 50, 100, 200, 300, 400, 500, 600, 700, 800, or 900 mL, or about 1, 1.5, 2, 2.5, 3, 3.5, 4, 4.5, or 5 L. For large scale bioprocessing applications, the total chamber volume can be, for example, in the range of about 250 mL to about 1 L or more. For small scale processes (e.g., research laboratory use, clinical laboratory use, blood processing, etc.), the total chamber volume may be, for example, in the range of about 0.5 mL to about 100 mL or less.

When the rotor body contains more than one chamber, in some embodiments, each chamber can have its own separate fluid path. In other embodiments, multiple chambers can be connected in serial or parallel fluid pathways. In certain embodiments, different processes in the methods of the invention can be carried out in different chambers in a single rotor body.

In one aspect, the methods disclosed herein comprise the use of an apparatus that is capable of forming a fluidized bed of particles by employing rotation around an axis. In another aspect, the methods and systems of the current invention can be used where the introduction of, or the generation of, gases within a liquid medium in the chamber is desired. In other embodiments of the methods and systems disclosed herein, the presence or absence of gas in solution or out of solution in the liquid medium is immaterial to the methods and systems. Thus, the hydraulic pressure of the liquid-containing parts of the system, including the chambers and liquid lines leading to and from the chambers, may or may not be maintained at a hydraulic pressure sufficient to fully dissolve the necessary quantity of input gas and to insure the solubility of any produced gases.

Previous bioprocessing systems have been directed towards manufacturing of protein therapeutics while the cells are discarded. In contrast, the present invention provides methods for gently manipulating cells with improved recovery and decreased contamination by intracellular proteins from damaged cells. The present methods impart low shear and minimal pressure drops on the cells and provide clog-free and continuous operation compared to current cell retention systems, such as centrifugation-based systems, filtration-based systems, sedimentation systems, ultrasonic systems, and hydrocyclone systems. The present invention further provides an integrated system for processing of cells and other particles that reduces the number of processing steps as well as processing time.

The methods of the present invention can be used with any type of cell culture system (e.g., bioreactors, flasks, dishes, or other growth chambers), including perfusion culture, batch culture and fed-batch culture systems. The methods of the present invention also can be used with any type of cells, including, without limitation, bacteria, yeast, plant cells, insect cells, avian cells, mammalian cells, human cells, cells lines, primary cells, embryonic or adult stem cells, etc. The methods of the invention can also be carried out with fluids that comprise cells (e.g., bodily fluids such as blood, urine, saliva, cerebrospinal fluid, etc.) as well as other sources of cells (e.g., cells cultured on microparticles, tissue samples (e.g., biopsies or aspirates), samples of cultured primary cells (e.g., stem cells, allogeneic cells), etc.).

An aspect of the methods and systems of the present invention comprises providing perfusion cell culture conditions to cells. For example, batch, fed-batch, and perfusion bioreactor processes are widely used in the manufacturing of biotherapeutics. In comparison to batch and fed-batch processes, perfusion bioreactor processes lead to higher cell densities, titers and product quality as the product and toxic by-products are continually removed while nutrients are constantly replenished. Most perfusion processes generally run for much longer duration and require smaller equipment than batch or fed-batch processes. Although the perfusion process has several advantages over the traditional batch and fed-batch process, one of the major hurdles in perfusion process is retention of cells throughout the process. Most commonly, cells are retained in the bioreactor by using either a centrifugation or filtration based device. Centrifugation based devices can produce shear stress and nutrient deprivation to the cells in forming a pellet and these conditions lead to low viability of the cell population. Filtration based devices can suffer from clogging issues related to the filters and produce shear stress on cells, which can inhibit cell growth and activity.

In one aspect, when a stream of media containing cells passes into the apparatus comprising a chamber for rotating cells, a fluidized bed of the cells is formed with a continuous perfusion of media through it. The cells are then in an environment of minimal shear and one which provides a constant supply of oxygen and nutrients to the cells. For example, cells may be removed from a stationary bioreactor container and transferred to an apparatus comprising a rotating chamber while the media is transmitted to and through the chamber. A fluidized bed of cells can be formed within the chamber that is being rotated at a rate to retain the cells in relation to the fluid force of the media.

Figure 12:
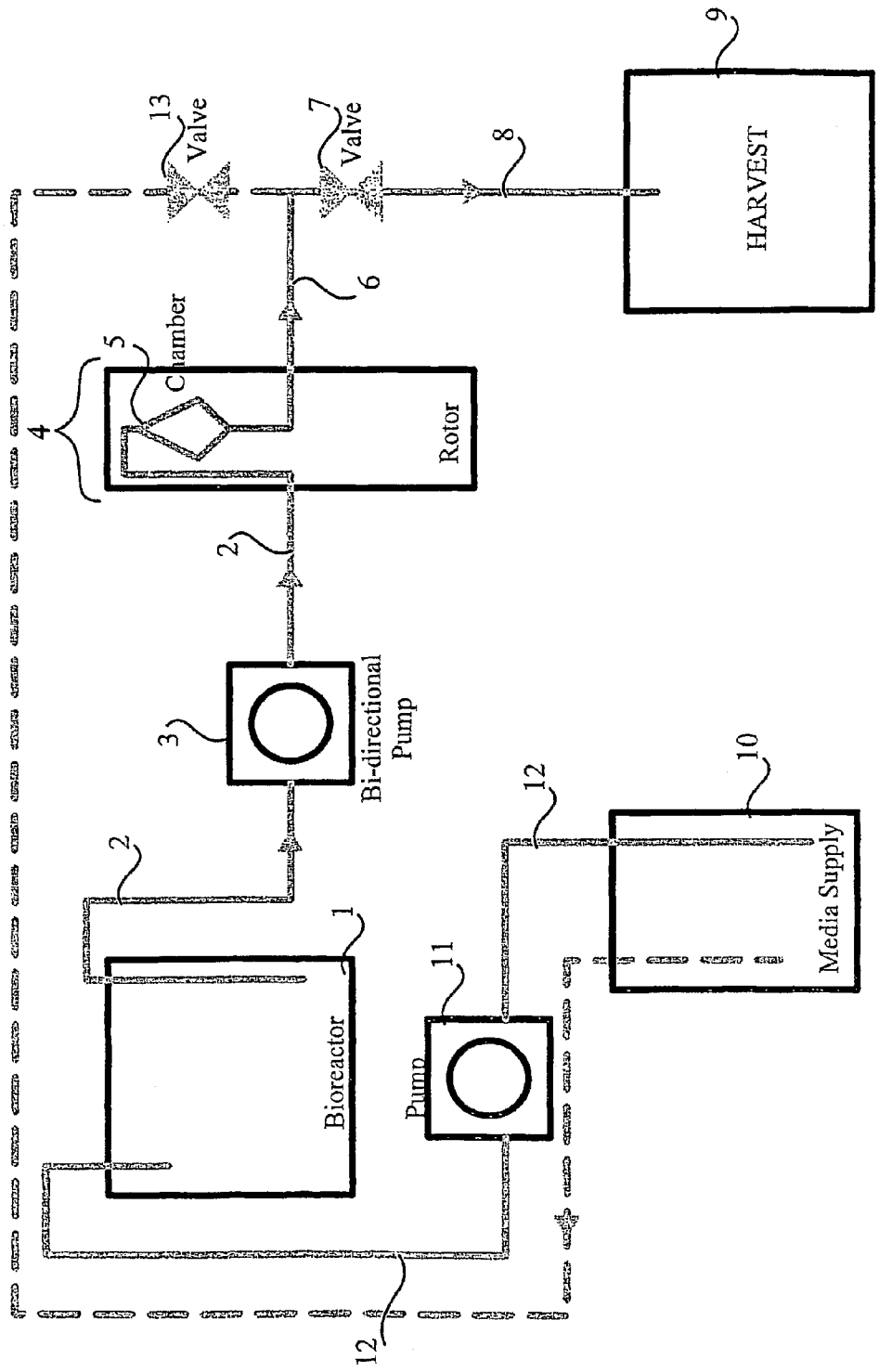
FIG. 12 is a schematic diagram of an exemplary method and system of the present invention.

One aspect is shown in FIG. 12 and is an example of perfusion bioreactor methods and systems of the present invention. Cells are located in the bioreactor 1 and are growing in the media provided. A media stream is initiated by providing media from a media container 10 using a pump 11 through pathway 12, which is generally tubing. Media and cells flow out of bioreactor 1, via pathway 2 and through a pump, such as a bi-directional pump 3, to an apparatus 4 comprising a rotating chamber 5. As the media and cells flow into the rotating chamber 5, the cells are retained in the rotating chamber 5, and the media flows out of the apparatus 4 via pathway 6. The media follows pathway 6 through valve 7, and via pathway 8, to a container 9 for spent media, or harvested media, or may be discarded (pathway not shown).

At a desired timepoint or condition, such as when the rotating chamber 5 is almost full, the cells can be transferred to another location, such as being returned to bioreactor 1. In one aspect, as the rotating chamber continues to rotate, the fluid force can be changed by reversing the flow direction, and with the centrifugal force and the liquid force acting at least partially in the same direction, all or a portion of the cells may leave the rotating chamber.

Figure 13:
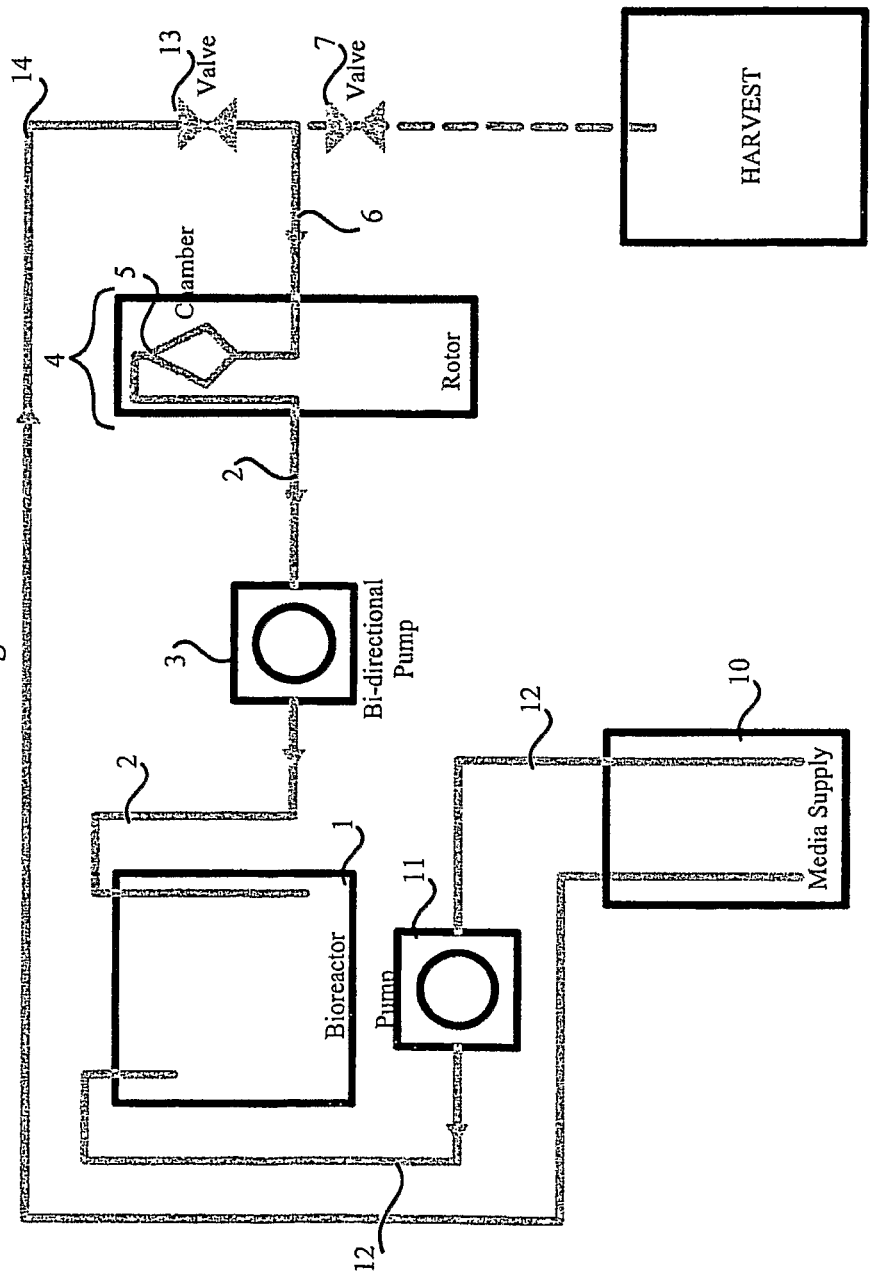
FIG. 13 is a schematic diagram of an exemplary method and system of the present invention.

As an example of this method and system, see FIG. 13. Media is pumped via pathway 14 and can be supplied from media supply container 10, or from another source of media. Media may also be provided from the bioreactor 1 (pathway not shown). Valve 13 is opened and media flows via pathway 6 into an apparatus 4 comprising a rotating chamber 5. The cells, which were retained within the rotating chamber 5, flow from the rotating chamber 5 via pathway 2 through a pump 3, such as a bi-directional pump, and into bioreactor 1. The media may be pumped through the rotating chamber 5 and the pathways, or tubing, for a desired amount of time. The cells previously retained in the rotating chamber 5 return to the bioreactor, and are mixed in the population of cells. After a desired amount of time, the flow direction is reversed again, valve 13 is closed, valve 7 is opened, and the perfusion cycle, as shown in FIG. 12 and FIG. 13 is repeated. Using this perfusion cycle, the bioreactor cells are provided with fresh media continuously and the spent media is removed.

It is to be understood in the exemplary methods and systems disclosed herein, such as in the Figures, that the methods and systems disclosed herein are not limited to only the containers, pathways or pumps as shown. For example, those skilled in the art can readily substitute a bi-directional pump with one or more pumps, and pathways are intended to provide fluid flow conduits, such as provided by tubing or piping.

Example 1 discloses a comparison of using the methods and systems of the current invention to create a perfusion bioreactor process by providing fresh media and removing spent media from the bioreactor, meanwhile capturing cells leaving the bioreactor in the spent media in an rotating chamber, and returning those captured cells to the bioreactor with little or no interference with the growth or activity of the cells. The perfusion cycle of fluid flow in one direction away from the bioreactor in which spent media is removed, followed by a reversal of the fluid flow so that captured cells and media return to the bioreactor may be repeated during the bioreactor run. The perfusion cycle may be repeated one or more times, for example, two times, 3 times, 4 times 5 times, 6 times, 7 times, 8 times, or in a range of 1-25 times, 1-50 times, 1-100 times, 1-300 times, 1-400 times, 1-500 times, 1-1000 times per batch period, or per day, or per week, or per month, depending on the needs of the cells, which can be determined by someone skilled in the art. The direction of the flow of the media which creates a fluid force in the rotating chamber, may be reversed in a method or system of the present invention every 0.5 minute, 1 minute, 2 minutes, 3 minutes, 4 minutes, every 5 minutes, every 10 minutes, every 15 minutes, every 20 minutes, every 30 minutes, every 40 minutes, every 45 minutes, every 50 minutes, every 60 minutes, every 2 hours, every 3 hours, every 4 hours, every 5 hours, every 6 hours, every 7 hours, every 8 hours, every 9 hours, every 10 hours, every 11 hours, every 12 hours, from every 0.5 minutes to every 24 hours and any range in between.

An alternative media flow can be utilized in a perfusion bioreactor. Looking at FIG. 12, fresh media is fed constantly into the bioreactor from media supply 10 via pathway 12 by pump 11. Cells and spent media are pumped out of the bioreactor 1, and cells are captured in the rotating chamber 5, and spent media is removed by pathway 6, though valve 7 into container 9. In the other half of the perfusion cycle, but not shown in FIG. 13, the media flow is reversed and media may be provided by having pathway 14 originate in the bioreactor 1 or other source, such as media supply from 10 (not shown in diagram). The media is pumped from the bioreactor, through valve 13, and through the rotating chamber 5 of apparatus 4, and along pathway 2 by pump 3 and back into the bioreactor via pathway 2. Any cells that might be entrained with the media coming from the bioreactor are either washed on through the rotating chamber 5 because the centrifugal force and the fluid flow force are at least partially aligned, or when the fluid flow is reversed again in the start of a new cycle, any cells present are captured in the rotating chamber 5 and form a fluidized bed of cells.

The methods and systems of the present invention can be used with any type of cell culture system (e.g., bioreactor) bioreactor for at least the methods and systems disclosed herein. In one aspect, the methods and systems can be used with any size bioreactor, plastic, glass or stainless steel bioreactors, and can be used with stationary or portable bioreactors. In another aspect, the methods and systems allow for bioreactors wherein the cell viability is very high because there is a reduction in the stresses on cells. In still another aspect, the methods and systems disclosed herein can be used with and attach to a cell culture system.

Figure 16:
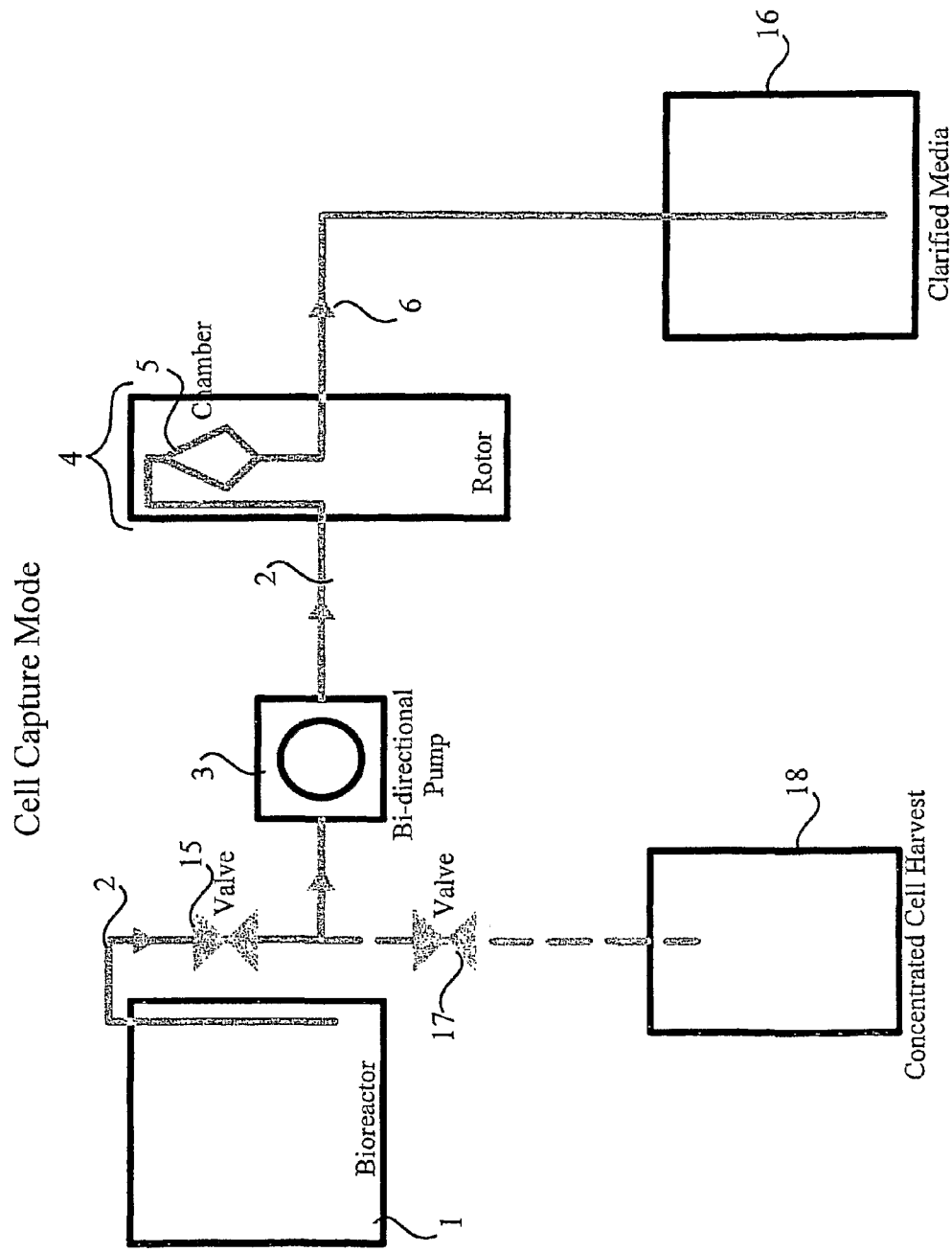
FIG. 16 is a schematic diagram of an exemplary method and system of the present invention.

A method and system of the present invention comprises use of an apparatus comprising a rotating chamber as a continuous centrifuge. See FIG. 16. In one aspect, cells can be located in the bioreactor 1. Media and cells flow out of bioreactor 1, via pathway 2, through valve 15 and through a pump, such as a bi-directional pump 3, to an apparatus 4 comprising a rotating chamber 5. Valve 17 is closed. The cells are retained in the rotating chamber 5, and the media flows out of apparatus 4 via pathway 6, and as shown to a container 16 for clarified media. The media may be recycled or may be discarded (pathway not shown). The cells form a fluidized bed in the rotating chamber 5.

As the rotating chamber continues to rotate, the fluid force is changed by reversing the fluid flow direction, and with the centrifugal force and the liquid force acting at least partially in the same direction, all or a portion of the cells may leave the rotating chamber.

Figure 17:
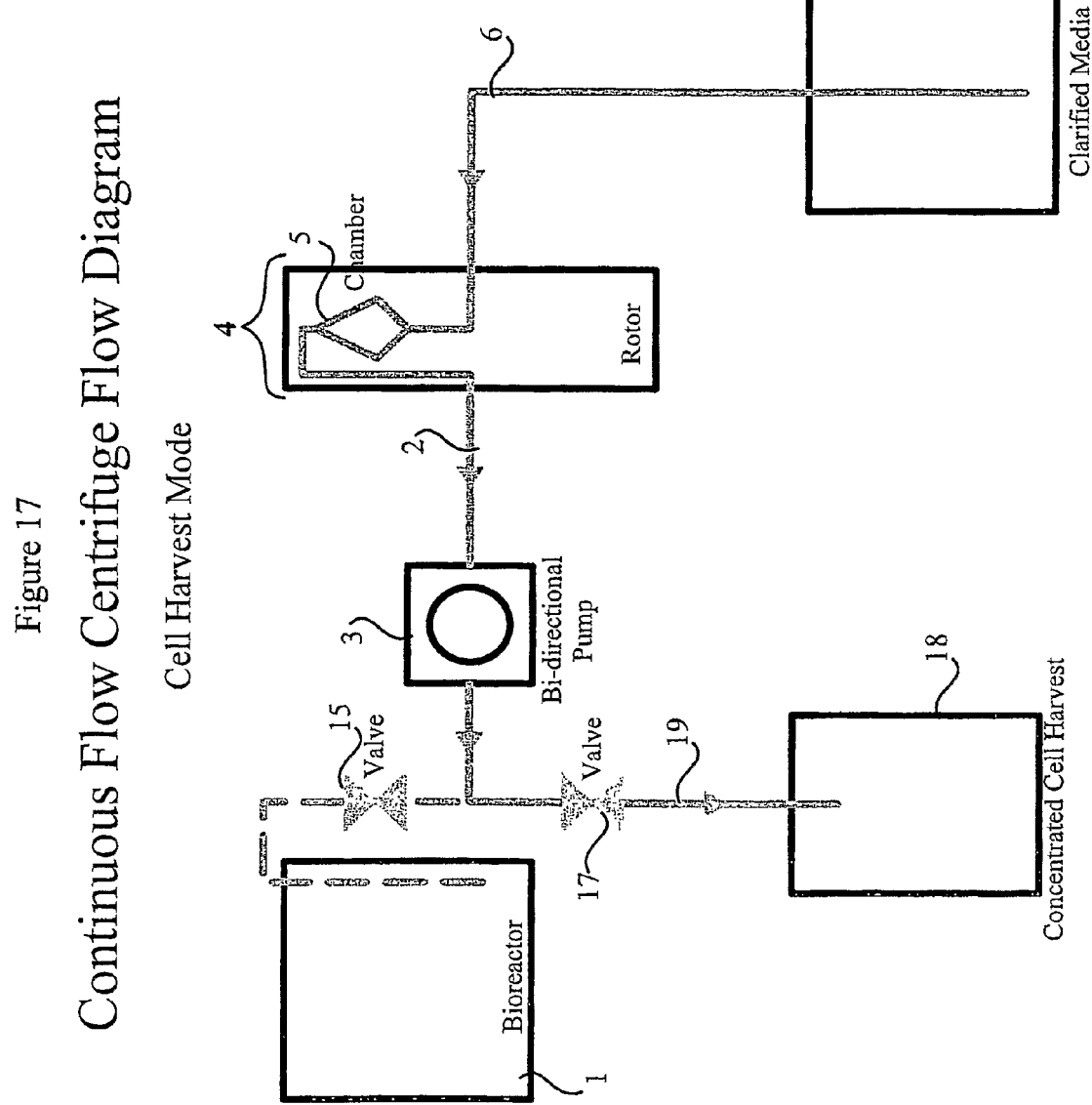
FIG. 17 is a schematic diagram of an exemplary method and system of the present invention.

As an example of this method and system, see FIG. 17. Media is pumped from a media container, such as container 16, via pathway 6 to the apparatus 4 and the rotating chamber 5. The cells leave the rotating chamber 5 via pathway 2, through bi-directional pump 3. Valve 17 is opened, valve 15 is closed, and the media and cells flow via pathway 19 and into the container 18. In one aspect, the chamber 5 of the apparatus 4 does not need to stop rotating throughout this process. The cycle of pumping cells and media from one container, containing the cells within the rotating chamber and removing the cells from the rotating chamber to a different container can be repeated multiple times, as disclosed above, for example, to concentrate cells from large volumes.

Figure 18:
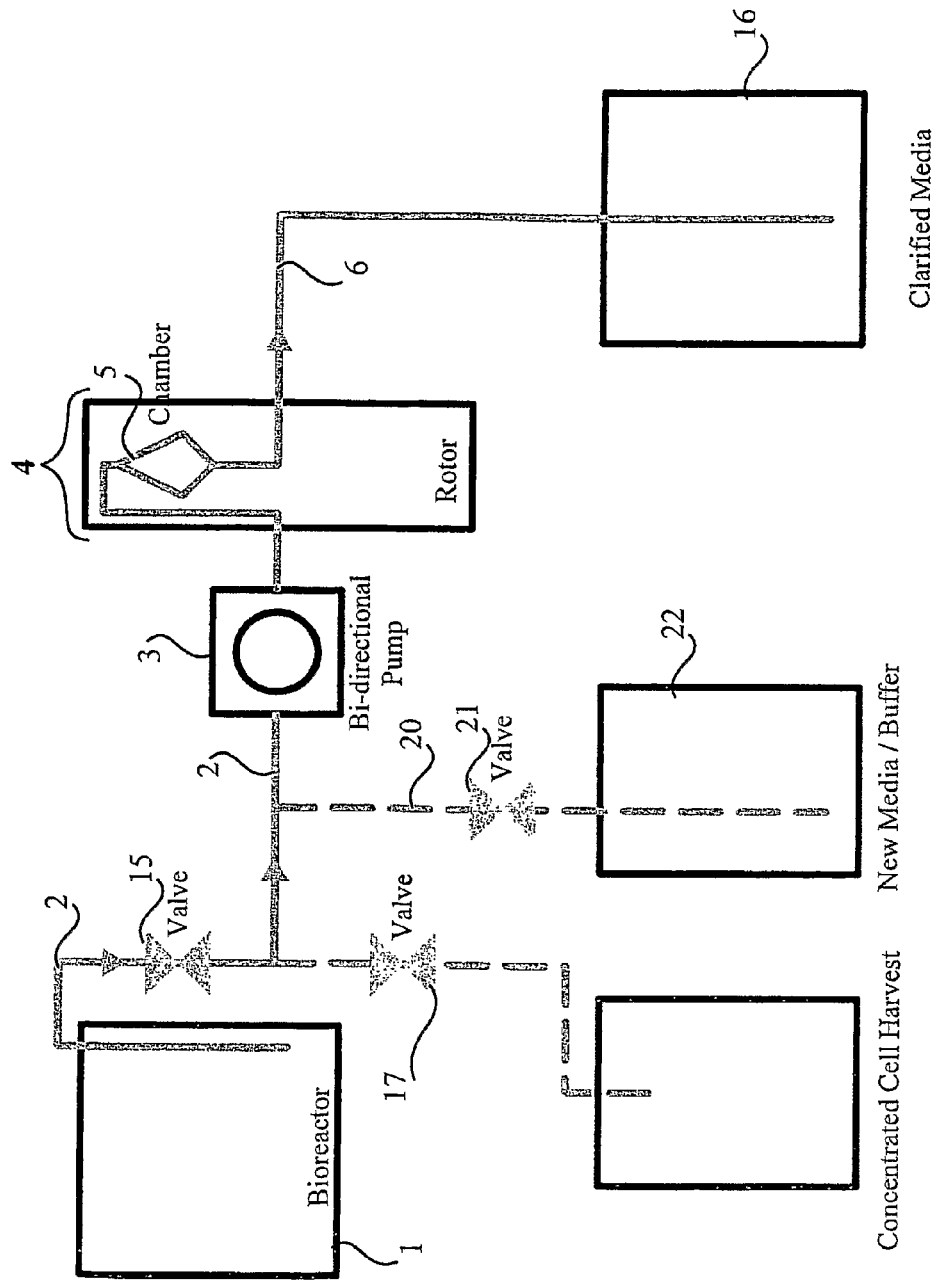
FIG. 18 is a schematic diagram of an exemplary method and system of the present invention.

Another method and system of the present invention comprises use of an apparatus comprising a rotating chamber, media and/or buffer exchange during cell culture or harvest. See FIG. 18. For example, media exchange can be used to provide fresh media or to switch cells to a different media, e.g., growth media, storage media, dispensing media, transfection media, etc. Media exchange can be used to remove contaminants from the cell culture, e.g., to remove small particulate impurities (such as particles of plastic generated from the disposable tubing and/or chamber), to remove intracellular proteins or cell debris from damaged or lysed cells, to remove free virus or other biological contaminants, etc. In some embodiments, the media exchange is at least 90% effective in replacing old media with new media (at least 90% of the old media is removed), e.g., at least 95%, 96%, 97%, 98%, 99%, 99.5%, or 99.9% effective. In other embodiments, effective media exchange can be accomplished with minimal use of new media, e.g., less than about 10 chamber volumes, e.g., less than about 9, 8, 7, 6, 5, 4, 3, or 2 chamber volumes. In further embodiments, media exchange can be carried out with high retention of cells, e.g., at least about 60%, 65%, 70%, 75%, 80%, 85%, 90%, 91%, 92%, 93%, 94%, 95%, 96%, 97%, 98%, or 99% or more retention. For example, cells are located in the bioreactor 1. Media and cells flow out of bioreactor 1, via pathway 2, through valve 15 and through a pump, such as a bi-directional pump 3, to an apparatus 4 comprising a rotating chamber 5. Valves 17 and 21 are closed. The cells are retained in the rotating chamber 5, and the media flows out of apparatus 4 via pathway 6, and as shown to a container 16 for clarified media. The cells form a fluidized bed in the rotating chamber 5.

Figure 19:
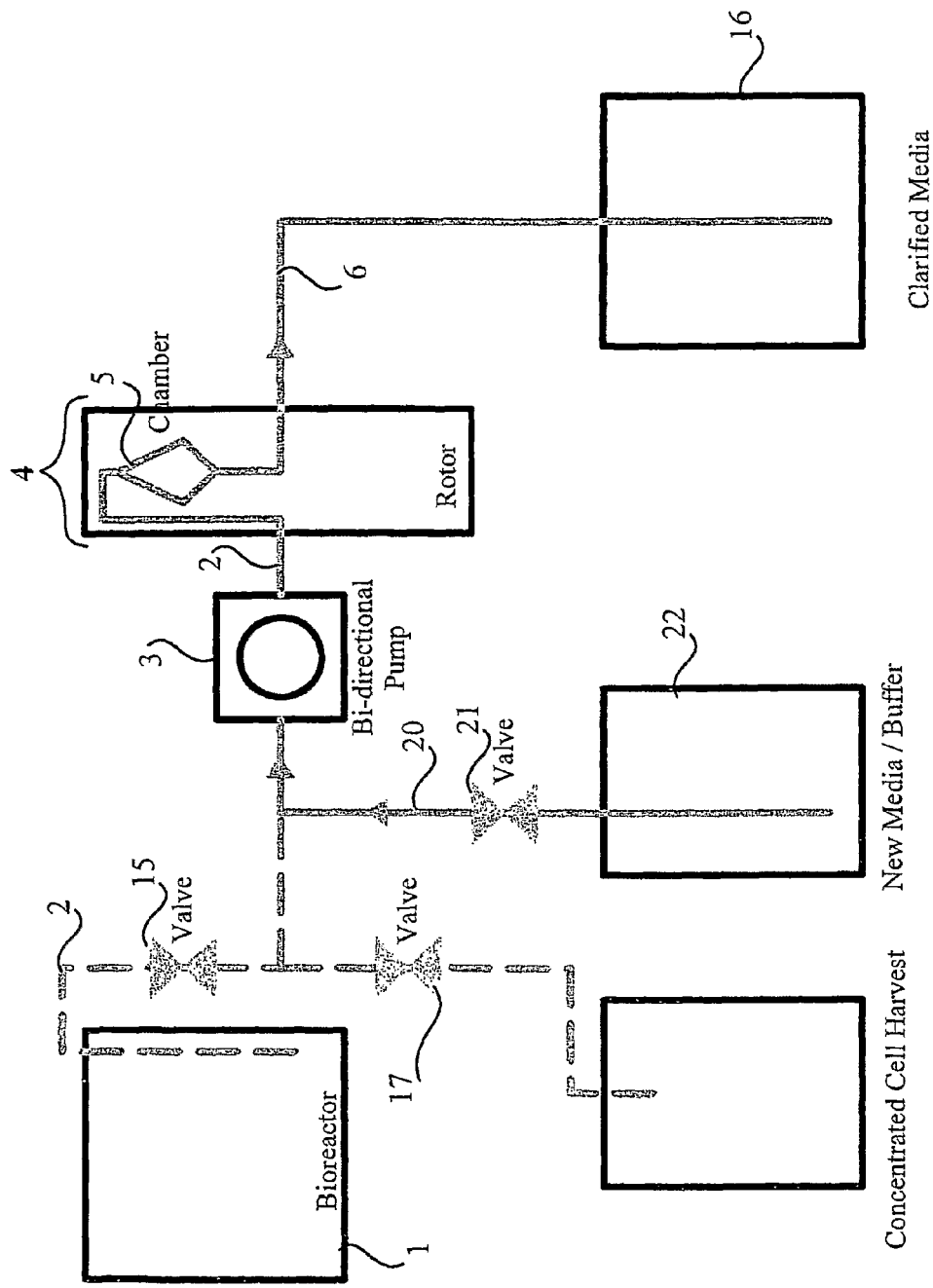
FIG. 19 is a schematic diagram of an exemplary method and system of the present invention.

An example of adding new media or buffer is shown in FIG. 19. As the rotating chamber continues to rotate, valve 21 is opened and a new media or buffer is pumped via pathway 20 through a pump, which may be bi-directional pump 3 or a unidirectional pump (not shown), to apparatus 4. The cells in the rotating chamber 5 are exposed to and surrounded by the new media or buffer, and the new media or buffer may completely or partially replace the original media or buffer. The cells remain in the rotating chamber 5, and the new media/buffer leaves apparatus 4 through pathway 6 to another container, such as container 16.

Once the new media or buffer is at a desired concentration, such as replacing 100% of the original buffer or media, the cells may be returned to the bioreactor and continue to grow in the presence of the new media or buffer. In one aspect, for example, the rotating chamber can continue to rotate, and the fluid force is changed by reversing the fluid flow direction. In another aspect, with the centrifugal force and the liquid force acting at least partially in the same direction, all or a portion of the cells may leave the rotating chamber.

In this aspect, media is pumped from a media container, such as container 16, via pathway 6 to the apparatus 4 and the rotating chamber 5. The cells leave the rotating chamber 5 via pathway 2, through bi-directional pump 3. Valve 17 is closed, valve 15 is open, and media flows via pathway 2 into the bioreactor. The cells, which were contained within the rotating chamber 5, flow from the rotating chamber 5 via pathway 2 through the bi-directional pump 3 and into the bioreactor 1.

Figure 20:
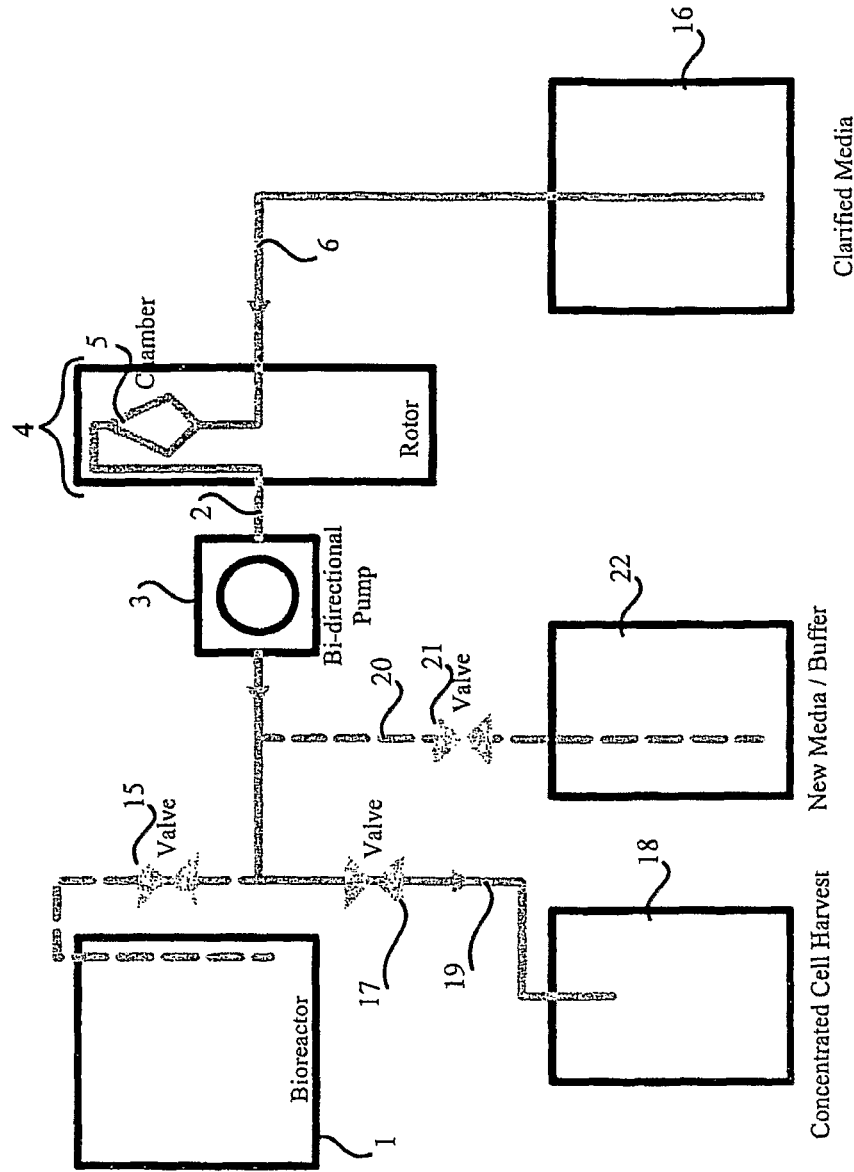
FIG. 20 is a schematic diagram of an exemplary method and system of the present invention.

Alternatively, as shown in FIG. 20, the cells can be harvested. Cell harvesting can be used, for example, to recover cells that have been expanded in culture for different purposes, e.g., cells that have been produced for use as a vaccine, cell samples from a subject (e.g., allogeneic cells or embryonic or adult stem cells that have been expanded for readministration to the subject), etc. Media is pumped from a media container, such as container 16, via pathway 6 to the apparatus 4 and the rotating chamber 5. The cells leave rotating chamber 5 via pathway 2, through bi-directional pump 3. Valve 17 is open, valve 15 is closed, and media flows via pathway 19 into the container 18. The cells, which were contained within the rotating chamber 5, flow from the rotating chamber 5 via pathway 2 through the bi-directional pump 3 and into the container 18. In one aspect, the rotating chamber of the apparatus 4 does not need to stop rotating throughout this process. The cycle of pumping cells and media from one container, containing the cells within the rotating chamber and removing the cells from the rotating chamber to a different container can be repeated multiple times, as disclosed above. This can, for example and according to one aspect, provide new media or new buffers to the cells at any time during the growth and/or activity of the cells, or to provide a media or buffer for harvesting or storage. After the cells are washed with the media or buffer, the rotating chamber is emptied of cells by reversing the fluid flow. Media/buffer exchange applications as disclosed herein may be used prior to transfection, cell dispensing, seeding a bioreactor, or any other steps in the maintenance, growth, harvesting or treating of cells in culture.

Figure 21:
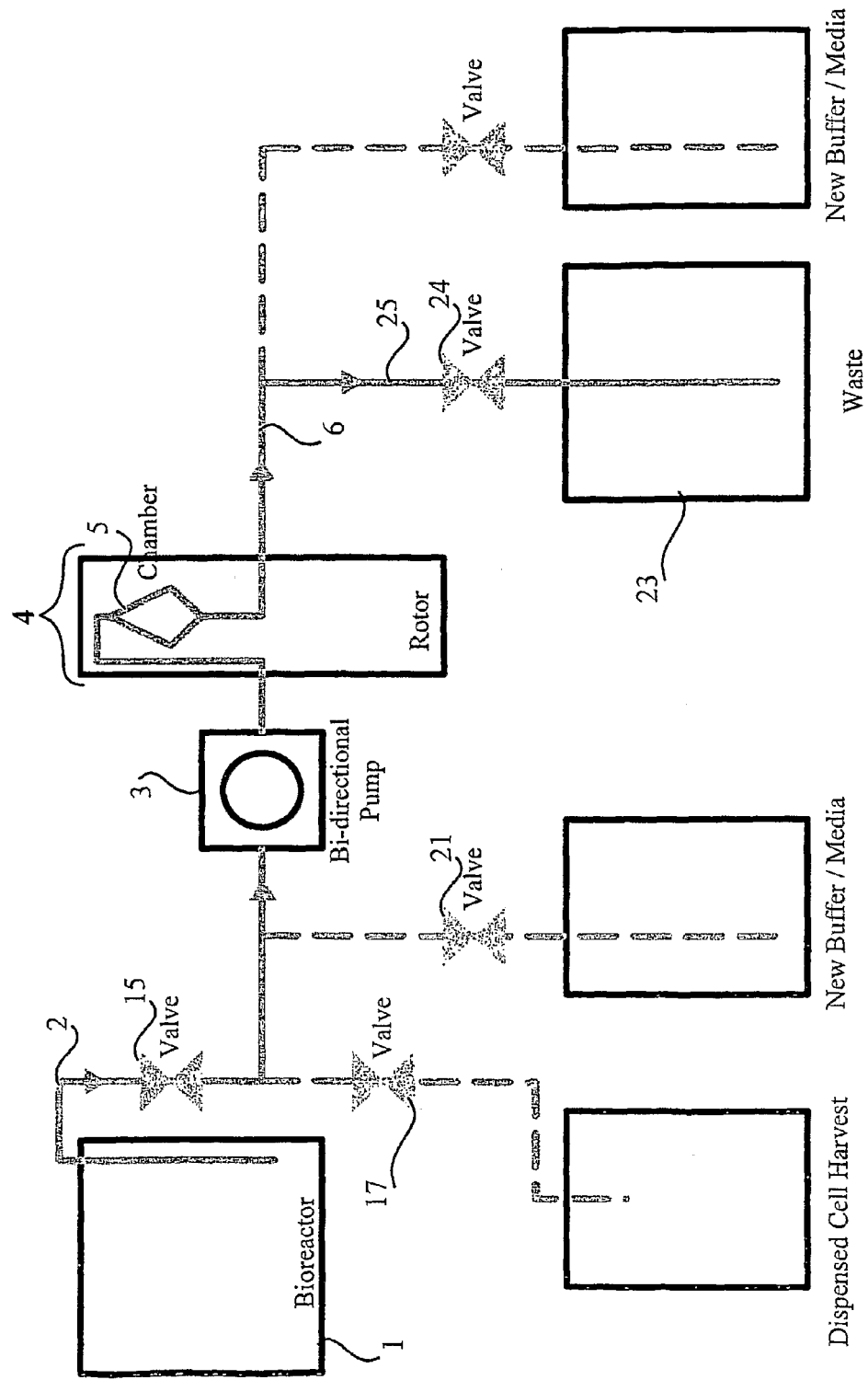
FIG. 21 is a schematic diagram of an exemplary method and system of the present invention.
Figure 22:
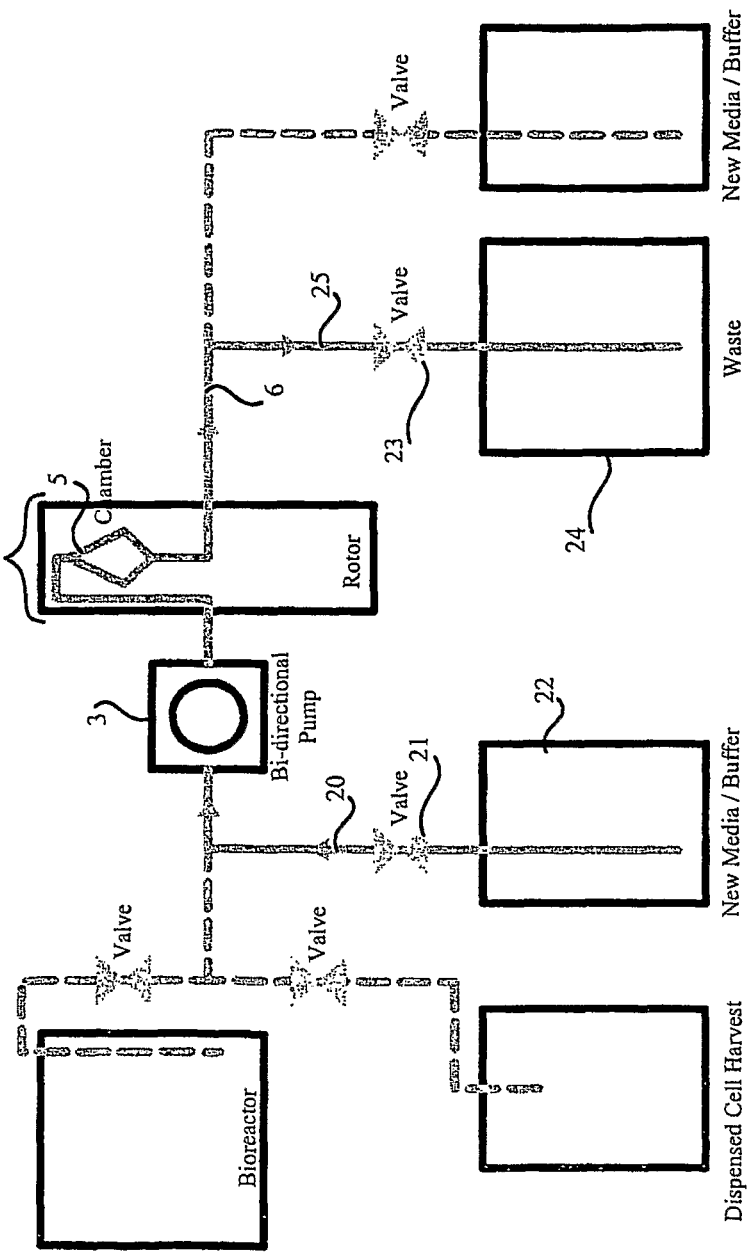
FIG. 22 is a schematic diagram of an exemplary method and system of the present invention.
Figure 23:
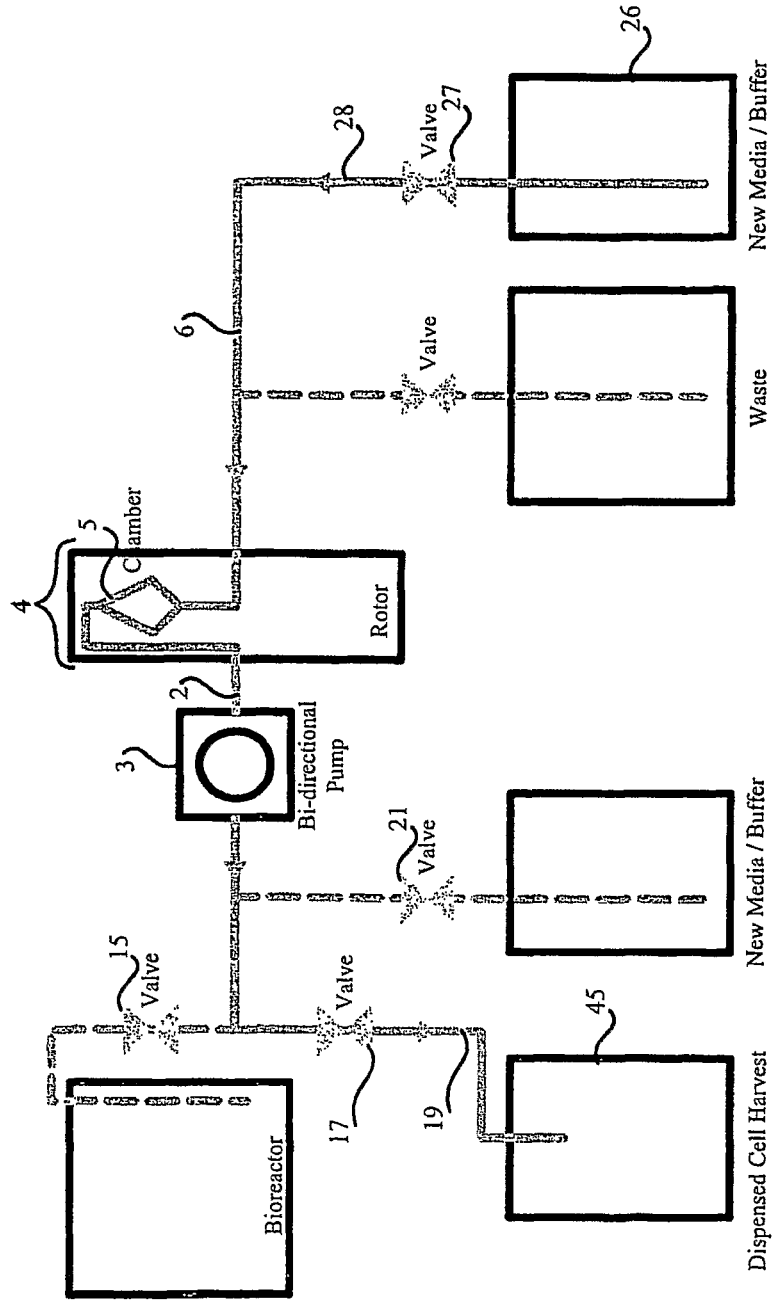
FIG. 23 is a schematic diagram of an exemplary method and system of the present invention.

FIGS. 21-23 show an aspect of the methods and systems disclosed herein wherein the methods and systems can be used as a cell dispenser to fill vials with cells. In this application, cells are concentrated, a media and/or buffer exchange may occur, and then cells are transferred from the rotating chamber by reversing the fluid flow of media, or new media and/or buffer, to dispense the cells in vials or bottles, or any desired containers. The cell dispenser can be used to generate cell banks, fill vials for cell therapy, for freezing, for dispensing into well plates, or any container for which a measured amount of cells is desired.

In the example shown in FIG. 21, cells are located in the bioreactor 1. Media and cells flow out of bioreactor 1, via pathway 2, through valve 15 and through a pump, such as a bi-directional pump 3, to an apparatus 4 comprising a rotating chamber 5. Valves 17 and 21 are closed. The cells are retained in the rotating chamber 5, and the media flows out of apparatus 4 via pathway 6 and 25, and through valve 24 to a container 23 for waste. The cells form a fluidized bed in the rotating chamber 5.

As illustrated in FIG. 22, the media and/or buffer is exchanged while the cells are in the rotating chamber 5. New media and/or buffer is pumped from the new media and/or buffer container 22 through valve 21 via pathway 20 to a pump, such as bi-directional pump 3, and into apparatus 4 comprising a rotating chamber 5. The new media and/or buffer flows through and out rotating chamber 5, through pathway 6 and 25 to valve 24 and into a container 23.

FIG. 23 illustrates an example of moving the cells from a rotating chamber to a dispensing container. In one aspect, the cells have formed a fluidized bed within the rotating chamber 5. The direction of the fluid force is changed so that the fluid force and the centrifugal force are at least partially aligned in the same direction. In another aspect, this change can occur by using a bi-directional pump 3 to reverse the fluid flow. New media and/or buffer is provided from container 26 via pathway 28 and valve 27 to pathway 6 and into rotating chamber 5 in apparatus 4. The cells and media leave rotating chamber 5 via pathway 2, through pump 3, through valve 17, through pathway 19 and into a dispensing container 45.

Figure 36:
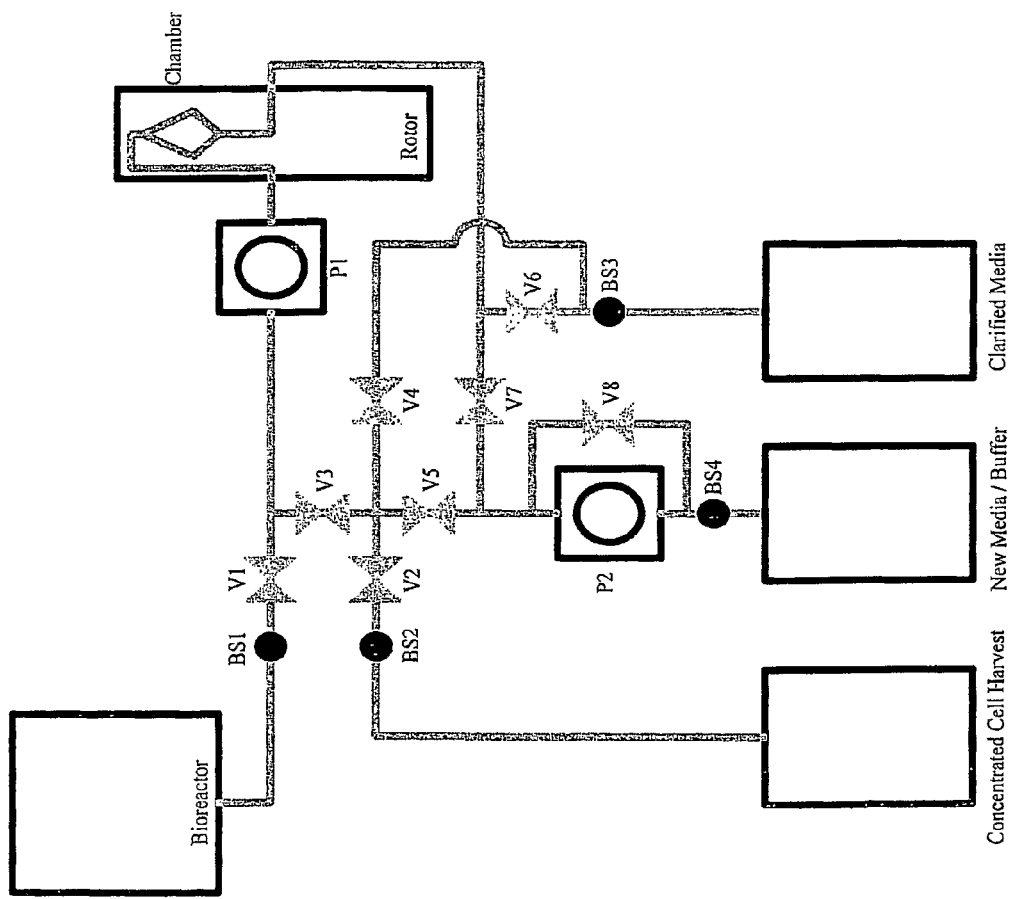
FIG. 36 is a schematic diagram of an exemplary method and system of the present invention.

During the loading of cells into the rotating chamber, stagnant areas in fluid pathways may be contaminated with, for example, culture media. These stagnant areas, or "dead legs," may occur near valves and may be rinsed with clean media/buffer to get a complete buffer wash. As used herein, "clean" media/buffer may mean that the media/buffer is sterile or substantially sterile. FIG. 36 illustrates exemplary methods and systems for achieving this result. A main pump P1 controls the flow of media through the chamber. A secondary pump P2 is set to run at a higher rate than the primary pump P1. During the loading of cells, dead legs may occur at or near valves V1 and V7. To rinse the dead legs, after the cells are loaded and while the buffer rinsing is occurring the secondary pump P2 may be turned on and valve V8 closed. Valves V3 and V5 are already open due to buffer washing. Valve V1 is opened for a short time to flush the dead leg at that valve (with the excess flow from pump P2). Pump P2 is then turned off, and valve V8 is opened and valve V1 is closed for the remainder of the buffer wash time. Before commencing the harvest routine, pump P2 is again turned on, and valve V8 is closed. Valve V7 is then opened for a short time to flush the adjacent dead leg. Pump P2 is then turned off and valve V7 is closed and valve V8 is opened. At this point an uncontaminated harvest may occur. In some embodiments, bubble detectors BS1, BS2, BS3, and BS4 sense the end of a fluid stream, and can therefore trigger the next stage of the process (e.g., washing). It is noted that bubble detectors or other flow detectors may be employed in any of the methods and systems of the present invention.

Cells in culture can be acted on to provide new products, aid in the growth of the cells, or alter the original activity of the cells. For example, cells may undergo transfection or infection procedures that introduce DNA or RNA into the cells. The materials introduced inside the cells may be DNA or other nucleic acids or constructs, proteins, chemicals, carbohydrates, vaccines or viral particles, or other activities that are known for affecting cells.

Figure 24:
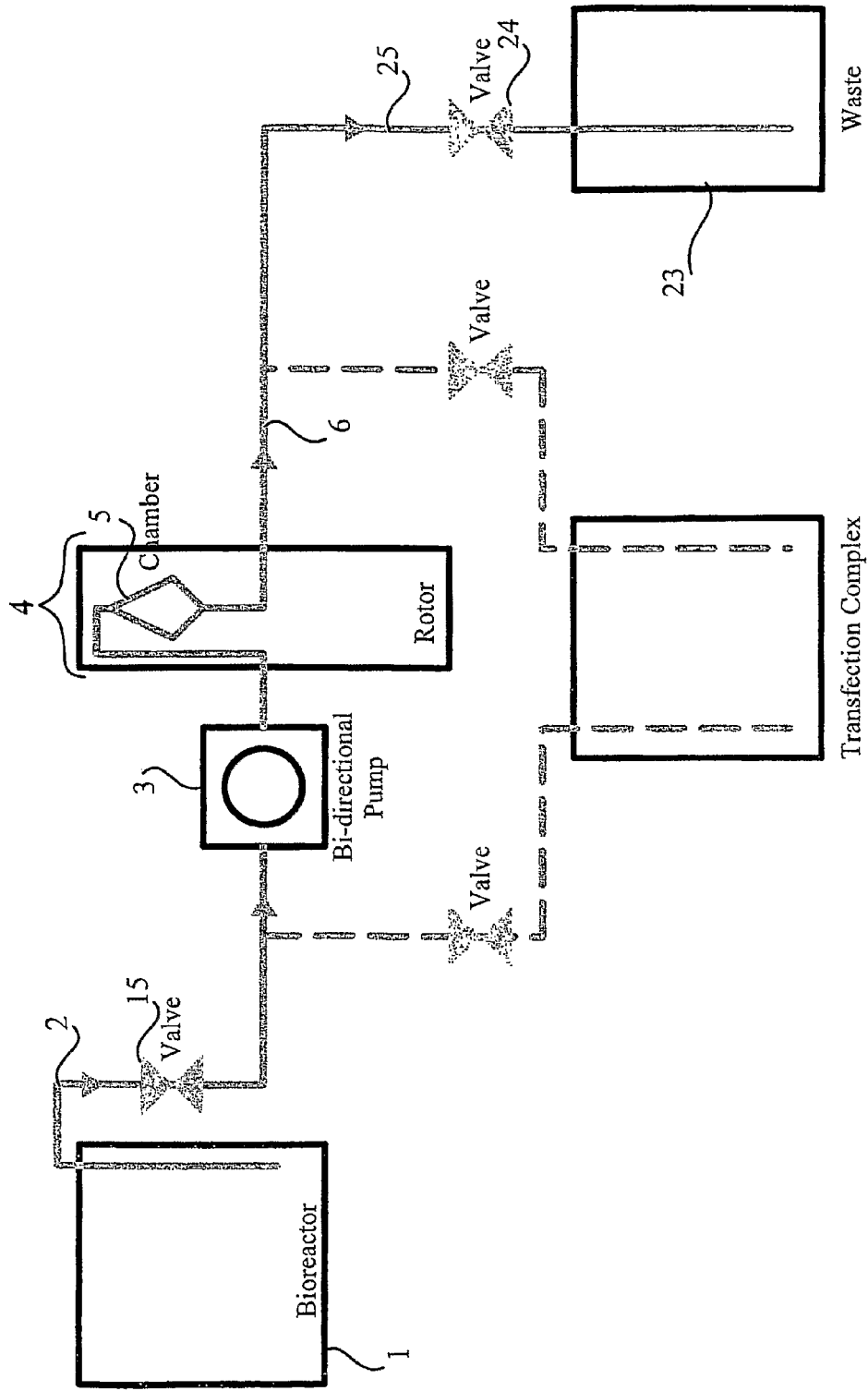
FIG. 24 is a schematic diagram of an exemplary method and system of the present invention.
Figure 25:
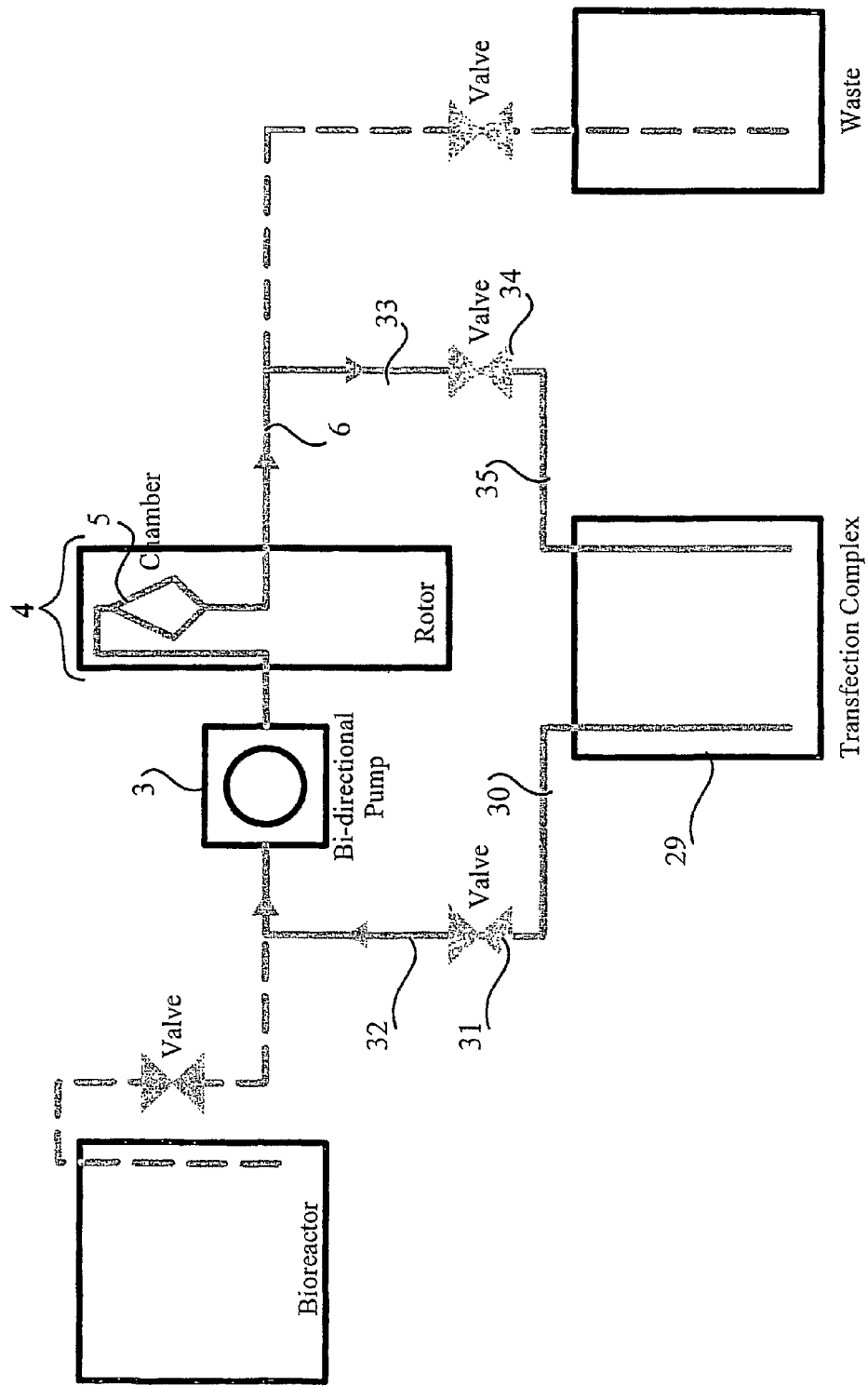
FIG. 25 is a schematic diagram of an exemplary method and system of the present invention.

Transfection is routinely used, for example, to introduce genes into a target cell. In comparison to adherent cultures, suspension cultures generally exhibit lower transfection efficiency. This may be due to reduced contact time between the transfection reagent complex and the cells. The methods and systems of the present invention may be used for transfection. In one aspect, the target cells may be exposed to the nucleic acids of interest (DNA and/or RNA) along with the correct buffers or other compounds that make up a transfection reagent complex. Any transfection technique known in the art that is suitable for use in the apparatus of the present invention can be used, including, without limitation, calcium phosphate or calcium chloride co-precipitation, DEAE-dextran-mediated transfection, lipofection, electroporation, DNA-loaded liposomes, lipofectamine-DNA complexes, and viral-mediated transfection/infection. In one embodiment, the transfection reagent complex can be a viral vector (e.g., a viral particle) containing a nucleic acid of interest, e.g., retrovirus, lentivirus, adeno-associated virus, poxvirus, alphavirus, baculovirus, vaccinia virus, herpes virus, Epstein-Barr virus, or adenovirus vector. The cells may be exposed to the transfection reagent complex by providing the transfection reagent complex to a fluidized bed of cells present in a rotating chamber of an apparatus. The cells may be grown in shake flasks or bioreactors. FIG. 24 and FIG. 25 show an example of this method and system. Exposing the cells in a higher density found in a rotating chamber increases contact time between the transfection reagent complex and cells. As the transfection reagent complex traverses through the interstitial space between the cells, contact time is increased. As shown in FIG. 24, cells are located in bioreactor 1. Media and cells flow out of bioreactor 1, via pathway 2, through valve 15 and through a pump, such as a bi-directional pump 3, to an apparatus 4 comprising a rotating chamber 5. The cells are retained in the rotating chamber 5, and the media flows out of apparatus 4 via pathway 6, through pathway 25, valve 24 and into container 23. The cells form a fluidized bed in the rotating chamber 5.

FIG. 25 shows a transfection method and system, according to one aspect, though this method and system may be used for infection or any other actions upon the cells, or provision of particular compounds or factors to the cells. In this aspect, the method and system are not limited by the material being provided to the cells. For example, in a transfection procedure, the transfection reaction complex comprising at least DNA and/or RNA or a nucleic acid construct of interest, is contained in container 29 and is pumped out of container 29 via pathway 30 through valve 31 and pathway 32 by a pump, such as bi-directional pump 3 to an apparatus 4 comprising a rotating chamber 5 containing a fluidized bed of cells. The transfection reaction complex flows through the fluidized bed of cells in rotating chamber 5, through pathway 6 and 33 to valve 34, through pathway 35 and into container 29 so that the transfection reaction complex recirculates. The transfection reaction complex may be recirculated as long as needed to ensure adequate exposure of the cells.

Figure 26:
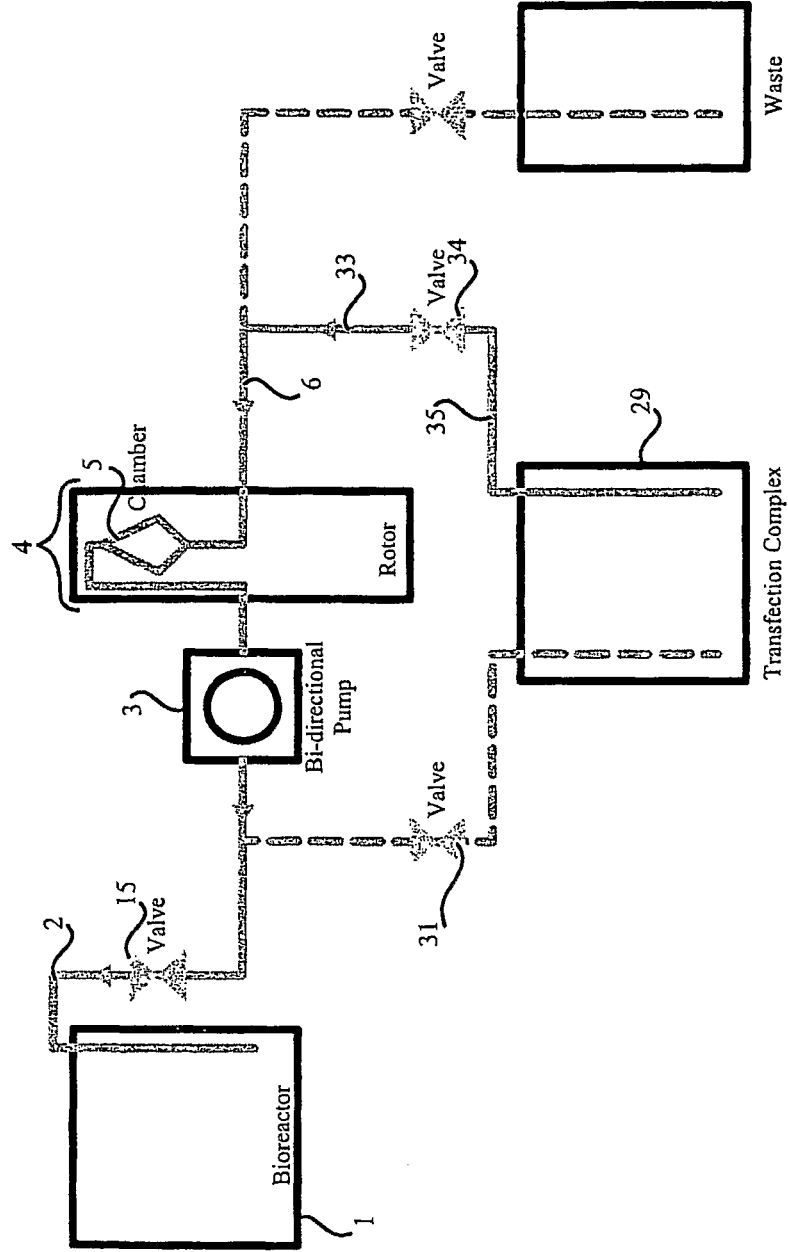
FIG. 26 is a schematic diagram of an exemplary method and system of the present invention.

In one aspect, after the transfection reaction complex has been present with the cells for an adequate amount of time, for example for 1-60 minutes, or for 1-3 hours, or for the desired time of exposure, the recycling of the transfection reaction complex fluid stream is reversed. See FIG. 26. In this aspect, the transfection reaction complex fluid flows from container 29, through pathway 35, through valve 34, through pathways 33 and 6 into the rotating chamber 5 of apparatus 4. This fluid flow change may be controlled by a pump, such as a bi-directional pump 3. With this reversal of fluid flow, the fluid force and the centrifugal force are acting at least partially in the same direction and the cells are removed from the rotating chamber 5. The cells and media pass from the rotating chamber 5, through pump 3, via pathway 2 to valve 15 and into a container, such as bioreactor 1 or shaker flasks. In one aspect, the methods and systems disclosed herein can easily be used to perform large scale transfections using a smaller amount of transfection complex than would be required otherwise. Alternatively, and in another aspect, should a media exchange be required prior to transfection, a simple media exchange step, as shown above, can be added prior to transfection. With the increased contact time between the cells and the transfection material, improved transfection efficiency can be found.

Figure 29:
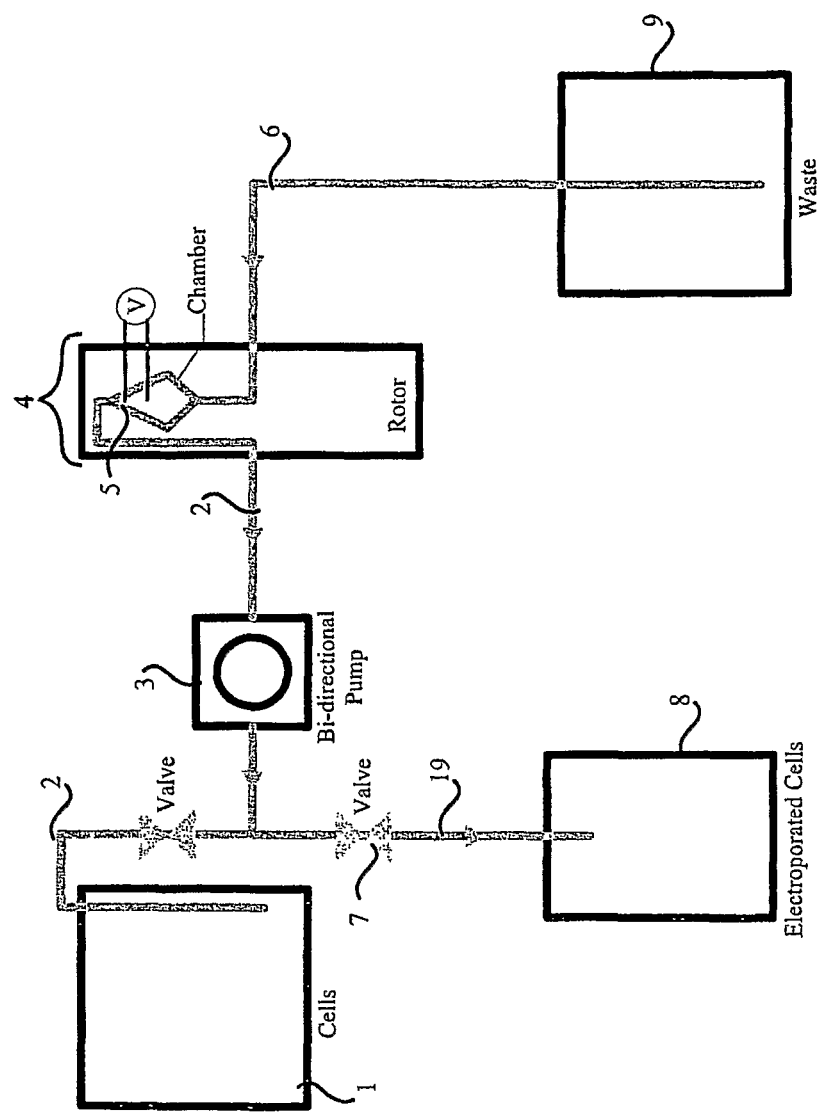
FIG. 29 is a schematic diagram of an exemplary method and system of the present invention.

Another aspect of the current invention comprises methods and systems for affecting cells or biomaterials, for example, by use of electroporation techniques. For example, an electric current can alter the permeability of cell membranes, and allow for the entry of nucleic acids or other charged molecules into the cell or cellular component, such as mitochondria. FIG. 29 illustrates one aspect of such methods and systems. In this aspect, media containing cells is pumped from a container 1 of cells in media, via pathway 2, via a bidirectional pump 3 into an apparatus 4 comprising a rotating chamber 5. The cells within the rotating chamber 5 are acted on by an electric current field, and the permeability of the cellular membrane is altered. In various aspects, one or more pulses of an electric field may be applied to the cells to change the permeability of the membrane, or to affect the cells in some manner. The media surrounding the cells may comprise one or more nucleic acid sequences, proteins, salts or ions that may cross the cell membrane with altered permeability. After electroporation, the cells may return to container 1 from rotating chamber 5 via pathway 2 through a pump, such as a bi-directional pump 3, and into container 1. The electroporated cells may be stored in an alternative container 8, by pumping the media and cells from the rotating chamber 5 via pathway 2 through a pump, such as a bi-directional pump 3, through valve 7 and into container 8. The media may be pumped through the rotating chamber 5 and the pathways, or tubing, for a desired amount of time. Waste media and/or cells may be removed from the rotating chamber 5 via pathway 6 to waste container 9.

Figure 30:
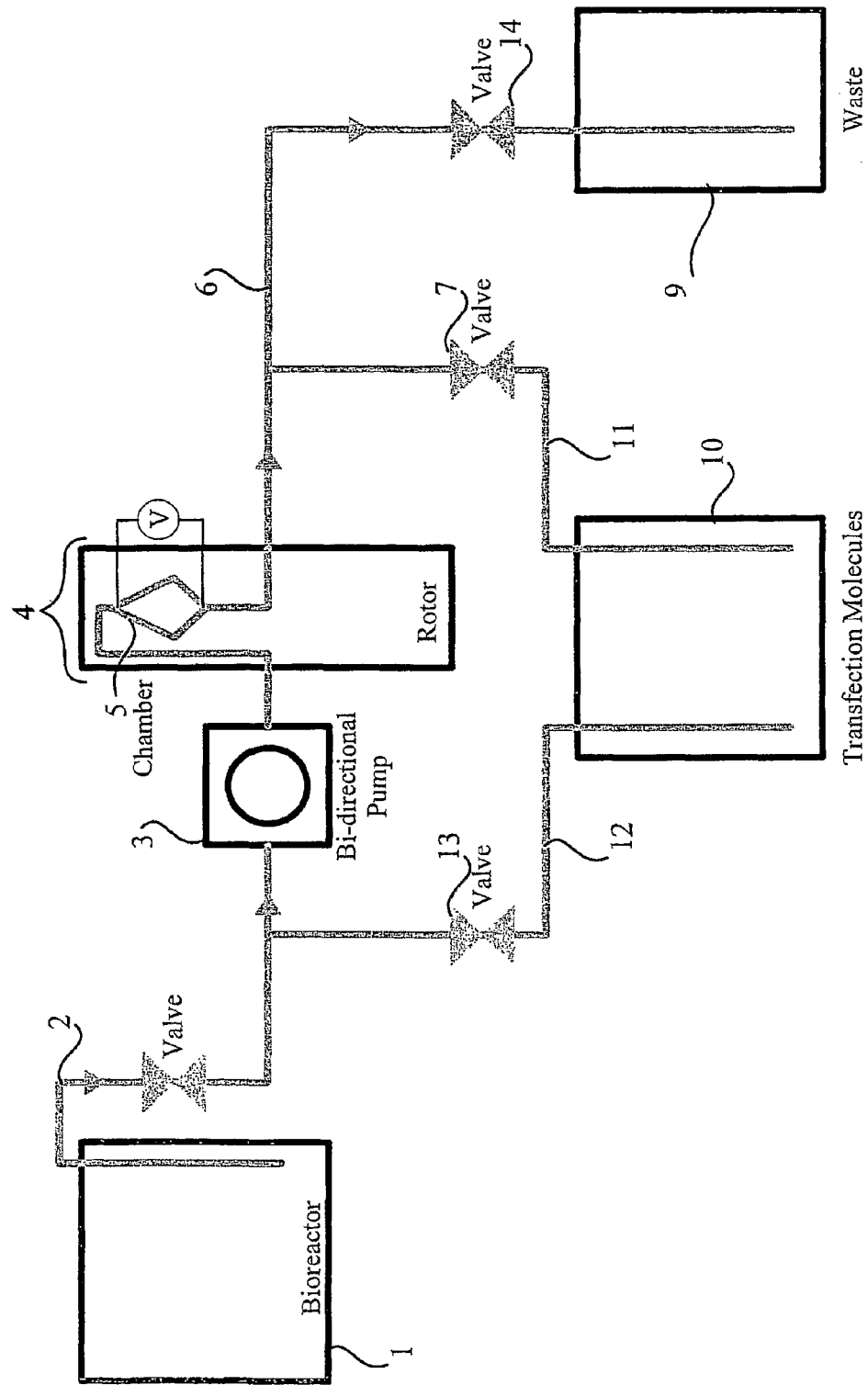
FIG. 30 is a schematic diagram of an exemplary method and system of the present invention.

FIG. 30 shows another aspect of electroporation methods. Media containing cells is pumped from a container 1 of cells in media, via pathway 2, via a bidirectional pump 3 into an apparatus 4 comprising a rotating chamber 5. The cells are retained within the rotating chamber 5, and are concentrated in the chamber as a fluidized cell bed. The cells may be washed at this point and fluid that contains molecules (stored in container 10) can be re-circulated through the fluidized cell bed via pathways 11 and 12. An electric field is applied in short pulse(s) to incorporate the molecules into the cells. Once the electroporation is complete, the cells can be collected for further processing. The cells may be pumped to one or more sites.

In general, electroporation methods comprise exposing particles, including biomaterials, such as cells or cellular components with membranes, to an electric field of appropriate strength to alter the permeability of the particle or the cell membrane. Charged molecules, such as nucleic acids, DNA, RNA, charged ions, proteins, enter the particles more easily because of the altered permeability. As an example, cells are concentrated in a rotating chamber of an apparatus comprising a rotating chamber where the cells form a fluidized bed in the chamber. The cells may be washed, and a media containing charged molecules can be added to the fluidized bed. In certain embodiments, the cells may be exposed to the charged molecules before, concurrently with, and/or after the electric field is applied. An electric field is applied, for example, in short pulses, and the cellular membranes are altered. The type, strength, and length of the electric pulse can be optimized for each cell type. For mammalian cells, in certain embodiments, the pulse is in the form of a square wave or an exponential. The voltage of the pulse can be in the range of about 50 to about 1000 V, e.g., about 100 to about 500 V, e.g., about 50, 100, 200, 300, 400, 500, 600, 700, 800, 900, or 1000 V or more or any subrange therein. The length of the pulse can be in the range of about 1 ms to about 100 ms, e.g., about 5 to about 50 ms, e.g., about 1, 2, 3, 4, 5, 6, 7, 8, 9, 10, 15, 20, 25, 30, 35, 40, 45, 50, 55, 60, 65, 70, 75, 80, 85, 90, 95, or 100 ms or more or any subrange therein. The cells can be pulsed more than once, e.g., 2, 3, 4, or 5 times or more. Charged molecules or ions enter the cells. The cells may then be transferred to another holding tank or returned to the general population, using reverse flow, and the process can be repeated.

The methods and systems disclosed herein can be used to separate a population of cells, including but not limited to, separating based on density and/or size. In one embodiment, fluid containing different populations of cells, such as cells that differ in size or in density, can be fed into a rotating chamber. Examples of fluids containing different populations of cells include, without limitation, bodily fluids (such as blood, urine, saliva, cerebrospinal fluid, etc.), digested tissue samples, co-cultures of different cell types, etc. In the rotating chamber, the cells can be separated by modulating the fluid flow (fluid force) and/or centrifugal force. A fluidized bed of cells can be formed in the rotating chamber. By changing the rate of rotation, thus altering the centrifugal force applied to the cells, by changing the fluid flow, thus altering the fluid force on the cells, or by changing both the rate of rotation and the fluid flow, particular cells or a subpopulation of cells that have a similar size and/or density can be separated from the fluidized bed and removed from the rotating chamber. Once the fluid force and the centrifugal force are adjusted appropriately, lighter and/or smaller cells can exit out of the rotating chamber in the media stream. See FIG. 27. After a cell bed is formed, fresh media or buffer could be used to separate another subpopulation of similar cells by once again adjusting the fluid force and/or the centrifugal force. This process can be repeated several times to separate multiple subpopulations of cells that differ by density and/or size. Finally, heavier/larger cells are harvested by reversing the flow of fresh media (FIG. 28).

Figure 27:
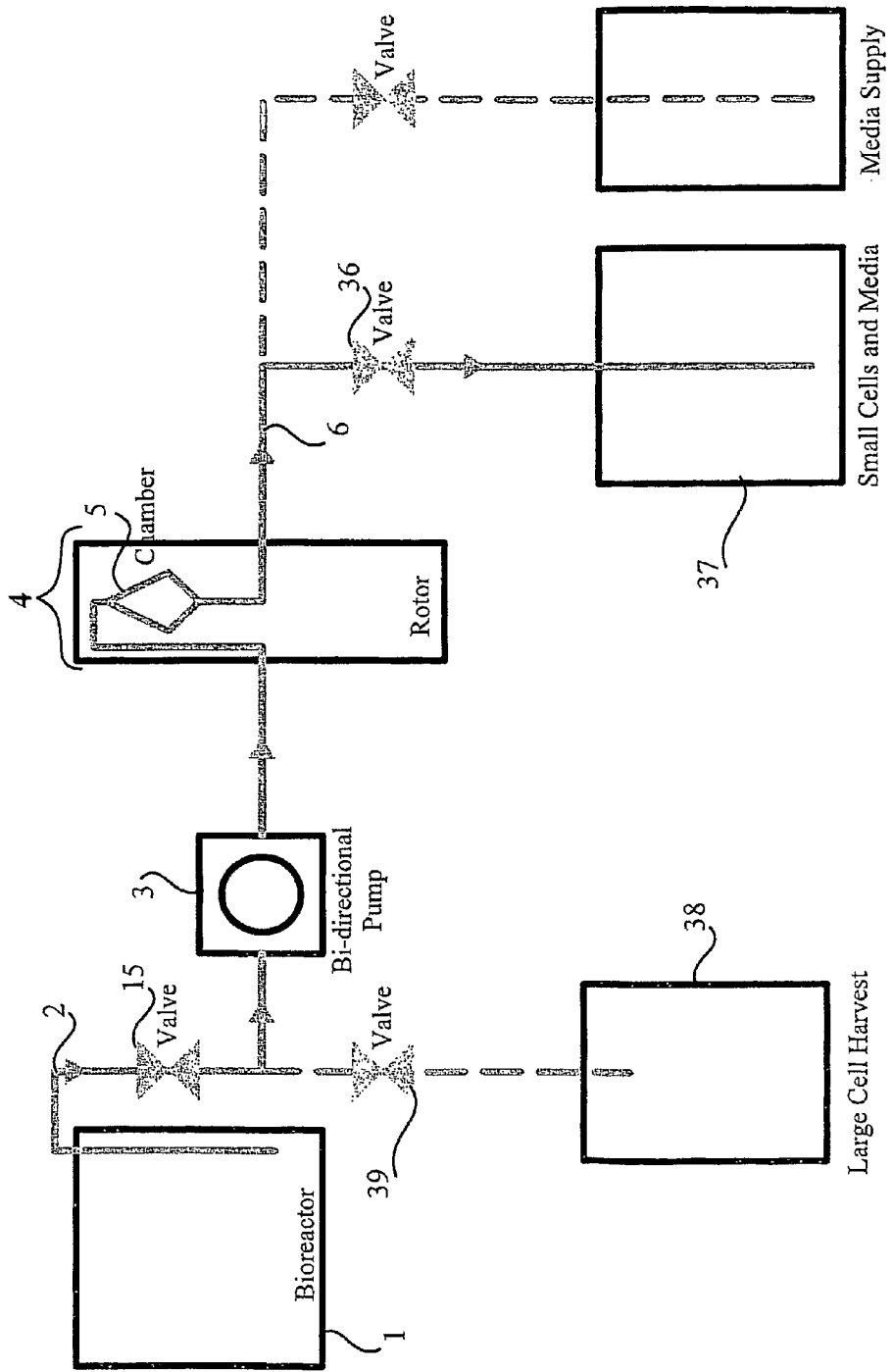
FIG. 27 is a schematic diagram of an exemplary method and system of the present invention.

In FIG. 27, for example, cells comprising a mixed population of large and small cells are located in container 1. Media and cells flow out of container 1, via pathway 2, through valve 15 and through a pump, such as a bi-directional pump 3, to an apparatus 4 comprising a rotating chamber 5. The cells are retained in rotating chamber 5, and the media flows out of apparatus 4 via pathway 6, through valve 36 and into container 37. To remove smaller and/or lighter cells, the fluid force is altered by increasing or decreasing the rate media is pumped into rotating chamber 5, and/or the centrifugal force is increased or decreased by altering the rate of rotation of the rotating chamber 5. Either one of the fluid force or centrifugal force, or both can be changed to remove a subpopulation of cells. The remaining cells reform a fluidized bed, and then either one or both of the fluid force or centrifugal forces are changed to remove another subpopulation of similar cells, as described above, and may be repeated as often as desired. When the procedure for removing subpopulations of cells is completed, and the desired population remains within the rotating chamber, the fluid flow is reversed so that the fluid force and the centrifugal force are at least partially, if not completely, aligned. The cells can then be removed from the rotating chamber to another container. In methods of cell culture, one may want to select small cells or large cells, for example, and the present invention provides methods and systems that can provide the segregation of cells to select for the desired type.

Figure 28:
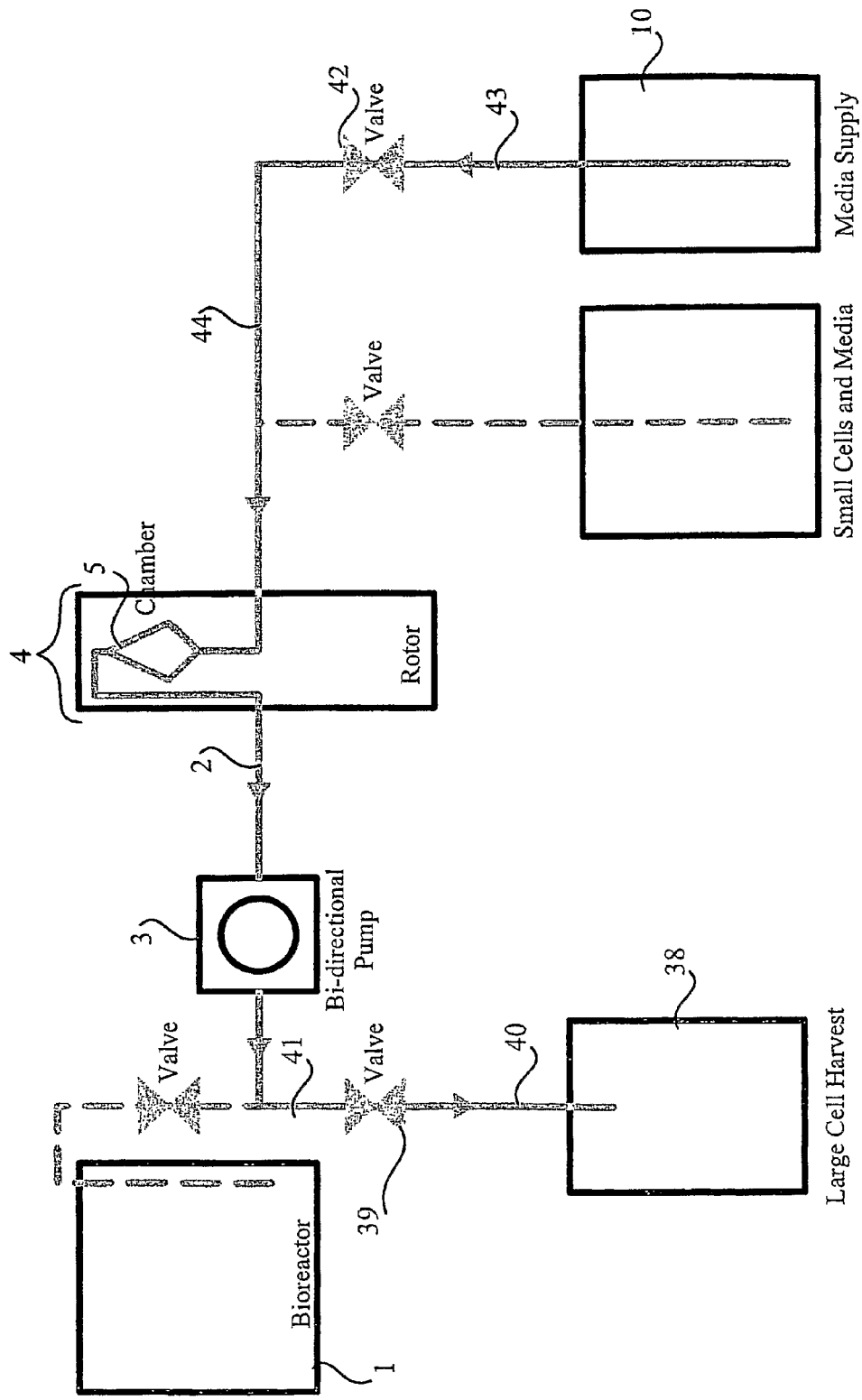
FIG. 28 is a schematic diagram of an exemplary method and system of the present invention.

One aspect of a method and system for harvesting heavier/larger cells is illustrated in FIG. 28. In this aspect, the fluid flow is reversed, and media is provided from container 10 via pathway 43 to valve 42 and via pathway 44 to apparatus 4 comprising a rotating chamber 5. The cells and media flow out of rotating chamber 5 via pathway 2 to a pump, such as bi-directional pump 3, via pathway 41 to valve 39, and into container 38 via pathway 40.

Figure 31:
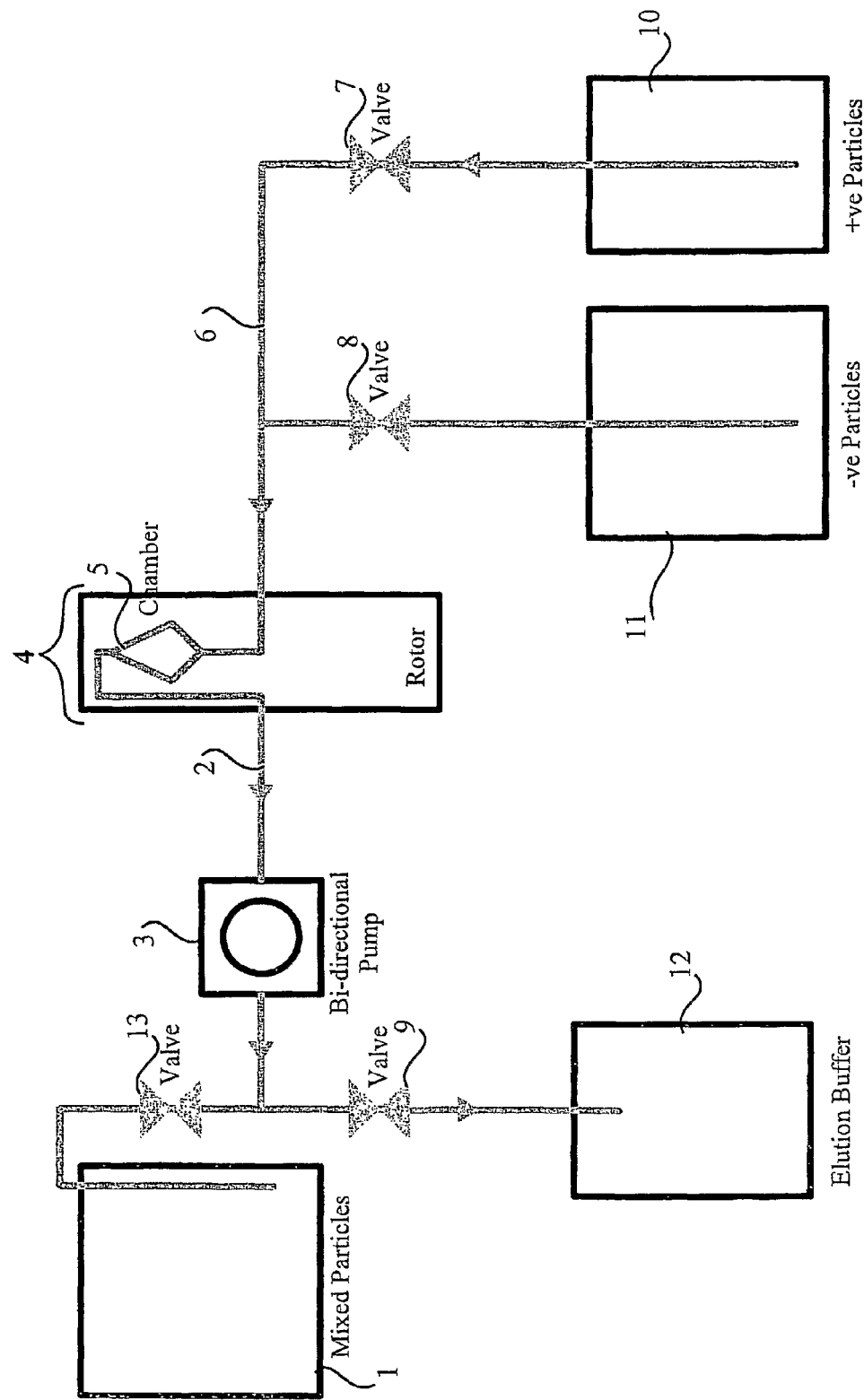
FIG. 31 is a schematic diagram of an exemplary method and system of the present invention.

The methods and systems disclosed herein may be used for selection, purification, or enrichment of particular cells, biomaterials, or particles. For example, affinity methods may be used to select for a particular target, such as a cell. Affinity targets can include specific cell types, e.g., embryonic or adult stem cells, pluripotent cells, tissue specific cells, or cells of a specific differentiation stage. An affinity matrix may be contained within a rotating chamber and a mixed population which comprises one or more targets can be transferred into the rotating chamber. The affinity matrix can be any suitable particle, bead, or resin that binds to an affinity target and is capable of forming a fluidized bed, e.g., standard chromatography material. The affinity matrix can comprise a material that binds the affinity target, e.g., antibodies (polyclonal, monoclonal, fragments, Fc regions, etc.), protein A and protein G containing materials, dyes, receptors, ligands, nucleic acids, etc. Cells or particles that have affinity for the matrix will be bound or retained by the matrix, while other particles or cells may exit the chamber. The exiting material may be recirculated so that it reenters the rotating chamber for access to the affinity matrix again. The cells or particles bound or associated with the affinity matrix may be released by adding an elution media in the media stream in the rotating chamber. The released cells or particles may be collected after release from the affinity matrix. See FIG. 31.

Another aspect comprises methods and systems for enrichment of cells or particles, for example, by use of an affinity matrix. For example, in FIG. 31, systems and methods for separating target cells or particles are disclosed, according to one aspect. In this aspect, media containing target cells is pumped from a container 1 of heterogeneous population of cells in media, via valve 13, via a bidirectional pump 3, via pathway 2 and into an apparatus 4 comprising a rotating chamber 5. The cells, which are retained within the rotating chamber 5, are acted on by the affinity matrix, and the target cells, +ve, are retained by the affinity matrix, and the other cells, −ve, flow through the rotating chamber. The media and cells exiting the rotating chamber may be recirculated for one or more passes through the rotating chamber and the affinity matrix, and exiting cells, −ve, pass through valve 8 and are stored in container 11. An elution media is pumped from container 12 through valve 9 via a bidirectional pump 3, via pathway 2 into the rotating chamber 5 of apparatus 4. The eluting media breaks the association between the target cells and the affinity matrix so that the target cells, +ve, are removed from the matrix. The target cells flow out of rotating chamber 5 through pathway 6, via valve 7 and are contained in container 10.

In another example, cells expressing a specific surface receptor can be isolated from a mixed population of cells. Beads coated with antibody for the receptor function as the affinity matrix and can be immobilized within a rotating chamber. As a mixed population of cells is introduced in the system, cells that exhibit the receptor are bound by the antibody on the matrix and are retained within the rotating chamber, whereas cells without the receptor flow through the rotating chamber. In a different embodiment, the mixed population of cells can be exposed to the antibody prior to entering the rotating chamber. Beads coated with a material that binds antibodies (e.g., protein A or protein G) can be immobilized in the chamber. As the mixed population of cells is introduced in the system, those cells that are bound to the antibody will bind to the affinity matrix and retained within the chamber. In one aspect, cells with the receptor may be released from the antibody matrix by flowing a media containing, for example and without limitation, a releasing agent such as trypsin or a soluble molecule recognized by the antibody, through the rotating chamber, and collect the cells released by action of the releasing agent.

Figure 32:
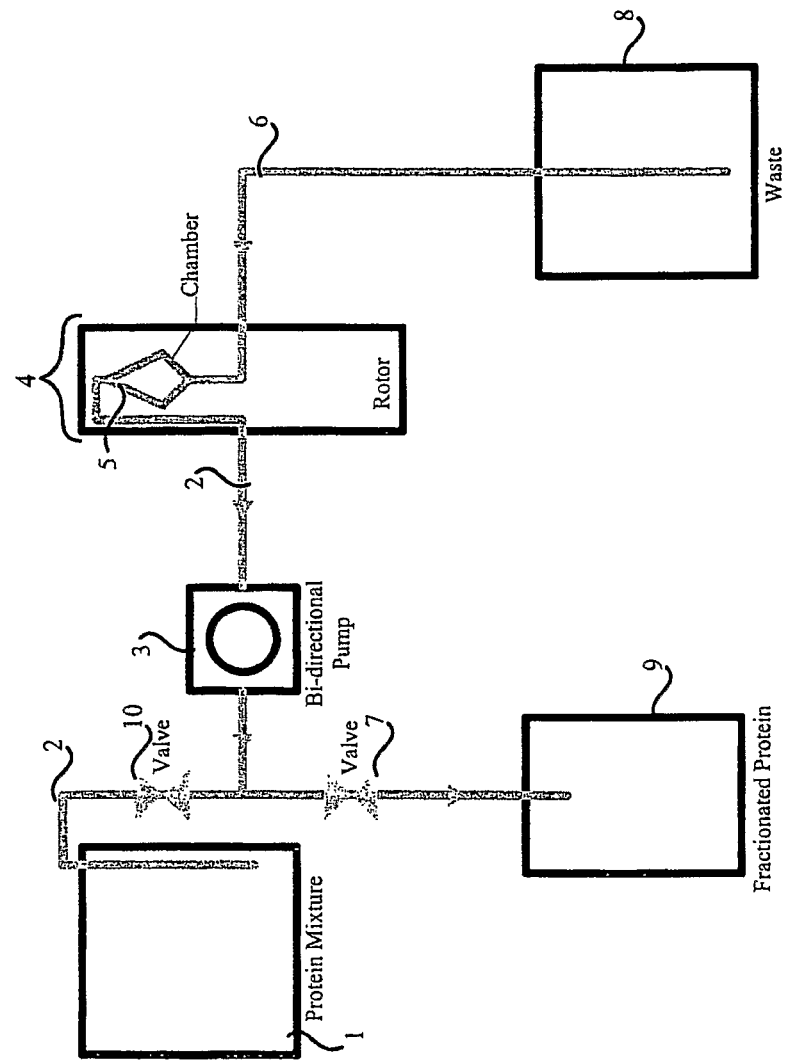
FIG. 32 is a schematic diagram of an exemplary method and system of the present invention.

Another aspect comprises methods and systems for fractionation of proteins or other biomaterials. See FIG. 32. Media containing a mixture of proteins is pumped from a container 1, via valve 10, via a bidirectional pump 3, and flows via pathway 2 into an apparatus 4 comprising a rotating chamber 5. The protein mixture media is capable of selectively precipitating proteins, and the precipitated proteins are retained within rotating chamber 5. Such conditions are known to those skilled in the art, and may include pH, ionic strength, chemicals (e.g., ammonium sulfate), or protein concentrations. The precipitated proteins are retained within rotating chamber 5 due to the balanced forces acting on the precipitated proteins. The non-precipitated proteins are not retained within rotating chamber 5, and may flow though pathway 6 to container 8. The precipitated proteins accumulate as a fluidized bed and may be collected by reversing the pump flow and flow through pathway 2, via a bidirectional pump 3, through valve 7 and into container 9. The process may be repeated and conditions in the media may be altered so that different proteins are precipitated under each differing condition (a protein fraction), and the individual fractions are stored, each in a different container 9.

Figure 33:
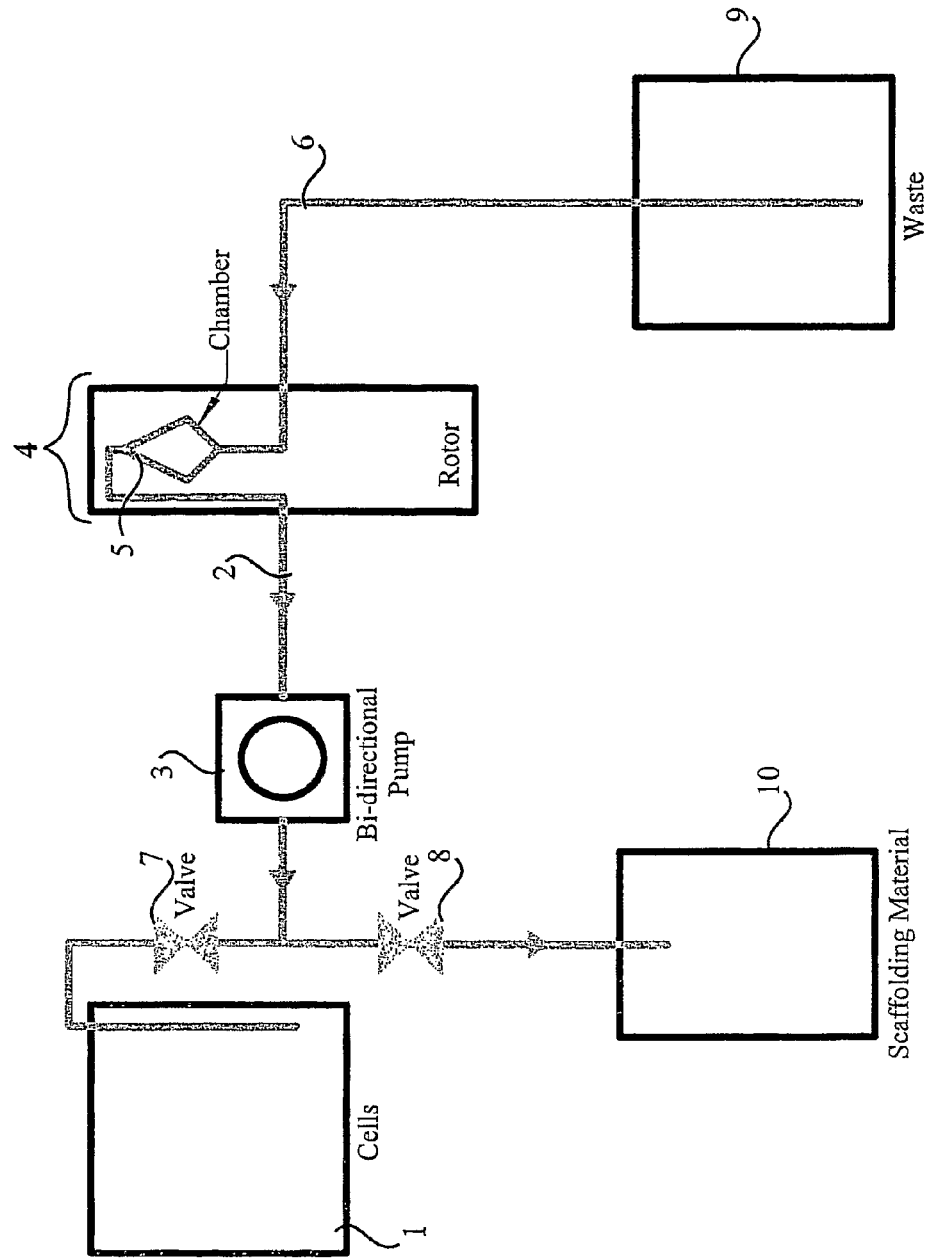
FIG. 33 is a schematic diagram of an exemplary method and system of the present invention.

Another aspect of the methods and systems of the present invention comprises associating cells or other biomaterials with scaffolds or removing cells or other biomaterials from scaffolds. As used herein, scaffold includes three dimensional structures in which, for example, cells can be associated, embedded, whether internally or externally, or both. Such scaffolds may be natural, such as the natural architecture found in a tissue comprising cells, or in a tissue in which cells have been removed, or may be made from synthetic or natural materials to form a three dimensional shape. For example, a collagen scaffold may be used by using a native structure such as a decellularized blood vessel, or from collagen molecules, used as scaffolding material, forming a random three dimensional shape. Other examples of scaffolding material include, but are not limited to alginate and proteoglycan. Another example of the methods and systems disclosed herein is shown in FIG. 33. Media containing scaffolding material is pumped from a container 10, via valve 8, via a bidirectional pump 3, via pathway 2 into an apparatus 4 comprising a rotating chamber 5. The scaffolding material is retained in rotating chamber 5. The scaffolding material may or may not be cross-linked. Media containing cells is pumped from a container 1, via valve 7, via a bidirectional pump 3, and flows via pathway 2 into the rotating chamber 5 of apparatus 4. The cells are retained within the rotating chamber and are associated with or embedded on and within the scaffolding material. The scaffolding material may or may not be cross-linked. The order of addition of scaffolding material and cells may be reversed, with cells entering the rotating chamber 5 first, followed by addition of scaffolding material. The rotating chamber may be opened and the three dimensional scaffold with associated cells can be removed.

Figure 34:
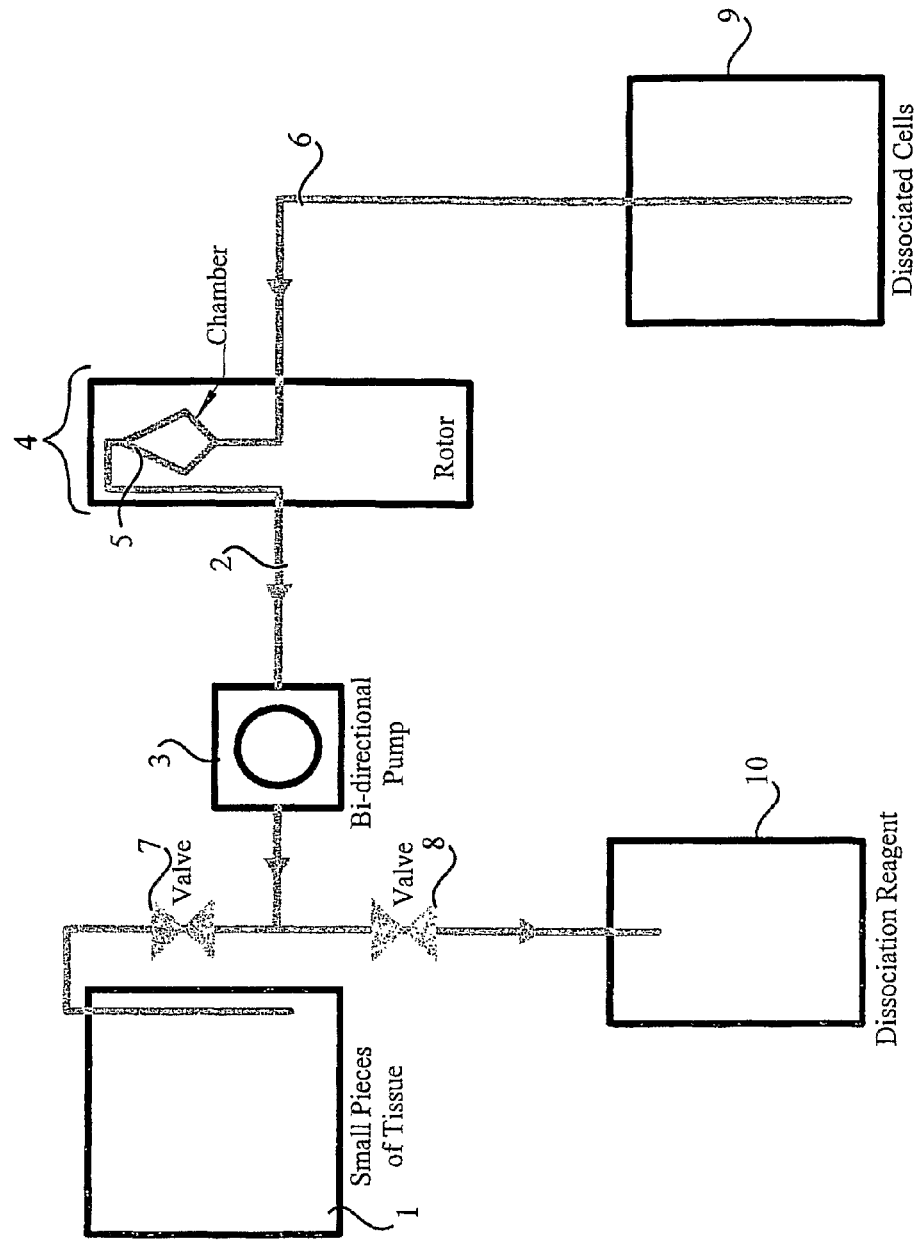
FIG. 34 is a schematic diagram of an exemplary method and system of the present invention.

Another aspect comprises removing cells or other biomaterials from a scaffold. In some embodiments, cells can be removed from samples of tissues. In other embodiments, cells can be removed from artificial supports on which they have been grown in culture, e.g., microparticles or other types of scaffolds. For example, see FIG. 34, where small pieces of tissue comprising cells are pumped from container 1 through valve 7 via a bidirectional pump 3, and flows via pathway 2 into an apparatus 4 comprising a rotating chamber 5. The small pieces of tissue are retained within rotating chamber 5 due to the balanced forces acting on the pieces of tissue. A dissociation reagent, such as for example and without limitation, trypsin, collagenase, or other digestive enzymes, is pumped from container 10, via valve 8, via a bidirectional pump 3, and flows via pathway 2 into the rotating chamber 5 of apparatus 4. The dissociation reagent acts on the immobilized pieces of tissue, and cells are removed from the tissue and flow out of the rotating chamber through pathway 6 to container 9. The released cells may enter a second rotating chamber (not shown) to be washed or placed in a different media. In this aspect, there is minimal exposure of the cells to dissociation reagents or harsh conditions, which results in less damage to the cells.

Figure 35:
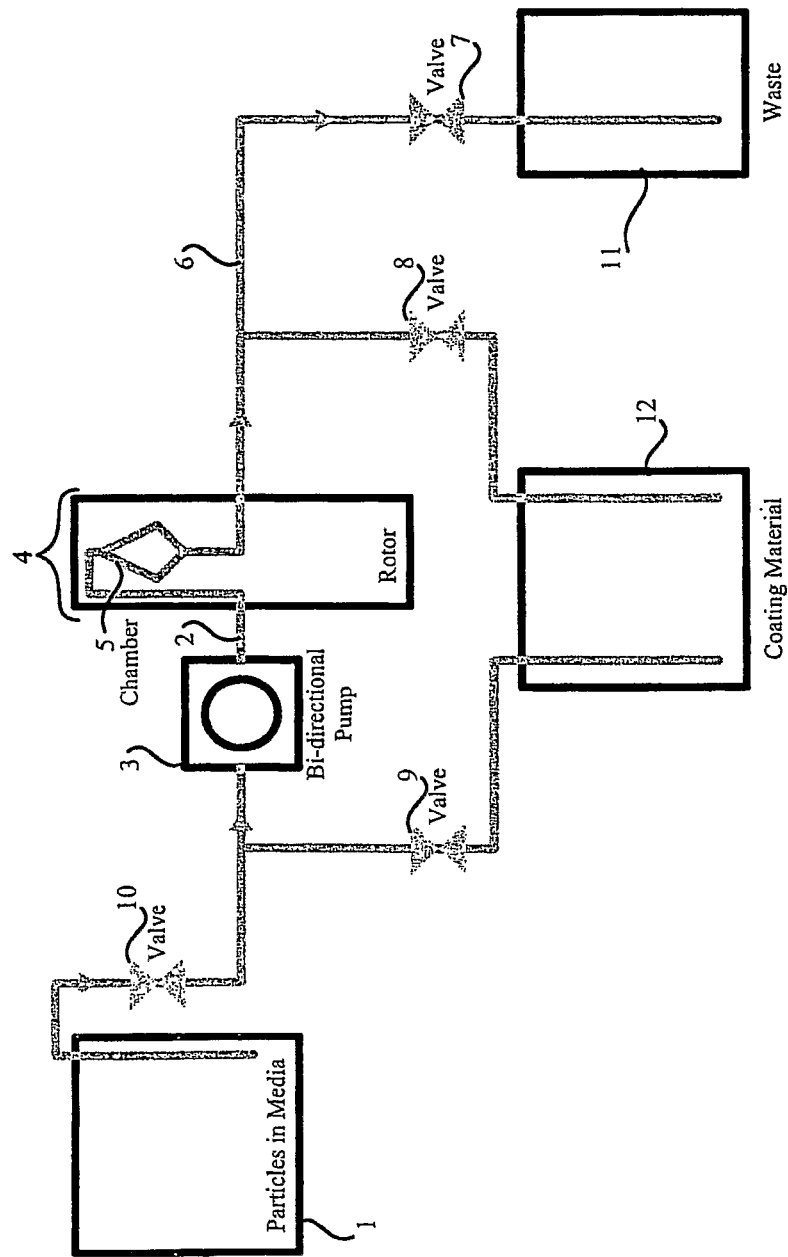
FIG. 35 is a schematic diagram of an exemplary method and system of the present invention.

The methods and systems of the present invention also comprise methods and systems for treating biomaterials. For example, and as illustrated in FIG. 35, methods and systems can be used coating of particles, for example, cells, cellular components or other biomaterials. For example, cells can be encapsulated in a particular material or more than one material (e.g., in different layers). As shown in FIG. 35, media containing particles is pumped from a container 1, via valve 10, via a bidirectional pump 3, and flows via pathway 2 into an apparatus 4 comprising a rotating chamber 5. The particles can be retained within rotating chamber 5 due to the balanced forces acting on the particles. A coating material, provided in a fluid medium, which may be a liquid or gas, is pumped from a container 12, through valve 9 via a bidirectional pump 3, and flows via pathway 2 into the rotating chamber 5 of the apparatus 4 to coat the particles. Excess coating material may flow though pathway 6 via valve 8 to container 12, and repeat the coating process in one or more cycles, or may flow through valve 7 into a waste container 11. The particles in the fluidized bed are uniformly coated, and may be transferred to the rotating chamber for other actions, such as drying or storage (not shown). One or more coats may be applied to the particles, and the coats may comprise the same materials or may comprise different materials. In one aspect, for example, a first coat can be one material and a second coat can be a different material.

The methods and systems shown herein may be used to transport cells from one container to another container, or back to the original container without exposing the cells to centrifugation, filtration, and pelleting hazards. The examples shown herein can be modified for any procedures wherein cellular manipulation, isolation, concentration, media exchange or easy transfer of cells is desired. Such procedures are contemplated by the present invention.

As discussed above, the methods and systems of the present invention may employ a rotor (which may be driven by a motor), one or more valves, and/or one or more pumps. These components may be controlled by one or more controller. In other words, a single controller may control all the components or some or all of the components may have dedicated controllers. In some embodiments, the controller(s) direct: 1) the opening and closing of the valve(s), 2) the flow rates of the pump(s), 3) the rotational speed of the rotor, either directly or via the motor, 4) the rotational speed of the chamber, and/or 5) a flow velocity of fluid and/or particles from a fluid source, such as a bioreactor. In some embodiments, the controller(s) may direct the application of an electric field, such as, for example, an electric field applied in the electroporation techniques described in more detail above.

The present invention is more particularly described in the following examples that are intended as illustrative only since numerous modifications and variations therein will be apparent to those skilled in the art.

EXAMPLES

Example 1

The methods and systems disclosed herein were used as a perfusion bioreactor process. In this example, the methods and systems as shown in FIG. 12 and FIG. 13 were used to remove spent media from a bioreactor container, and to return media to the bioreactor to perfuse the cells within the bioreactor. There were some cells in the media leaving the bioreactor (the spent or used media). The cells and the media were flowed through a rotating chamber which retained or captured the cells present in the spent media, and the spent media continued out of the rotating chamber into a container for disposal. After a certain time period, the fluid flow was reversed, and media, such as fresh new media, was flowed into the rotating chamber. The centrifugal force and the fluid flow force within the chamber acted at least partially in the same direction, and the cells flowed out of the rotating chamber and were returned to the bioreactor, along with the fresh media. This comprised one perfusion cycle. After a desired time, the perfusion cycle was repeated by reversing the fluid flow and pumping spent media and cells out of the bioreactor again. A stirred tank bioreactor process is referred to herein as a batch process.

To compare the perfusion process to a batch process in which cells were not removed, two 15 L Applikon stir-tank bioreactors containing 5 L of CDCHO media (Invitrogen) were inoculated with CHO-S cells (Invitrogen) to a cell density of $0.26 \times 10^6$ cells/mL. Cell counts were performed daily to monitor growth and viability of cultures. Continuous perfusion cycles, in which the spent media was removed from the bioreactor container, along with some cells, wherein most of the cells were captured by a rotating chamber, while the fluid flowed in one direction, and then fluid flow was reversed so that media, such as fresh media, and the captured cells were returned to the bioreactor container, was initiated in one of the bioreactors on Day 3.

In the perfusion bioreactor, a perfusion rate was maintained at 5 L/day by media feed at a rate that matched the rate of the harvest of spent media. The 5 L/day rate gave a one volume/day exchange of media for the bioreactor. The cells leaving the bioreactor were captured and returned to the bioreactor.

The volume of the bioreactor was 5 L, temperature was maintained at 37° C., and the pH was 6.9 to 7.4. The dissolved oxygen was 30%, with an impeller speed of 120 rpm, low air, and a carbon dioxide overlay to aid in pH control. The rotating chamber had a capacity of 30 mL, and was rotated at 800 rpm. The exchange rate was one volume/day and the cycle time was 30 minutes.

Figure 14:
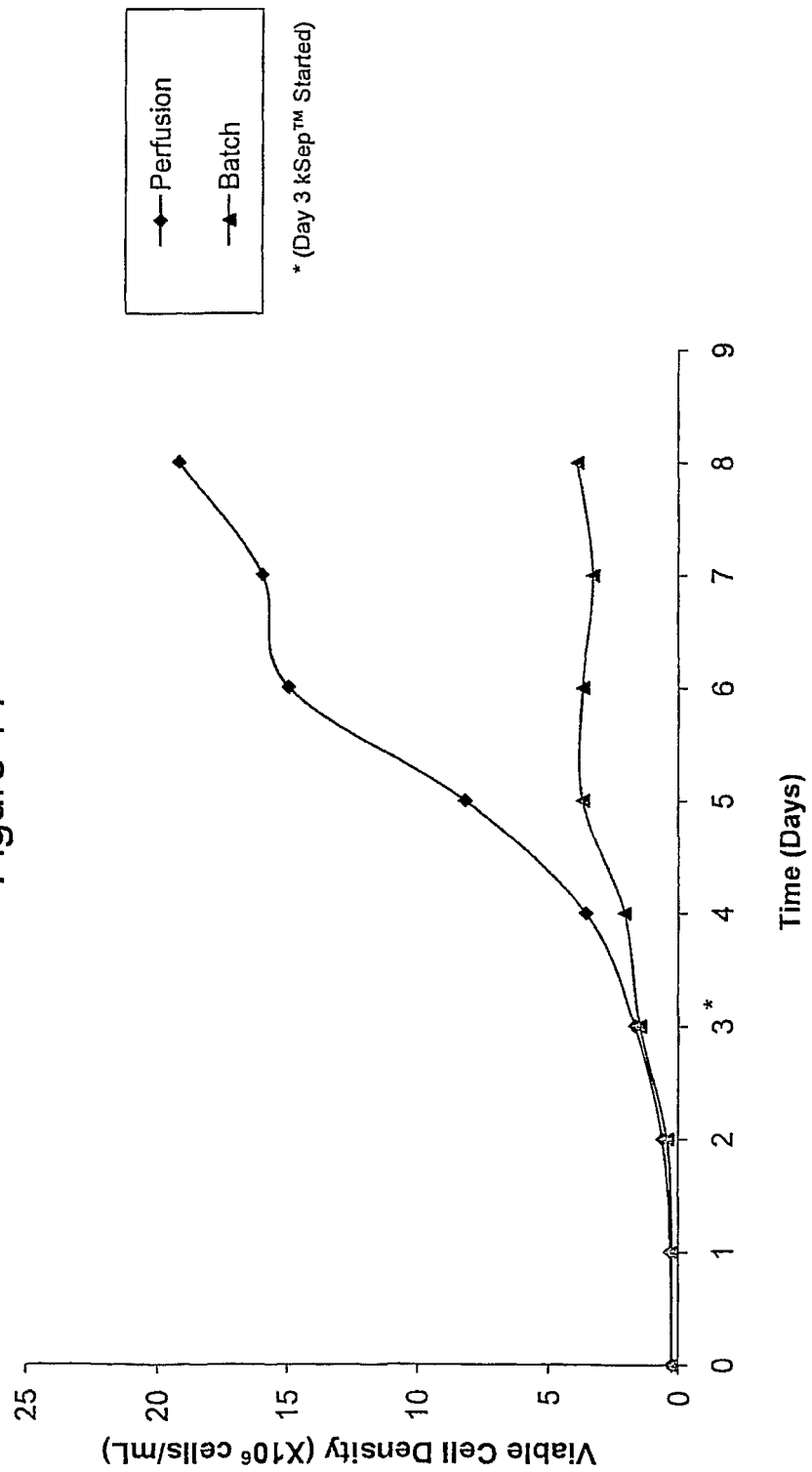
FIG. 14 is a graph showing the viable cell density when using an exemplary method and system of the present invention.
Figure 15:
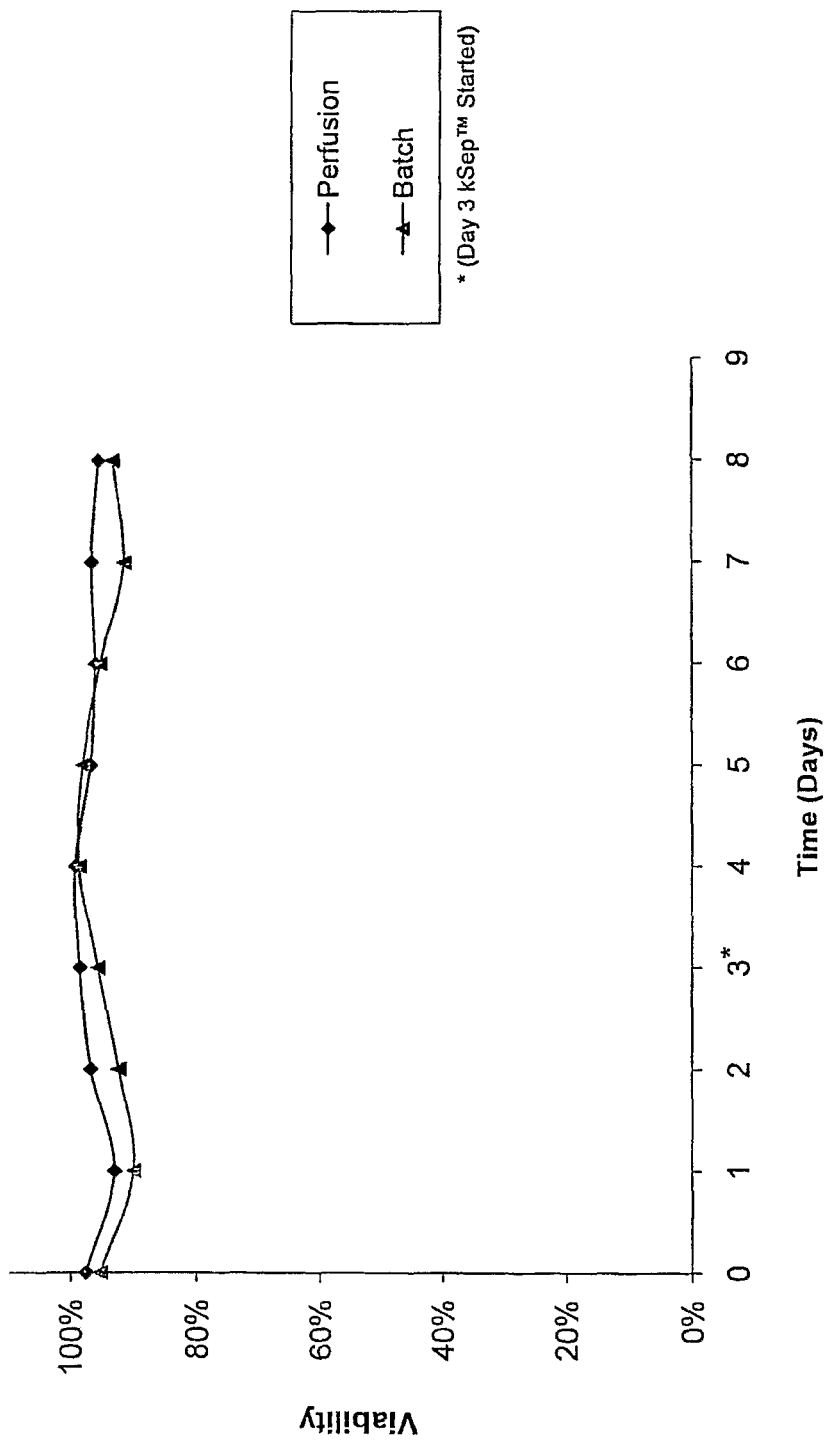
FIG. 15 is a graph showing the viable cells using an exemplary method and system of the present invention.

In the perfusion cycle, every 30 minutes, the fluid flow was reversed, so that in the rotating chamber, the centrifugal force and the fluid force were no longer balanced in opposition to each other, and the fluid force and the centrifugal force worked in the same direction to remove the fluidized cell bed of captured cells from the rotating chamber, and return the cells and media to the bioreactor. After initiation of the perfusion cycle process, viable cell density (VCD) consistently increased in the perfusion process sample in comparison to the batch process sample (FIG. 14). The experiment was terminated on Day 8, after five days of removal, immobilization and return of the cells, every 30 minutes. At Day 8, VCD in the perfusion bioreactor reached $19.2 \times 10^6$ cells/mL while VCD in the batch bioreactor was $3.9 \times 10^6$ cells/mL. Viability remained >95% throughout the experiment (FIG. 15), indicating that the movement of the media and the capture of the cells was not deleterious to the cells. The data show that using the systems and methods disclosed herein for perfusion bioreactor growth of cells produces higher cell mass than batch process using traditional stir-tank bioreactor.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method for manipulating cells using a fluidized bed, the method comprising:
   rotating a chamber about an axis to create a centrifugal force field, the chamber comprising an inlet and an outlet;
   flowing a first stream containing a first media and cells into the chamber through the inlet, wherein flowing the first stream acts to create a force which opposes the centrifugal force, wherein the cells are cells, cellular organelles, nanoparticles, or microparticles, and wherein the cells comprise a single population of cells;
   forming a fluidized bed of cells in the chamber, wherein the forces substantially immobilize the cells in the fluidized bed by the summation of vector forces acting on the cells;
   collecting the first media substantially without particles passing through the outlet of the chamber; then
   manipulating the cells in the fluidized bed, wherein said manipulating is selected from the group consisting of removing, concentrating, diluting, exchanging media, harvesting, transferring, dispensing, transfecting, electroporating, separating, extracting, isolating, selecting, purifying, coating, binding, physically modifying, and altering the environment; and thereafter
   removing the cells from the fluidized bed, wherein removing the particles comprises:
      flowing a second stream into the chamber through the outlet, wherein flowing the second stream acts to create a force at least partially in the same direction as the centrifugal force field; and
      collecting the cells passing through the inlet of the chamber.

2. The method of claim 1, the method further comprising:
   providing a cell culture system, wherein the first stream containing the first media and particles flows from the cell culture system into the chamber,
   exchanging the media; and
   delivering the cells and exchanged media to the cell culture system after removing the cells from the fluidized bed.

3. The method of claim 1, wherein manipulating the cells comprises transfecting the cells, and wherein transfecting the cells comprises circulating a transfection stream containing a transfection reagent complex through the fluidized bed of cells one or more times.

4. The method of claim 1, wherein manipulating the cells comprises electroporating the cells, and wherein electroporating the cells comprises:
   applying an electric current to the fluidized bed of cells; and
   altering the permeability of the cells.

5. The method of claim 4, wherein electroporating the cells further comprises:
   flowing a charged molecule stream containing charged molecules into the chamber through the inlet before, concurrently with, and/or after applying the electric current; and
   incorporating the charged molecules into the cells.

6. The method of claim 1, wherein manipulating the cells comprises concentrating the cells, wherein concentrating the cells comprises receiving the cells in a concentrated cell harvest container after removing the cells.

7. The method of claim 1, wherein manipulating the cells comprises exchanging the media, and wherein exchanging the media comprises:
   flowing a new media stream comprising a second media into the chamber through the inlet; and
   replacing at least some of the first media in the fluidized bed with the second media.

8. The method of claim 1, wherein manipulating the cells comprises harvesting the cells, and wherein harvesting the cells comprises receiving the cells in a cell harvest container after removing the cells.

9. The method of claim 1, wherein manipulating the cells comprises dispensing the cells, and wherein dispensing the cells comprises receiving a measured amount of cells in a one or more dispensed cell containers after removing the cells.

10. The method of claim 1, wherein manipulating the cells comprises coating the cells, and wherein coating the cells comprises:
    flowing a coating stream containing a coating material into the chamber through the inlet; and
    coating the cells retained in the fluidized bed with the coating material.

11. The method of claim 1, wherein the axis is a substantially horizontal axis.

12. The method of claim 1, wherein the axis is a substantially vertical axis.

* * * * *

UNITED STATES PATENT AND TRADEMARK OFFICE
CERTIFICATE OF CORRECTION

| | | |
|---|---|---|
| PATENT NO. | : 9,090,910 B2 | Page 1 of 1 |
| APPLICATION NO. | : 13/054276 | |
| DATED | : July 28, 2015 | |
| INVENTOR(S) | : Mehta et al. | |

It is certified that error appears in the above-identified patent and that said Letters Patent is hereby corrected as shown below:

In the Specification:
Column 9, Line 17: delete "thereof As used"
        and insert -- thereof. As used --

In the Claims:
Column 29, Claim 1, Lines 34-35: delete "force, wherein the cells are cells, cellular organelles, nanoparticles, or microparticles and wherein the cells"
        and insert -- force and wherein the cells --

Column 29, Claim 1, Line 41: delete "without particles passing through"
        and insert -- without cells passing through --

Column 29, Claim 1, Line 51: delete "the particles comprises"
        and insert -- the cells comprises --

Signed and Sealed this
Third Day of May, 2016

Michelle K. Lee
*Director of the United States Patent and Trademark Office*